United States Patent
Navratil et al.

(10) Patent No.: US 8,207,195 B2
(45) Date of Patent: Jun. 26, 2012

(54) METHOD FOR TREATING NEUROLOGICAL AND NEUROPATHIC DISEASES USING RHO KINASE INHIBITOR COMPOUNDS

(75) Inventors: Tomas Navratil, Carrboro, NC (US); John W. Lampe, Cary, NC (US); Emilee H. Fulcher, Cary, NC (US); Ward M. Peterson, Morrisville, NC (US)

(73) Assignee: Inspire Pharmaceuticals, Inc., Whitehouse Station, NJ (US)

( * ) Notice: Subject to any disclaimer, the term of this patent is extended or adjusted under 35 U.S.C. 154(b) by 343 days.

(21) Appl. No.: 12/492,848

(22) Filed: Jun. 26, 2009

(65) Prior Publication Data
US 2009/0325934 A1    Dec. 31, 2009

Related U.S. Application Data

(60) Provisional application No. 61/076,063, filed on Jun. 26, 2008, provisional application No. 61/169,239, filed on Apr. 14, 2009, provisional application No. 61/169,635, filed on Apr. 15, 2009.

(51) Int. Cl.
*A61K 31/47* (2006.01)
*A61K 31/415* (2006.01)
*A61K 31/40* (2006.01)

(52) U.S. Cl. ............... 514/313; 514/403; 514/410
(58) Field of Classification Search .......... 514/313, 514/403, 410
See application file for complete search history.

(56) References Cited

U.S. PATENT DOCUMENTS

| 2004/0102437 A1 | 5/2004 | Takami et al. |
| 2005/0148640 A1 | 7/2005 | Come et al. |
| 2006/0167043 A1 | 7/2006 | Wakubo et al. |
| 2008/0214614 A1 | 9/2008 | Lampe et al. |

FOREIGN PATENT DOCUMENTS

| EP | 1541151 A1 | 6/2005 |
| WO | WO 01/56988 A1 | 8/2001 |
| WO | WO 2006/072792 A2 | 7/2006 |
| WO | WO 2008/077057 A2 | 6/2008 |

OTHER PUBLICATIONS

Büyükaf Büyükafşarar K, Yalçin I, Kurt AH, Tiftik RN, Sahan-Firat S, Aksu F. Rho-kinase inhibitor, Y-27632, has an antinociceptive effect in mice. Eur J Pharmacol. Jul. 10, 2006;541(1-2):49-52. Epub May 20, 2006.*
King, F.D. (Ed.), "Bioisosteres, conformational restriction and pro-drugs—case history: an example of a conformational restriction approach," Medical Chemistry: Principles and Practice, 1994, Chapter 14, 206-209.*
Le Bars D, Gozariu M, Cadden SW. Animal models of nociception. Pharmacol Rev. Dec. 2001;53(4):597-652.*
Mueller BK, Mack H, Teusch N. Rho kinase, a promising drug target for neurological disorders. Nat Rev Drug Discov. May 2005;4(5):387-98.*
Dergham P et al., "Rho Signaling Pathway Targeted to Promote Spinal Cord Repair" *The Journal of Neuroscience*, 22(15):6570-6577, 2002.
Endres M et al., "Stroke protection by 3-hydroxy-3-methylglutaryl (HMG)-CoA reductase inhibitors mediated by endothelial nitric oxide synthase" *Proc Natl Acad Sci U S A*. 95: 8880-8885, 1998.
Madura T et al., "The Rho-Associated Kinase Inhibitor Fasudil Hydrochloride Enhances Neural Regeneration after Axotomy in the Peripheral Nervous System" *Plast Reconstr Surg*, 119(2):526-35, 2007.
Rikitake Y, et al., "Inhibition of Rho Kinase (ROCK) Leads to Increased Cerebral Blood Flow and Stroke Protection" *Stroke*, 36:2251-2257, (2005).
Shimizu et al., Parallel Coiled-coil Association of the RhoA-binding Domain in Rho-kinase, *J. Biol. Chem.*, 278: 46046-46051 (2003).
Yamaguchi et al., Structural Basis for Induced-Fit Binding of Rho-Kinase to the Inhibitor Y-27632. *J. Biochemistry*, vol. 140(3), pp. 305-311 (2006).

* cited by examiner

*Primary Examiner* — Paul Zarek
(74) *Attorney, Agent, or Firm* — Perkins Coie, LLP.; Viola T. Kung

(57) ABSTRACT

This invention is directed to methods of preventing or treating neurological or neuropathic diseases or conditions associated with excessive inflammation, neurodegeneration, neuro-remodeling, and axonal/neurite retraction. Particularly, this invention relates to methods treating neurological or neuropathic diseases such as cerebral ischemia, stroke, neuropathic pain, spinal cord injury, Alzheimer's disease, and multiple sclerosis, using novel rho kinase inhibitor compounds. The method comprises identifying a subject in need of the treatment, and administering to the subject an effective amount of a novel rho kinase inhibitor compound to treat the disease.

7 Claims, 8 Drawing Sheets

METHOD FOR TREATING NEUROLOGICAL AND NEUROPATHIC DISEASES USING RHO KINASE INHIBITOR COMPOUNDS

This application claims the benefit of U.S. Provisional Application Nos. 61/076,063, filed Jun. 26, 2008; 61/169,239 filed Apr. 14, 2009; and 61/169,635, filed Apr. 15, 2009; which are incorporated herein by reference in their entirety.

TECHNICAL FIELD

This invention relates to methods of preventing or treating neurological and neuropathic diseases or conditions associated with excessive inflammation, neurodegeneration, neuroremodeling, and axonal/neurite retraction. Particularly, this invention relates to methods treating neurological diseases such as cerebral ischemia, stroke, neuropathic pain, spinal cord injury, Alzheimer's disease, and multiple sclerosis, using novel rho kinase inhibitor compounds.

BACKGROUND OF THE INVENTION

Rho kinases (ROCK) have been shown to be involved in cellular functions including apoptosis, cell migration, transcriptional activation, fibrosis, cytokinesis, inflammation, and cell proliferation. In neurons ROCK plays a critical role in the inhibition of axonal growth by myelin-associated inhibitory factors such as myelin-associated glycoprotein (MAG). ROCK activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system.

Mature neurons preferentially express one of the ROCK isoforms (ROCK 2), which phosphorylates collapsin response mediator protein 2 (CRMP2) that disintegrate growth cones involved in axon branching and elongation in response to stimuli. Inhibiting ROCK 2 prevents expression of CRMP2 that allows growth-cone collapse (Dergham P et al. *The Journal of Neuroscience,* 22(15):6570-6577, 2002). By suppressing CRMP2, ROCK 2 inhibitors promote neurite expansion, axon elongation, axonal rewiring across lesions within the CNS, and neural regeneration.

Cerebral Ischemia and Stroke

Cerebral ischemia is a deficiency of blood supply to the brain, causing brain damage or an infarction. Cerebral ischemia can be caused by events such as cardiac arrest, systemic hyperperfusion, traumatic brain injury, cerebral thrombosis or hemorrhage (stroke), embolism, near-drowning, arthrosclerosis, birth asphyxia, drug overdose, and hypoxic encephalopathy. Stroke is the third leading cause of death in the U.S. and the resultant brain damage is the leading cause of adult disability as well, because cerebral ischemia can cause brain damage even if blood flow is restored (Kistler, J P et al. Etiology and clinical manifestations of transient ischemic attack. In: UpToDate. Pedley, T A (ed), UpToDate, Wellesley, Mass., 2008). Indeed, such brain damage often occurs after restoration of blood flow to the brain. For example, a component of brain damage from cardiac arrest may not be histologically apparent for approximately 24 to 48 hours after resuscitation from cardiac arrest (U.S. Pat. No. 7,319,090—Methods of Treating Cerebral Ischemia). This delayed brain damage is due to reperfusion disease: i.e., activation of pathological cascades that promote toxic free radical production, release of excitatory amino acids, severe acidosis, and other cellular and molecular changes (Mackay K B et al. *Neurodegeneration* 5:319-323, 1996). A critical step in this pathway is the rapid accumulation of neutrophils, early-stage inflammation leukocytes that remain present in high concentrations for more than 24 hours after the restoration of blood flow, and it is believed that inhibition of neutrophil infiltration and/or reduction in the amount of circulating neutrophils will lead to improved neurological outcomes (Satoh S et al. *Jpn. J. Pharmacol.* 80:41-48, 1999).

Treatment for cerebral ischemia is primarily focused on restoring blood flow as soon as a positive diagnosis has been made. The use of anti-platelet and anticoagulant agents is common, including aspirin, heparin, and warfarin (Schievink W I. *Curr Opin Cardiol.* 15:316, 2000). In extreme cases of large vessel thrombosis, stents or vein grafts may be employed to divert blood flow around the blockage and restore connectivity (Cohen J E et al. *Stroke.* 34:e254, 2003). Additionally, thrombolytic treatments have been used to promote recanalization if administered within three hours of the ischemic attack, with the risk of additional hemorrhage in the infracted area (The National Institute of Neurological Disorders and Stroke rt-PA Stroke Study Group. *N Engl J Med.* 333:1581, 1995). In all cases, the cause of the cerebral ischemia is the target of treatment, but the after effects of the inflammation cascade (the major cause of brain infarction from ischemia, second only to the initial hypoxia) are largely ignored—and a rho kinase inhibitor could minimize the neutrophil migration and associated inflammatory response. Furthermore, it is known that rho kinase plays a role in suppressing nerve growth, and thus a rho kinase inhibitor administered after ischemia could not only act as a neuroprotective agent but as a neuroregenerative agent as well (WO 6,072,792 A2—Compounds Which Bind to the Active Site of Protein Kinase Enzymes).

Prophylactic treatments for cerebral ischemia and stroke utilize the above anticoagulants, and are administered to two classes of high-risk patients: first, those with hypertension and a history of cerebrovascular disease (or the condition known as transient ischemic attack), and second, those whose recent (within ten days) ischemic event makes another such event likely.

Spinal Cord Injury

There are nearly 10,000 new cases of spinal cord injury (SCI) each year (The National Spinal Cord Injury Statistical Center. www.spinalcord.uab.edu, accessed May 11, 2007). Traumatic SCI is attributable mainly to auto accidents, falls, acts of violence, or sports in which the vertebrae are fractured, dislocated or compressed. The vertebrae may also be compressed by bleeding, fluid accumulation, and swelling. Non-traumatic SCI is due to arthritis, cancer, inflammation, infection, disc degeneration, or other defects of the spine (Mueller B et al. *Nature,* 4: 387-397, 2005). Most spinal cord injuries are associated with one or more of the following characteristics: fracture of one or more of the vertebral elements, dislocation of the spinal joint(s), tearing of the supporting ligament structure, and/or disruption/herniation of the intervertebral disc (Sekhon, L H S, et al. *Spine,* 26:S2, 2001). In its more severe forms, SCI may lead to permanent loss of motor and sensory functions below the site of injury. Quadriplegia is injury at the neck level, below the cervical vertebrae, leading to paralysis of both the arms and legs. Paraplegia is injury at the lower back, below the thoracic and lumbar vertebrae, leading to paralysis of the legs. SCI results from traumatic and non traumatic injuries that damage the nerve fibers in the spinal cord responsible for carrying signals between the brain and the spinal cord, and may affect both the white and gray matter that comprise neurons. Neurons of the central nervous system (CNS) do not readily regenerate or grow after SCI due to three factors: the inherent nature of mature neurons, the extracellular inhibitory environment found in nervous tissue, and the inflammatory environment generated by the trauma (Dergham P et al. *The Journal of Neuroscience*, 22(15):6570-6577, 2002).

The Rho-ROCK 2 pathway is significantly up-regulated in mammals after spinal cord injury. ROCK 2 inhibitors also function as neuroprotectants by decreasing nervous tissue damage and cavity formation (Mueller B et al. *Nature*, 4: 387-397, 2005). Inactivation of the Rho-ROCK 2 pathway therefore stimulates and accelerates functional recovery. The activation of the Rho-ROCK 2 pathway also induces apoptosis in neurons and oligonderocytes (Mueller B et al. *Nature*, 4: 387-397, 2005). Intervention in some or all of the processes with inhibitors of ROCK could reduce the severity of the injury and improve the ultimate outcome of SCI cases.

Neuropathic Pain

Neuropathic pain is chronic pain caused by dysfunction of the peripheral or central nervous system without continuing tissue damage. This includes pain due to neuropathic and idiopathic pain syndromes, and pain associated with neuropathic-related disorders such as cancer, HIV, multiple sclerosis, shingles, spine surgery, diabetic neuropathy, causalgia, brachial plexus avulsion, occipital neuralgia, fibromyalgia, gout, and other forms of neuralgia. Neuropathic pain often involves neural hypersensitivity and can persist without any overt external stimulus. (Goodman & Gilman's "The Pharmacologic Basis of Therapeutics", 1996, p. 529, McGraw Hill).

The therapeutic objective of most pain therapy is to alleviate the symptoms of pain regardless of the cause. Current pain control therapies include the use of opioids, NSAIDs or ion channel blockers, all of which have safety profiles that are a cause for concern. Individuals with neuropathic disorders and the resulting debilitating neuropathic pain have a decreased quality of life, but agents commonly used to treat other types of pain are usually ineffective, thus there is a need for new agents that are both safe and effective in treating neuropathic pain (Beniczky S et al. *J Neural Transm*, 112(6):735-49, 2005).

Abnormal activation of the Rho kinase pathway has been demonstrated in various neuropathies (such as brain and spinal cord injuries), resulting in neurite growth inhibition. Rho kinase inhibition results in accelerated regeneration of neurons and enhanced functional recovery after neural injury, thereby potentially preventing neurodegeneration and stimulating neuroregeneration in various neurological disorders (Mueller B K et al. *Nat Rev Drug Discovery*, 4(5):387-98, 2005; Madura T et al. *Plast Reconstr Surg*, 119(2):526-35, 2007). It has been demonstrated that Rho kinase is involved in inflammatory pain and the maintenance of neuropathic pain through phosphorylation of myristoylated alanine-rich C-kinase substrate (MARCKS), which may be involved in cytoskeletal restructuring, such as synaptic trafficking and neurotransmitter release. A phosphorylation-site specific antibody against Ser159-phospho-MARCKS (pS159-Mar-Ab) revealed that MARCKS is phosphorylated at Ser159 by Rho kinase and that its phosphorylation is inhibited by a Rho kinase specific inhibitor (Tatsumi S et al. *Neuroscience*, 131 (2):491-8, 2005; Büyükafşar K et al. *Eur J Pharmacol*, 541 (1-2):49-52, 2006)

Alzheimer's Disease

Alzheimer's Disease (AD) is a dementing disorder characterized by progressive impairments in memory and cognition. It typically occurs in later life, and is associated with a multiplicity of structural, chemical and functional abnormalities involving brain regions concerned with cognition and memory. Alzheimer's disease is characterized by neurofibrillary tangles (NFTs) and by extracellular amyloid aggregates. The disease typically begins in patients between 60 to 80 years old and progresses to dementia within 5 years and death in approximately 10 years. Current first-line therapies for Alzheimer's disease are cholinesterase inhibitors which enhance the half-life of the acetylcholine in cholinergic synapses involved in learning and memory. NMDA antagonists have recently been approved and are thought to work by decreasing NMDA associated excitotocity. (Alexander, M et al. Treatment of Dementia. In: UpToDate, Rose, B D (Ed), UpToDate, Wellesley, Mass., 2008). Despite the availability of these agents, AD continues to be a debilitating disease and new treatment options are needed. It is therefore clear that there remains today a long standing need for a treatment of AD before the disease has manifested far enough to produce psychological changes, thereby allowing earlier and more effective therapeutic intervention. Furthermore, these treatments do not address the underlying cause of the disease. Alzheimer's has been linked to the toxic 42-amino acid long amyloid $-\beta$ (A$\beta$) peptides, as the primary cause of amyloid aggregates, and one possible pathway to lowering the levels of A$\beta_{42}$ is via certain rho kinase (ROCK) inhibitors, not Formula I or II of the present invention (Mueller B K et al. *Nat Rev Drug Discovery*, 4(5): 387-98, 2005).

Multiple Sclerosis

Demyelinating diseases are those in which the main pathogenic process causes the destruction of the myelin sheath, which is necessary for the integrity of central nervous system cells. Among demyelinating diseases, multiple sclerosis (MS) is the most frequent disease due to alteration of the myelin in the central nervous system and, with the exception of trauma, it is the most frequent cause of neurological impairment in young adults. It affects 1.5 million people worldwide, and its symptoms generally occur in young adults, therefore its consequences at a personal and socioeconomic level are very severe. (Noseworthy et al., *New Engl. J. Med.*, 343:938-952, 2000) Susceptibility to MS is due to unknown genetic and environmental factors.

There is a consensus among MS researchers according to which the disease has two stages, an initial inflammatory phase of an autoimmune nature, followed by a secondary progressive neurodegenerative phase. In the first phase, activated T cells cross the hematoencephalic barrier, and once inside the central nervous system, they release proinflammatory cytokines triggering an immunological cascade ending in the destruction of the myelin and death of the oligodendrocytes. Knowledge of the autoimmune process with certain detail has served to develop agents of an immuno-modulating nature, the therapeutic efficacy of which is very modest. Until now, different targets for intervention during the inflammatory phase of MS (Zamvil et al., *Neuron* 38:685-688, 2003) have been disclosed. Among them are those which are focused on reducing inflammation of the nervous system initiated by the activation of the myelin-specific T cells, promoting autoimmunity particularly against components of the myelin, entering the central nervous tissue and releasing in it pro-inflammatory cytokines such as interferon-$\gamma$ and tumor-$\alpha$ necrosis factor. The immuno-modulator interferon-1$\beta$, approved for the treatment of remitting-recurrent MS, also prevents cellular interactions leading to the penetration of activated T cells through the vascular endothelium. Other treatments in clinical trial phase are focused on neutralizing the activity of proinflammatory cytokines and/or to enhance anti-inflammatory ones. However, no medication has been generated which delays or stops the progression of the neurodegenerative phase of the disease which takes a course with progressive neurological degeneration, and which is characterized by the occurrence of severe demyelinating lesions in the white substance with massive oligodendrocyte loss, atrophy and severe axonal damage.

Recent work also implicates p75 in the regulation of axon elongation. Nerve growth factor (NGF) stimulates neurite outgrowth from embryonic rat hippocampal neurons and chick ciliary neurons, which express only p75 for NGF receptors (Yamashita et al., *Neuron* 24:585-593, 1999). These effects can be accounted for the modulation of Rho activity by p75. Rho is a small GTPase that regulates the state of actin polymerization. In its active GTP-bound form, Rho rigidifies the actin cytoskeleton, thereby inhibiting axonal elongation and mediating growth cone collapse ((Davies, A M, *Curr. Biol.*, 10:R198-200, 2000) & (Schmidt et al., *Genes Dev.*, 16:1587-1609, 2002)). Neurotrophin binding to p75 inactivates RhoA in HN10e cells as well as cerebellar neurons, whereas the over-expression of RhoA in the transfected 293 cells results in the activation of RhoA, suggesting that p75 elicits bi-directional signals. Subsequent study shows that myelin-associated glycoprotein (MAG), a glycoprotein derived from myelin, activates RhoA by a p75-dependent mechanism, thus inhibiting neurite outgrowth from postnatal sensory neurons and cerebellar neurons (Yamashita et al., *J. Cell Biol.* 157:565-570, 2002). Furthermore, Nogo and oligodendrocyte myelin glycoprotein (OMgp), the other myelin-derived inhibitors of the neurite outgrowth, act on neurons via p75 (Wang et al., *Nature* 420:74-78, 2002). p75 in complex with the Nogo receptor is suggested to form a receptor for all the myelin-derived inhibitors found so far (Wang et al., *Nat Neurosci.* 5:1302-1308, 2002). However, the precise mechanism of the regulation of Rho activity by p75 remained to be elucidated.

MS is not curable, and as such, treatments developed to date have focused on slowing the progression of the disease or moderating its symptoms. One treatment includes medicating the patients with either interferon beta-1b or an alternative, glatiramer, both of which will block the immune system's attack on myelin. The following are medications that treat the symptoms of MS: corticosteroids that will reduce inflammation of the nerve tissue, muscle relaxants, and amantadine and modafinil that will reduce fatigue (The Mayo Clinic-MS Treatments [online] 2008 [cited June 18] www.mayoclinic.org/multiple-sclerosis/treatment.html).

SUMMARY OF THE INVENTION

The present invention is directed to methods of preventing or treating neurological diseases or conditions associated with excessive inflammation, neurodegeneration, and axonal/neurite retraction. Particularly, this invention relates to methods treating neurological diseases such as cerebral ischemia, stroke, neuropathic pain, spinal cord injury, Alzheimer's disease, and multiple sclerosis, using novel rho kinase inhibitor compounds. The method comprises identifying a subject in need of the treatment, and administering to the subject an effective amount of a novel rho kinase inhibitor compound of Formula I or II to treat the disease.

The active compound is delivered to a subject by systemic administration or local administration.

DETAILED DESCRIPTION OF THE INVENTION

Definitions

Figure 1:
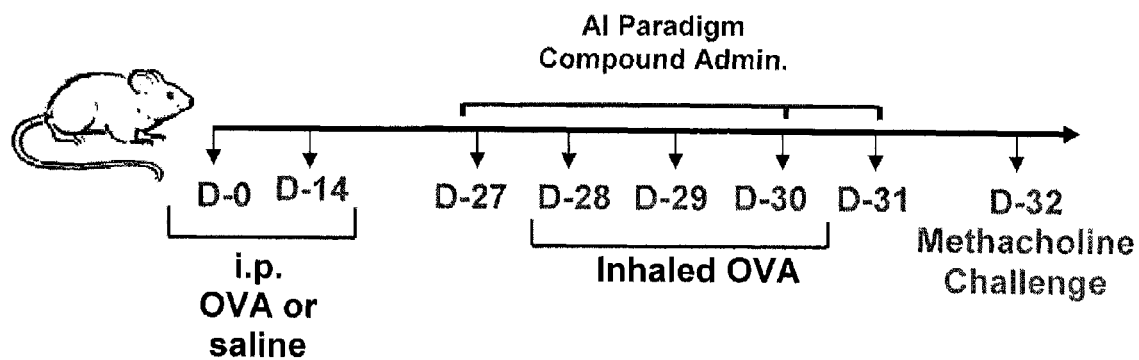
FIG. 1 shows the anti-inflammatory dosing paradigm.

When present, unless otherwise specified, the following terms are generally defined as, but are not limited to, the following:

Halo substituents are taken from fluorine, chlorine, bromine, and iodine.

"Alkyl" refers to groups of from 1 to 12 carbon atoms inclusively, either straight chained or branched, more preferably from 1 to 8 carbon atoms inclusively, and most preferably 1 to 6 carbon atoms inclusively.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Alkoxy" refers to the group alkyl-O— wherein the alkyl group is as defined above including optionally substituted alkyl groups as also defined above.

"Alkenoxy" refers to the group alkenyl-O— wherein the alkenyl group is as defined above including optionally substituted alkenyl groups as also defined above.

"Alkynoxy" refers to the group alkynyl-O— wherein the alkynyl group is as defined above including optionally substituted alkynyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl-groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl-groups preferably having from 2 to 6 carbon atoms in the alkenyl moiety and from 6 to 10 carbon atoms inclusively in the aryl moiety.

"Arylalkynyl" refers to aryl-alkynyl-groups preferably having from 2 to 6 carbon atoms inclusively in the alkynyl moiety and from 6 to 10 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl-groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Cycloalkylalkenyl" refers to cycloalkyl-alkenyl-groups preferably having from 2 to 6 carbon atoms inclusively in the alkenyl moiety and from 6 to 10 carbon atoms inclusively in the cycloalkyl moiety. Such cycloalkylalkenyl groups are exemplified by cyclohexylethenyl and the like.

"Cycloalkylalkynyl" refers to cycloalkyl-alkynyl-groups preferably having from 2 to 6 carbon atoms inclusively in the alkynyl moiety and from 6 to 10 carbon atoms inclusively in the cycloalkyl moiety. Such cycloalkylalkynyl groups are exemplified by cyclopropylethynyl and the like.

"Heteroaryl" refers to a monovalent aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl-groups preferably having from 1 to 6 carbon atoms inclusively in the alkyl moiety and from 6 to 10 atoms inclusively in the heteroaryl moiety. Such heteroarylalkyl groups are exemplified by pyridylmethyl and the like.

"Heteroarylalkenyl" refers to heteroaryl-alkenyl-groups preferably having from 2 to 6 carbon atoms inclusively in the alkenyl moiety and from 6 to 10 atoms inclusively in the heteroaryl moiety.

"Heteroarylalkynyl" refers to heteroaryl-alkynyl-groups preferably having from 2 to 6 carbon atoms inclusively in the alkynyl moiety and from 6 to 10 atoms inclusively in the heteroaryl moiety.

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

"Heterocycle-alkyl" refers to heterocycle-alkyl-groups preferably having from 1 to 6 carbon atoms inclusively in the alkyl moiety and from 6 to 10 atoms inclusively in the heterocycle moiety. Such heterocycle-alkyl groups are exemplified by morpholino-ethyl, pyrrolidinylmethyl, and the like.

"Heterocycle-alkenyl" refers to heterocycle-alkenyl-groups preferably having from 2 to 6 carbon atoms inclusively in the alkenyl moiety and from 6 to 10 atoms inclusively in the heterocycle moiety.

"Heterocycle-alkynyl" refers to heterocycle-alkynyl-groups preferably having from 2 to 6 carbon atoms inclusively in the alkynyl moiety and from 6 to 10 atoms inclusively in the heterocycle moiety.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above subtitutions can be made provided that replacing the hydrogen with the substituent does not introduce unacceptable instability to the molecules of the present invention, and is otherwise chemically reasonable.

The term "heteroatom-containing substituent" refers to substituents containing at least one non-halogen heteroatom. Examples of such substituents include, but are not limited to, hydroxy, oxo, nitro, methoxy, ethoxy, alkoxy, substituted alkoxy, trifluoromethoxy, haloalkoxy, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, aryloxy, pyridyl, imidazolyl, heteroaryl, substituted heteroaryl, heteroaryloxy, heteroarylalkyl, heteroarylalkenyl, heteroarylalkynyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above subtitutions can be made provided that replacing the hydrogen with the substituent does not introduce unacceptable instability to the molecules of the present invention, and is otherwise chemically reasonable.

"Pharmaceutically acceptable salts" are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, fumaric, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

"Tautomers" are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

"Solvates" are addition complexes in which a compound of Formula I or Formula II is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definitions of compounds in Formula I and Formula II encompass all possible hydrates and solvates, in any proportion, which possess the stated activity.

"An effective amount" is the amount effective to treat a disease by ameliorating the pathological condition or reducing the symptoms of the disease. "An effective amount" is the amount effective to improve at least one of the parameters relevant to measurement of the disease.

The inventors of the present invention have discovered compounds of Formula I or II, which are Rho kinase inhibitors, are effective in reducing inflammation, stimulating neuro-regeneration, reducing neuro-remodeling and axonal/neurite retraction. By having the above properties, compounds of Formula I or II are useful in a method of preventing or treating neurological or neuropathic diseases, particularly cerebral ischemia, stroke, neuropathic pain, spinal cord injury, Alzheimer's disease, and multiple sclerosis.

The present method comprises the steps of identifying a subject in need of treatment, and administering to the subject an effective amount of rho kinase inhibitor compound of Formula I or II.

Rho Kinase Inhibitor Compounds

The rho kinase inhibitor compounds useful for this invention include compounds of general Formula I and Formula II, and/or tautomers thereof, and/or pharmaceutically-acceptable salts, and/or solvates, and/or hydrates thereof. Compounds of general Formula I and Formula II can be prepared according to the methods disclosed in co-pending application US2008/0214614, which is incorporated herein by reference.

A compound according to Formula I or Formula II can exist in several diastereomeric forms. The general structures of Formula I and Formula II include all diastereomeric forms of such materials, when not specified otherwise. Formula I and Formula II also include mixtures of compounds of these Formulae, including mixtures of enantiomers, diastereomers and/or other isomers in any proportion.

A. Formula I

Compounds of Formula I are as follows:

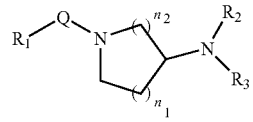

Formula I wherein: $R_1$ is aryl or heteroaryl, optionally substituted;
Q is C=O, $SO_2$, or $(CR_4R_5)_{n3}$;

$n_1$ is 1, 2, or 3;
$n_2$ is 1 or 2;
$n_3$ is 0, 1, 2, or 3;
wherein the ring represented by

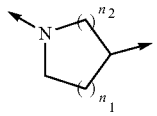

is optionally substituted by alkyl, halo, oxo, $OR_6$, $NR_6R_7$, or $SR_6$;
$R_2$ is selected from the following heteroaryl systems, optionally substituted:

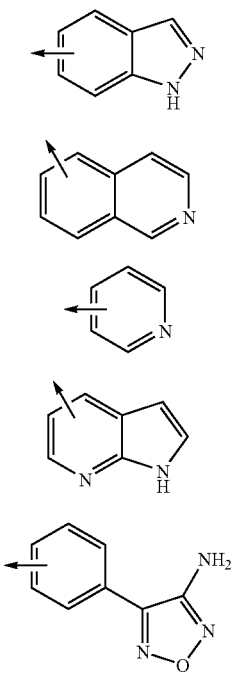

$R_3$-$R_7$ are independently H, alkyl, alkenyl, alkynyl, cycloalkyl, cycloalkenyl, cycloalkylalkyl, cycloalkylalkenyl, or cycloalkylalkynyl optionally substituted.

In Formula I, a preferred $R_1$ is substituted aryl, a more preferred $R_1$ is substituted phenyl, the preferred Q is $(CR_4R_5)_{n3}$, the more preferred Q is $CH_2$, the preferred $n_1$ is 1 or 2, the preferred $n_2$ is 1, the preferred n3 is 1 or 2, and the preferred $R_3$-$R_7$ are H.

In Formula I, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

[1] One embodiment of the invention is represented by Formula I, in which $R_2$ is 5-indazolyl or 6-indazolyl ($R_2$-1), optionally substituted.
[1a] In embodiment 1, $R_2$-1 is substituted by one or more alkyl or halo substituents.
[1b] In embodiment 1, $R_2$-1 is substituted by one or more amino, alkylamino, hydroxyl, or alkoxy substituents.
[1c] In embodiment 1, $R_2$-1 is unsubstituted.
[2] In another embodiment, the invention is represented by Formula I in which $R_2$ is 5-isoquinolinyl or 6-isoquinolinyl ($R_2$-2), optionally substituted.
[2a] In embodiment 2, $R_2$-2 is substituted by one or more alkyl or halo substituents.
[2b] In embodiment 2, $R_2$-2 is substituted by one or more amino, alkylamino, hydroxyl, or alkoxy substituents.
[2c] In embodiment 2, $R_2$-2 is unsubstituted.
[3] In another embodiment, the invention is represented by Formula I in which $R_2$ is 4-pyridyl or 3-pyridyl ($R_2$-3), optionally substituted.
[3a] In embodiment 3, $R_2$-3 is substituted by one or more alkyl or halo substituents.
[3b] In embodiment 3, $R_2$-3 is substituted by one or more amino, alkylamino, hydroxyl, or alkoxy substituents.
[3c] In embodiment 3, $R_2$-3 is unsubstituted.
[4] In another embodiment, the invention is represented by Formula I in which $R_2$ is 7-azaindol-4-yl or 7-azaindol-5-yl ($R_2$-4), optionally substituted.
[4a] In embodiment 4, $R_2$-4 is substituted by one or more alkyl or halo substituents.
[4b] In embodiment 4, $R_2$-4 is substituted by one or more amino, alkylamino, hydroxyl, or alkoxy substituents.
[4c] In embodiment 4, $R_2$-4 is unsubstituted.
[5] In another embodiment, the invention is represented by Formula I in which $R_2$ is 4-(3-amino-1,2,5-oxadiazol-4-yl)phenyl or 3-(3-amino-1,2,5-oxadiazol-4-yl)phenyl ($R_2$-5), optionally substituted.
[5a] In embodiment 5, $R_2$-5 is unsubstituted.
[6] In another embodiment, the invention is represented by Formula I in which $R_2$ is one of the groups $R_2$-1-$R_2$-5, substituted by one or more alkyl, halo, amino, alkylamino, hydroxyl, or alkoxy substituents.
[6a] In embodiment 6, $R_2$ is substituted by one or more alkyl or halo substituents.
[6b] In embodiment 6, $R_2$ is substituted by one or more amino, alkylamino, hydroxyl, or alkoxy substituents.
[7] In another embodiment, the invention is represented by Formula I in which $R_2$ is one of the groups $R_2$-1-$R_2$-5, and is unsubstituted.
[8] In another embodiment, the invention is represented by Formula I in which $R_3$ is H.
[9] In another embodiment, the invention is represented by Formula I in which Q is $(CR_4R_5)_{n3}$, and $n_3$ is 1 or 2.
[10] In another embodiment, the invention is represented by Formula I in which Q is $(CH_2)_{n3}$, and $n_3$ is 1.
[11] In another embodiment, the invention is represented by Formula I in which $R_1$ is aryl or heteroaryl substituted with one or more alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, optionally further substituted.

Compounds exemplifying embodiment 11 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[12] In another embodiment, the invention is represented by Formula I in which $R_1$ is aryl or heteroaryl substituted with one or more heteroatom-containing substituents, with the proviso that if the $R_1$ substituent is acyclic and is connected to $R_1$ by a carbon atom, then this substituent contains at least one nitrogen or sulfur atom, with the second proviso that if the substituent is acyclic and is connected to $R_1$ by an oxygen or nitrogen atom, then this substituent contains at least one additional oxygen, nitrogen or sulfur atom, and with the third proviso that if the substituent is connected to $R_1$ by a sulfone linkage "—$SO_2$—", then $R_2$ is not nitrogen- or oxygen-substituted $R_2$-2.

[12a] In embodiment 12, the heteroatom-containing substituent is connected to $R_1$ by an oxygen or nitrogen atom.

[12b] In embodiment 12, the heteroatom-containing substituent is connected to $R_1$ by a sulfide linkage, "—S—".

Compounds exemplifying embodiment 12 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[13] In another embodiment, the invention is represented by Formula I in which $R_1$ is aryl or heteroaryl substituted with one or more alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, which are further substituted with one or more heteroatom-containing substituents, with the proviso that if the $R_1$ substituent is acyclic and its heteroatom-containing substituent falls on the carbon by which it is attached to $R_1$, then the heteroatom-containing substituent contains at least one nitrogen or sulfur atom.

Compounds exemplifying embodiment 13 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

[14] In another embodiment, the invention is represented by Formula I in which $R_1$ is aryl or heteroaryl substituted with one or more alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, optionally further substituted, and $R_2$ is 5-indazolyl ($R_2$-1) or 5-isoquinolinyl ($R_2$-2), optionally substituted.

[14a] In embodiment 14, $R_2$ is 5-indazolyl ($R_2$-1), optionally substituted by one or more alkyl, halo, amino, alkylamino, hydroxyl, or alkoxy substituents.

[14b] In embodiment 14, $R_2$ is 5-isoquinolinyl ($R_2$-2), optionally substituted by one or more alkyl, halo, amino, alkylamino, hydroxyl, or alkoxy substituents.

[14c] In embodiment 14, $R_2$ is unsubstituted.

Compounds exemplifying embodiment 14 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[15] In another embodiment, the invention is represented by Formula I in which $R_1$ is aryl or heteroaryl substituted with one or more heteroatom-containing substituents, and $R_2$ is 5-indazolyl ($R_2$-1) or 5-isoquinolinyl ($R_2$-2), optionally substituted, with the proviso that if the R substituent is acyclic and is connected to $R_1$ by a carbon atom, then this substituent contains at least one nitrogen or sulfur atom, with the second proviso that if the substituent is acyclic and is connected to $R_1$ by an oxygen or nitrogen atom, then this substituent contains at least one additional oxygen, nitrogen or sulfur atom, and with the third proviso that if the substituent is connected to $R_1$ by a sulfone linkage "—$SO_2$—", then $R_2$ is not nitrogen- or oxygen-substituted $R_2$-2.

[15a] In embodiment 15, $R_2$ is 5-indazolyl ($R_2$-1), optionally substituted by one or more alkyl, halo, amino, alkylamino, hydroxyl, or alkoxy substituents.

[15b] In embodiment 15, $R_2$ is 5-isoquinolinyl ($R_2$-2), optionally substituted by one or more alkyl, halo, amino, alkylamino, hydroxyl, or alkoxy substituents.

[15c] In embodiment 15, $R_2$ is unsubstituted.

[15d] In embodiment 15, the heteroatom-containing substituent is connected to $R_1$ by an oxygen or nitrogen atom.

[15e] In embodiment 15, the heteroatom-containing substituent is connected to $R_1$ by a sulfide linkage, "—S—".

Compounds exemplifying embodiment 15 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[16] In another embodiment, the invention is represented by Formula I in which $R_1$ is aryl or heteroaryl substituted with one or more alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, at least one of which is further substituted with one or more heteroatom-containing substituents, and $R_2$ is 5-indazolyl ($R_2$-1) or 5-isoquinolinyl ($R_2$-2), optionally substituted, with the proviso that if the $R_1$ substituent is acyclic and its heteroatom-containing substituent falls on the carbon by which it is attached to $R_1$, then the heteroatom-containing substituent contains at least one nitrogen or sulfur atom.

[16a] In embodiment 16, $R_2$ is 5-indazolyl ($R_2$-1), optionally substituted by one or more alkyl, halo, amino, alkylamino, hydroxyl, or alkoxy substituents.

[16b] In embodiment 16, $R_2$ is 5-isoquinolinyl ($R_2$-2), optionally substituted by one or more alkyl, halo, amino, alkylamino, hydroxyl, or alkoxy substituents.

[16c] In embodiment 16, $R_2$ is unsubstituted.

Compounds exemplifying embodiment 16 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

The inventors have discovered certain compounds of Formula I that have properties that render them particularly useful for treating the conditions addressed by the invention. In particular, these preferred compounds can be described as compounds of Formula I in which $R_2$, $R_3$, $n_1$, and $n_2$ are limited to the combinations shown in Formulae Ia, Ib, and Ic:

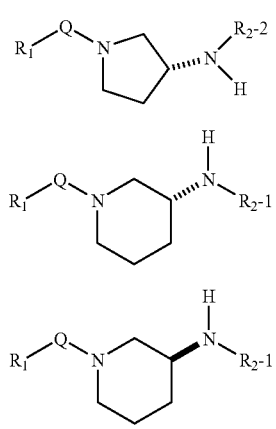

Formula Ia

Formula Ib

Formula Ic

In Formulae Ia, Ib, and Ic, the stereochemistry of the central pyrrolidine or piperidine ring is limited to the R, R, and S configurations respectively, as drawn. Further, the group $R_1$ in these Formulae is limited to phenyl, thiophene, and 6,5- or 6,6-fused bicyclic heteroaryl rings. The group $R_1$ is either unsubstituted or is optionally substituted with 1, 2 or 3 substituents independently selected from halogen, methyl, ethyl, hydroxyl, methoxy, or ethoxy.

In Formula Ia, Ib, and Ic, Q is C=O, $SO_2$, or $(CR_4R_5)_{n3}$; where $R_4$ and $R_5$ are independently H, alkyl, cycloalkyl, optionally substituted. The preferred $R_4$ and $R_5$ are H or unsubstituted alkyl. The preferred Q is $CH_2$.

In Formula Ia, Ib, and Ic, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

In a more preferred form of Formulae Ia, Ib, and Ic, $R_1$ is phenyl or a 6,5-fused bicyclic heteroaryl ring, optionally substituted by 1 or 2 substituents, Q is $CH_2$, and the group $R_2$ is unsubstituted. The most preferred 6,5-fused bicyclic heteroaryl rings are benzofuran, benzothiophene, indole, and benzimidazole.

In another more preferred form, $R_1$ of Formulae Ia, Ib, and Ic is mono- or disubstituted when $R_1$ is phenyl, with 3-substituted, 4-substituted, 2,3-disubstituted, and 3,4-disubstituted being most preferred. When $R_1$ is bicyclic heteroaryl, an unsubstituted or monosubstituted $R_1$ is most preferred.

The inventors have found that certain members of Formulae Ia, Ib, and Ic, as defined above, are particularly useful in treating the conditions addressed in this invention. The compounds of the invention are multikinase inhibitors, with inhibitory activity against ROCK1 and ROCK2, in addition to several other kinases in individual compound cases. These kinase inhibitory properties endow the compounds of the invention not only with smooth muscle relaxant properties, but additionally with antiproliferative, antichemotactic, and cytokine secretion inhibitory properties that render them particularly useful in treating conditions with proliferative or inflammatory components as described in the invention.

[17] In particular, we have found that compounds in which $R_2$ is $R_2$-2 are particularly potent inhibitors of both ROCK1 and ROCK2, and that these agents inhibit the migration of neutrophils toward multiple chemotactic stimuli and inhibit the secretion of the cytokines IL-1β, TNF-α and IL-9 from LPS-stimulated human monocytes. Compounds in which $R_1$ is heteroaryl, particularly 6,5-fused bicyclic heteroaryl, are especially preferred. These compounds are of particular value in addressing conditions with an inflammatory component.

Compounds exemplifying embodiment 17 include compounds 2.025, 2.027, 2.046, 2.047, 2.048, 2.055, 2.056, 2.057, 2.061, 2.062, 2.065, 2.074, 2.075, 2.088, and 2.090.

[18] In another embodiment, we have found that compounds of Formula Ic are potent and selective inhibitors of ROCK2, with comparatively lower inhibitory potency against ROCK1. We have demonstrated that compounds of this class typically show good smooth muscle relaxation properties and that smooth muscle relaxation effects in this class are generally correlated with ROCK2 potency. Compounds in which $R_1$ is phenyl are particularly preferred. Compounds of this embodiment are of particular value in addressing conditions where relaxation of smooth muscle, in particular vascular and bronchial smooth muscle, is of highest importance.

Compounds exemplifying embodiment 18 include compounds 1.072, 1.078, 1.079, 1.080, 1.141, 1.142, 1.148, 1.149, 1.150, 1.151, 1.154, 1.155, 1.156, 1.163, 1.164, 1.166, 1.170, 1.171, 1.175, 1.179, 1.183, 1.227, 1.277, and 1.278.

[19] In another embodiment, the inventors have found that compounds of Formula Ib are potent mixed inhibitors of ROCK1 and ROCK2, display additional inhibitory activity against the kinases Akt3 and p70S6K, and that these compounds generally display potent antiproliferative activity in models of smooth muscle cell proliferation. Compounds of this class are of particular value in addressing conditions in which an antiproliferative component is desired in combination with a smooth muscle relaxing effect.

Compounds exemplifying embodiment 19 include compounds 1.073, 1.110, 1.131, 1.132, 1.133, 1.134, 1.135, 1.136, 1.137, 1.138, 1.143, 1.144, 1.145, 1.146, 1.172, 1.173, 1.177, 1.191, 1.192, 1.203, 1.210, 1.226, 1.241, 1.242, 1.245, 1.246, 1.252, and 1.254.

[20] In another embodiment, the inventors have found that certain compounds of Formulae Ia, Ib, and Ic distribute preferentially to the lung on oral dosing. In particular, compounds in which $R_1$ is a lipophilic bicyclic heteroaryl group are preferred for this dosing behavior. Compounds of this type are especially useful for treating diseases of the lung by oral dosing while minimizing impact on other tissues.

Compounds exemplifying embodiment 20 include compounds 1.131, 1.137, 1.138, 1.143, 1.148, 1.149, 1.150, 1.166, 1.175, 1.177, 1.246, 1.252, 2.055, 2.056, 2.057, 2.065, 2.074, and 2.075.

[21] In another embodiment, the inventors have found that certain compounds of Formulae Ia, Ib, and Ic produce low plasma concentrations of the compound when dosed by the oral route. Compounds in which one substituent on $R_1$ is selected from the group methyl, ethyl, or hydroxyl are preferred for typically exhibiting this pharmacokinetic behavior. Compounds displaying this property are particularly useful for inhalation dosing, since a large portion of the material dosed in this way is typically swallowed, and it is advantageous for this swallowed portion to remain unabsorbed or to be cleared rapidly so as to minimize the impact of the compound on other tissues.

Compounds exemplifying embodiment 21 include compounds 1.078, 1.133, 1.135, 1.136, 1.145, 1.151, 1.154, 1.155, 1.156, 1.163, 1.171, 1.172, 1.173, 1.192, 1.242, 2.025, and 2.061.

Preparation of compounds of Formulae Ia, Ib, and Ic can be problematic using methods commonly known in the art. In particular, syntheses of compounds of Formulae Ib and Ic using transition metal mediated coupling reactions to form the critical bond between $R_2$-1 and the nitrogen atom are hampered by low yields when the indazole ring is not protected properly to allow a successful reaction. Specifically, the methods disclosed in UA2006/0167043 fail to provide the desired amino indazole products when the indazole is unprotected or is protected with a standard acyl protecting group such as pivalate or alkoxycarbonyl protecting groups. The inventors prepare compounds of Formulae Ia, Ib, and Ic according to the methods disclosed in the co-pending application US2008/0214614, which allows the successful protection, coupling, and deprotection of the indazole ring, thereby allowing the successful preparation of the compounds of Formulae Ib and Ic and the demonstration of their useful biological properties.

B. Formula II

A preferred compound of Formula I is where $R_1$=Ar—X, shown below as Formula II:

Formula II $$X-Ar-Q-N\underset{n_1}{\overset{n_2}{\diagdown}}N\diagup\overset{R_2}{\underset{R_3}{}}$$

wherein:

Ar is a monocyclic or bicyclic aryl or heteroaryl ring, such as phenyl;

X is from 1 to 3 substituents on Ar, each independently in the form Y—Z, in which Z is attached to Ar;

Y is one or more substituents on Z, and each is chosen independently from H, halogen, or the heteroatom-containing substituents, including but not limited to $OR_9$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$;

Each instance of Z is chosen independently from alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, heterocycle, (heterocycle)alkyl, (heterocycle)alkenyl, (heterocycle)alkynyl, or is absent;

$R_8$ is H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents, including but not limited to $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(=O)R_{12}$, $NR_{11}C(=O)OR_{12}$, $OC(=O)NR_{11}R_{12}$, or $NR_{11}C(=O)NR_{12}R_{13}$;

$R_9$ and $R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents, including but not limited to $OR_{14}$, $NR_{14}R_{15}$, $NO_2$, $SR_{14}$, $SOR_{14}$, $SO_2R_{14}$, $SO_2NR_{14}R_{15}$, $NR_{14}SO_2R_{15}$, $OCF_3$, $CONR_{14}R_{15}$, $NR_{14}C(=O)R_{15}$, $NR_{14}C(=O)OR_{15}$, $OC(=O)NR_{14}R_{15}$, or $NR_{14}C(=O)NR_{15}R_{16}$;

any two of the groups $R_8$, $R_9$ and $R_{10}$ are optionally joined with a link selected from the group consisting of bond, —O—, —S—, —SO—, —SO$_2$—, and —NR$_{17}$— to form a ring;

$R_{11}$-$R_{17}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle.

In Formula II, the preferred Y is H, halogen, $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, the more preferred Y is H, halogen, $OR_8$, $SR_8$, $SOR_8$, $SO_2R_8$, $SO_2NR_8R_9$, $NR_8SO_2R_9$, $CONR_8R_9$, or $NR_8C(=O)NR_9R_{10}$ the preferred Z is alkyl, alkenyl, alkynyl, cycloalkyl, cycloalkenyl, cycloalkylalkyl, or is absent; the more preferred Z is alkyl, alkenyl, alkynyl, cycloalkyl, or is absent, the preferred Q is $(CR_4R_5)_{n3}$, the more preferred Q is $CH_2$, the preferred $n_1$ is 1 or 2, the preferred n2 is 1, the preferred $n_3$ is 1 or 2, the preferred $R_3$-$R_7$ are H, the preferred $R_8$ is H, alkyl, arylalkyl, cycloalkyl, cycloalkylalkyl, or heterocycle, the preferred $R_8$ substituents are H, halogen, $OR_{11}$, $NR_{11}R_{12}$, $SR_{11}$, $SOR_{11}$, $SO_2R_{11}$, $SO_2NR_{11}R_{12}$, $NR_{11}SO_2R_{12}$, $CONR_{11}R_{12}$, $NR_{11}C(=O)R_{12}$, and the preferred $R_9$-$R_{17}$ are H or alkyl.

In Formula II, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

[1] One embodiment of the invention is represented by Formula II in which $R_2$ is 5-indazolyl or 6-indazolyl ($R_2$-1), optionally substituted.

[1a] In embodiment 1, $R_2$-1 is substituted by one or more alkyl or halo substituents,

[1b] In embodiment 1, $R_2$-1 is substituted by one or more amino, alkylamino, hydroxyl, or alkoxy substituents.

[1c] In embodiment 1, $R_2$-1 is unsubstituted.

[2] In another embodiment, the invention is represented by Formula II in which $R_2$ is 5-isoquinolinyl or 6-isoquinolinyl ($R_2$-2), optionally substituted.

[2a] In embodiment 2, $R_2$-2 is substituted by one or more alkyl or halo substituents.

[2b] In embodiment 2, $R_2$-2 is substituted by one or more amino, alkylamino, hydroxyl, or alkoxy substituents.

[2c] In embodiment 2, $R_2$-2 is unsubstituted.

[3] In another embodiment, the invention is represented by Formula II in which $R_2$ is 4-pyridyl or 3-pyridyl ($R_2$-3), optionally substituted.

[3a] In embodiment 3, $R_2$-3 is substituted by one or more alkyl or halo substituents.

[3b] In embodiment 3, $R_2$-3 is substituted by one or more amino, alkylamino, hydroxyl, or alkoxy substituents.

[3c] In embodiment 3, $R_2$-3 is unsubstituted.

[4] In another embodiment, the invention is represented by Formula II in which $R_2$ is 7-azaindol-4-yl or 7-azaindol-5-yl ($R_2$-4), optionally substituted.

[4a] In embodiment 4, $R_2$-4 is substituted by one or more alkyl or halo substituents.

[4b] In embodiment 4, $R_2$-4 is substituted by one or more amino, alkylamino, hydroxyl, or alkoxy substituents.

[4c] In embodiment 4, $R_2$-4 is unsubstituted.

[5] In another embodiment, the invention is represented by Formula II in which $R_2$ is 4-(3-amino-1,2,5-oxadiazol-4-yl)phenyl or 3-(3-amino-1,2,5-oxadiazol-4-yl)phenyl ($R_2$-5), optionally substituted.

[5a] In embodiment 5, $R_2$-5 is unsubstituted.

[6] In another embodiment, the invention is represented by Formula II in which $R_2$ is one of the groups $R_2$-1-$R_2$-5, substituted by one or more alkyl, halo, amino, alkylamino, hydroxyl, or alkoxy substituents.

[6a] In embodiment 6, $R_2$ is substituted by one or more alkyl or halo substituents.

[6b] In embodiment 6, $R_2$ is substituted by one or more amino, alkylamino, hydroxyl, or alkoxy substituents.

[7] In another embodiment, the invention is represented by Formula II in which $R_2$ is one of the groups $R_2$-1-$R_2$-5, and is unsubstituted

[8] In another embodiment, the invention is represented by Formula II in which $R_3$ is H.

[9] In another embodiment, the invention is represented by Formula II in which Q is $(CR_4R_5)_{n3}$, and $n_3$ is 1 or 2.

[10] In another embodiment, the invention is represented by Formula II in which Q is $(CH_2)_{n3}$, and $n_3$ is 1.

[11] In another embodiment, the invention is represented by Formula II in which for at least one substituent X, Z is alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkylalkenyl, cycloalkylalkynyl, cycloalkenyl, cycloalkylalkyl, heterocycle, (heterocycle)alkyl, (heterocycle)alkenyl, or (heterocycle)alkynyl.

Compounds exemplifying embodiment 11 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[12] In another embodiment, the invention is represented by Formula II in which for at least one substituent X, Z is absent, and Y is a heteroatom-containing substituent, including but not limited to $OR_8$, $NR_8R_9$, $SR_8$, $SOR_8$, $SO_2R_8$, $SO_2NR_8R_9$, $NR_8SO_2R_9$, $CONR_8R_9$, $NR_8C(=O)R_9$, $NR_8C(=O)OR_9$, $OC(=O)NR_8R_9$, or $NR_8C(=O)NR_9R_{10}$, with the proviso that if the substituent Y is acyclic and is connected to Ar by a carbon atom, then this substituent contains at least one nitrogen or sulfur atom, with the second proviso that if the substituent Y is acyclic and is connected to Ar by an oxygen or nitrogen atom, then this substituent contains at least one additional oxygen, nitrogen or sulfur atom, and with the third proviso that if the substituent Y is connected to Ar by a sulfone linkage "—$SO_2$—", then $R_2$ is not nitrogen- or oxygen-substituted $R_2$-2.

[12a] In embodiment 12, the heteroatom-containing substituent is connected to $R_1$ by an oxygen or nitrogen atom.

[12b] In embodiment 12, the heteroatom-containing substituent is connected to $R_1$ by a sulfide linkage, "—S—".

Compounds exemplifying embodiment 12 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[13] In another embodiment, the invention is represented by Formula II in which for at least one substituent X, Z is alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and Y is a heteroatom-containing substituent, including but not limited to $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, with the proviso that if Z is acyclic and Y falls on the carbon by which Z is attached to Ar, then Y contains at least one nitrogen or sulfur atom.

Compounds exemplifying embodiment 13 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

[14] In another embodiment, the invention is represented by Formula II in which for at least one substituent X, Z is alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and $R_2$ is 5-indazolyl ($R_2$-1) or 5-isoquinolinyl ($R_2$-2), optionally substituted.

[14a] In embodiment 14, $R_2$ is 5-indazolyl ($R_2$-1), optionally substituted by one or more alkyl, halo, amino, alkylamino, hydroxyl, or alkoxy substituents.

[14b] In embodiment 14, $R_2$ is 5-isoquinolinyl ($R_2$-2), optionally substituted by one or more alkyl, halo, amino, alkylamino, hydroxyl, or alkoxy substituents.

[14c] In embodiment 14, $R_2$ is unsubstituted.

Compounds exemplifying embodiment 14 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[15] In another embodiment, the invention is represented by Formula II in which for at least one substituent X, Z is absent, and Y is a heteroatom-containing substituent, including but not limited to $OR_8$, $NR_8R_9$, $SR_8$, $SOR_8$, $SO_2R_8$, $SO_2NR_8R_9$, $NR_8SO_2R_9$, $CONR_8R_9$, $NR_8C(=O)R_9$, $NR_8C(=O)OR_9$, $OC(=O)NR_8R_9$, or $NR_8C(=O)NR_9R_{10}$, and $R_2$ is 5-indazolyl ($R_2$-1) or 5-isoquinolinyl ($R_2$-2), optionally substituted, with the proviso that if the substituent Y is acyclic and is connected to Ar by a carbon atom, then this substituent contains at least one nitrogen or sulfur atom, with the second proviso that if the substituent Y is acyclic and is connected to Ar by an oxygen or nitrogen atom, then this substituent contains at least one additional oxygen, nitrogen or sulfur atom, and with the third proviso that if the substituent Y is connected to Ar by a sulfone linkage "—$SO_2$—", then $R_2$ is not nitrogen- or oxygen-substituted $R_2$-2.

[15a] In embodiment 15, $R_2$ is 5-indazolyl ($R_2$-1), optionally substituted by one or more alkyl, halo, amino, alkylamino, hydroxyl, or alkoxy substituents.

[15b] In embodiment 15, $R_2$ is 5-isoquinolinyl ($R_2$-2), optionally substituted by one or more alkyl, halo, amino, alkylamino, hydroxyl, or alkoxy substituents.

[15c] In embodiment 15, $R_2$ is unsubstituted.

[15d] In embodiment 15, the heteroatom-containing substituent is connected to $R_1$ by an oxygen or nitrogen atom.

[15e] In embodiment 15, the heteroatom-containing substituent is connected to $R_1$ by a sulfide linkage, "—S—".

Compounds exemplifying embodiment 15 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[16] In another embodiment, the invention is represented by Formula II in which for at least one substituent X, Z is allyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and Y is a heteroatom-containing substituent, including but not limited to $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, and $R_2$ is 5-indazolyl ($R_2$-1) or 5-isoquinolinyl ($R_2$-2), optionally substituted, with the proviso that if Z is acyclic and Y falls on the carbon by which Z is attached to Ar, then Y contains at least one nitrogen or sulfur atom.

[16a] In embodiment 16, $R_2$ is 5-indazolyl ($R_2$-1), optionally substituted by one or more alkyl, halo, amino, alkylamino, hydroxyl, or alkoxy substituents.

[16b] In embodiment 16, $R_2$ is 5-isoquinolinyl ($R_2$-2), optionally substituted by one or more alkyl, halo, amino, alkylamino, hydroxyl, or alkoxy substituents,

[16c] In embodiment 16, $R_2$ is unsubstituted.

[16d] In embodiment 16, Ar is heteroaryl.

Compounds exemplifying embodiment 16 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

In Embodiments 11-16 of Formula II, the preferred Q is $(CR_4R_5)_{n3}$, the more preferred Q is $CH_2$, the preferred $n_1$ is 1 or 2, the preferred $n_2$ is 1, the preferred $n_3$ is 1 or 2, and the preferred $R_3$ is H.

The inventors have discovered certain compounds of Formula II that have properties that render them particularly useful for treating the conditions addressed by the invention. In particular, these preferred compounds of Embodiments 14, 15 and 16 can be described as compounds of Formula II in which $R_2$, $R_3$, $n_1$, and $n_2$ are limited to the combinations shown in Formulae Ia, IIb, and IIc:

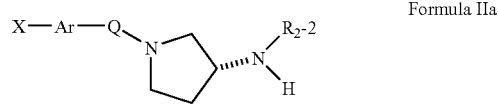

Formula IIa

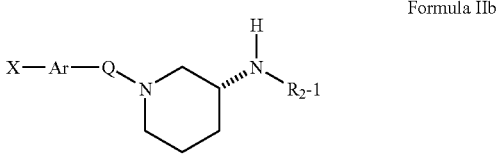

Formula IIb

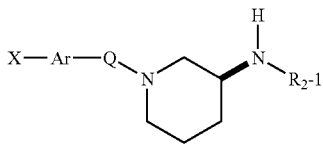

Formula IIc

In Formulae Ia, IIb, and IIc, the stereochemistry of the central pyrrolidine or piperidine ring is limited to the R, R, and S configurations respectively, as drawn.

In Formula IIa, IIb, and IIc, Q is C=O, $SO_2$, or $(CR_4R_5)_{n3}$; where $R_4$ and $R_5$ are independently H, alkyl, cycloalkyl, optionally substituted. The preferred $R_4$ and $R_5$ are H or unsubstituted alkyl. The preferred Q is $CH_2$.

In Formula IIa, IIb, and IIc, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

In a more preferred form of Formulae Ia, IIb, and IIc, Ar is phenyl or a 6,5- or 6,6-fused bicyclic heteroaryl ring, substituted by 1 or 2 substituents X, and Q is $CH_2$. The most preferred 6,5-fused bicyclic heteroaryl rings are benzofuran, benzothiophene, indole, and benzimidazole.

In its more preferred form, Ar of Formulae IIa, IIb, and IIc is mono- or disubstituted when Ar is phenyl, with 3-substituted, 4-substituted, 2,3-disubstituted, and 3,4-disubstituted being most preferred. When Ar is bicyclic heteroaryl, a monosubstituted Ar is most preferred.

The inventors have found that certain members of Formulae Ia, IIb, and IIc, as defined above, are particularly useful in treating the conditions addressed in this invention. The compounds of the invention are multikinase inhibitors, with inhibitory activity against ROCK1 and ROCK2, in addition to several other kinases in individual compound cases. These kinase inhibitory properties endow the compounds of the invention not only with smooth muscle relaxant properties, but additionally with antiproliferative, antichemotactic, and cytokine secretion inhibitory properties that render them particularly useful in treating conditions with proliferative or inflammatory components as described in the invention.

[17] In particular, we have found that compounds in which $R_2$ is $R_2$-2 are particularly potent inhibitors of both ROCK1 and ROCK2, and that these agents inhibit the migration of neutrophils toward multiple chemotactic stimuli and inhibit the secretion of the cytokines IL-1β, TNF-α and IL-9 from LPS-stimulated human monocytes. Compounds in which Ar is heteroaryl, particularly 6,5-fused bicyclic heteroaryl, are especially preferred. These compounds are of particular value in addressing conditions with an inflammatory component.

Compounds exemplifying embodiment 17 include compounds 2.020, 2.021, 2.022, 2.026, 2.031, 2.033, 2.034, 2.038, 2.039, 2.040, 2.041, 2.043, 2.044, 2.054, 2.058, 2.059, 2.060, 2.063, 2.064, 2.066, 2.067, 2.068, 2.069, 2.070, 2.071, 2.072, 2.073, 2.076, 2.077, 2.078, 2.079, 2.080, 2.081, 2.082, 2.087, 2.092, 2.093, 2.094, 2.095, 2.096, 2.097, 2.098, 2.099, and 2.100.

[18] In another embodiment, we have found that compounds of Formula IIc are potent and selective inhibitors of ROCK2, with comparatively lower inhibitory potency against ROCK1. We have demonstrated that compounds of this class typically show good smooth muscle relaxation properties and that smooth muscle relaxation effects in this class are generally correlated with ROCK2 potency. Compounds in which Ar is phenyl are particularly preferred, and compounds bearing one polar group X1 in the 3-position and a second group X2 in the 4-position are most preferred. Compounds of this embodiment are of particular value in addressing conditions where relaxation of smooth muscle, in particular vascular and bronchial smooth muscle, is of highest importance.

Compounds exemplifying embodiment 18 include compounds 1.075, 1.077, 1.090, 1.091, 1.094, 1.095, 1.107, 1.109, 1.117, 1.118, 1.124, 1.152, 1.153, 1.157, 1.158, 1.165, 1.168, 1.176, 1.181, 1.182, 1.184, 1.185, 1.186, 1.187, 1.195, 1.196, 1.197, 1.198, 1.199, 1.200, 1.201, 1.213, 1.214, 1.215, 1.217, 1.218, 1.219, 1.223, 1.224, 1.228, 1.229, 1.230, 1.233, 1.234, 1.236, 1.237, 1.238, 1.239, 1.240, 1.253, 1.255, 1.261, 1.269, 1.270, 1.272, 1.274, 1.275, 1.280, and 1.282.

[19] In another embodiment, the inventors have found that compounds of Formula IIb are potent mixed inhibitors of ROCK1 and ROCK2, display additional inhibitory activity against the kinases Akt3 and p70S6K, and that these compounds generally display potent antiproliferative activity in models of smooth muscle cell proliferation. Compounds of this class are of particular value in addressing conditions in which an antiproliferative component is desired in combination with a smooth muscle relaxing effect.

Compounds exemplifying embodiment 19 include compounds 1.074, 1.076, 1.092, 1.093, 1.096, 1.097, 1.106, 1.108, 1.113, 1.115, 1.116, 1.123, 1.125, 1.126, 1.127, 1.128, 1.129, 1.139, 1.140, 1.147, 1.159, 1.160, 1.161, 1.162, 1.174, 1.188, 1.189, 1.193, 1.194, 1.202, 1.205, 1.206, 1.207, 1.208, 1.211, 1.212, 1.221, 1.222, 1.225, 1.231, 1.232, 1.235, 1.244, 1.248, 1.249, 1.258, 1.259, 1.260, 1.262, 1.263, 1.264, 1.265, 1.266, 1.267, 1.268, 1.271, 1.273, 1.276, and 1.281.

[20] In another embodiment, the inventors have found that certain compounds of Formulae Ia, IIb, and IIc distribute preferentially to the lung on oral dosing. In particular, compounds in which Ar is a lipophilic bicyclic heteroaryl group are preferred for this dosing behavior.

Compounds of this type are especially useful for treating diseases of the lung by oral dosing while minimizing impact on other tissues.

Compounds exemplifying embodiment 20 include compounds 1.107, 1.109, 1.165, 1.106, 1.108, 2.058, 1.162, 1.264, 1.268, 1.271, 1.273, 1.217, 1.269, 2.059, 2.060, 2.066, and 2.072.

As discussed above for the compounds of Formulae Ia, Ib, and Ic, preparation of compounds of Formulae Ia, IIb, and IIc can be problematic using methods commonly known in the art. The inventors have disclosed and exemplified in US2008/0214614A1 methods to allow successful protection, coupling, and deprotection sequence that allows the successful preparation of the compounds of Formulae IIb and IIc and the demonstration of their useful biological properties.

The present compounds are useful for both oral and topical use, including use by the inhalation route. To be therapeutically effective in this way, the compounds must have both adequate potency and proper pharmacokinetic properties such as good permeability across the biological surface relevant to the delivery route. In general, compounds of Formulae I and II bearing polar functionality, particularly on Ar, have preferred absorption properties and are particularly suitable for topical use. In general, compounds bearing small lipophilic functional groups have good ROCK inhibitory potency.

$R_1$ substitution in Formula I and X in Formula II are important factors for pharmacokinetic properties and ROCK inhibitory potency. Specifically, compounds bearing polar functionality, especially those specified in the embodiments 11, 12, 13, 14, 15, and 16 in Formulae I and II, above, are particularly suitable for topical use with adequate ROCK inhibiting activity. Compounds bearing small lipophilic functional groups, as specified in the embodiments 11, 12, 13, 14, 15, and 16 in Formulae I and II, above, display ROCK inhibition with adequate permeability across biological surfaces. Compounds bearing substituents of both types are particularly preferred, and when $R_1$ (Formula I) or Ar (Formula II) is a phenyl ring, compounds with small lipophilic groups in the 4-position and polar functionality in the 3-position are most preferred.

Specific compounds illustrative of Formula I and Formula II are shown in the following Table A. The example compounds have been numbered in such a way that numbers of the form 1.nnn indicate compounds in which $R_2$ is $R_2$-1, numbers of the form 2.nnn indicate compounds in which $R_2$ is $R_2$-2, and so on in a similar fashion for the remaining compound numbers and groups $R_2$. In the following structures, hydrogens are omitted from the drawings for the sake of simplicity. Tautomers drawn represent all tautomers possible. Structures are drawn to indicate the preferred stereochemistry; where stereoisomers may be generated in these compounds, structures are taken to mean any of the possible stereoisomers alone or a mixture of stereoisomers in any ratio.

TABLE A

Exemplified Compounds.

| Compound | Structure | Select Embodiments 1-16 |
| --- | --- | --- |
| 1.001 | N-(1-(4-(methylsulfonyl)benzyl)piperidin-3-yl)-1H-indazol-5-amine | 1c, 7, 8, 9, 10, 12, 15c |

US 8,207,195 B2

TABLE A-continued

Exemplified Compounds.

| Compound | Structure | Select Embodiments 1-16 |
|---|---|---|
| 1.002 | 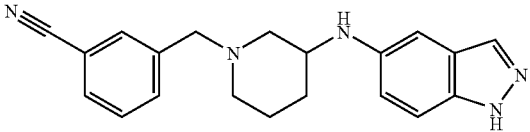<br>3-((3-(1H-indazol-5-ylamino)piperidin-1-yl)methyl)benzonitrile | 1c, 7, 8, 9, 10, 12, 15c |
| 1.003 | 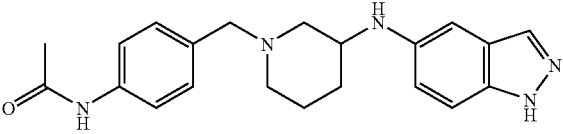<br>N-(4-((3-(1H-indazol-5-ylamino)piperidin-1-yl)methyl)phenyl)acetamide | 1c, 7, 8, 9, 10, 12a, 15c, 15d |
| 1.004 | 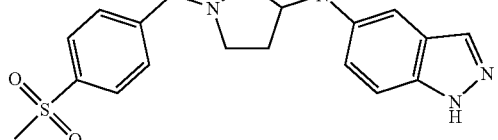<br>N-(1-(4-(methylsulfonyl)benzyl)pyrrolidin-3-yl)-1H-indazol-5-amine | 1c, 7, 8, 9, 10, 12, 15c |
| 1.005 | 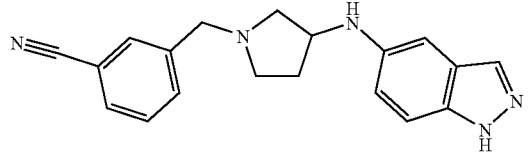<br>3-((3-(1H-indazol-5-ylamino)pyrrolidin-1-yl)methyl)benzonitrile | 1c, 7, 8, 9, 10, 12, 15c |
| 1.006 | 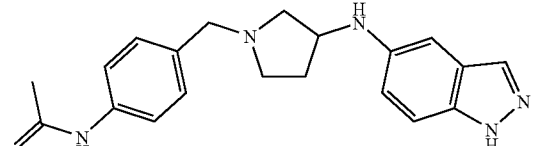<br>N-(4-((3-(1H-indazol-5-ylamino)pyrrolidin-1-yl)methyl)phenyl)acetamide | 1c, 7, 8, 9, 10, 12a, 15c, 15d |
| 1.007 | 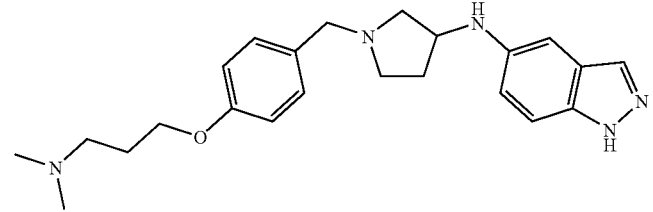<br>N-(1-(4-(3-dimethylamino)propoxy)benzyl)pyrrolidin-3-yl)-1H-indazol-5-amine | 1c, 7, 8, 9, 10, 12a, 15c, 15d |
| 1.008 | 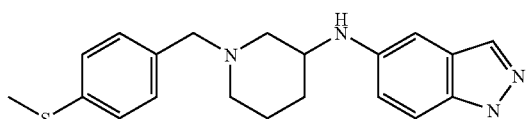<br>N-(1-(4-(methylthio)benzyl)piperidin-3-yl)-1H-indazol-5-amine | 1c, 7, 8, 9, 10, 12b, 15c, 15e |

TABLE A-continued

Exemplified Compounds.

| Compound | Structure | Select Embodiments 1-16 |
|---|---|---|
| 1.009 | 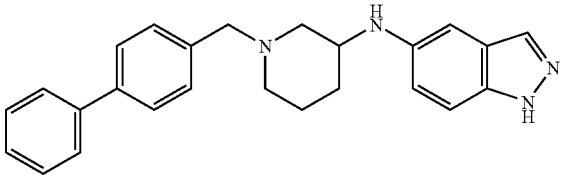<br>N-(1-(biphenyl-4-ylmethyl)piperidin-3-yl)-1H-indazol-5-amine | 1c, 7, 8, 9, 10, 11, 14c |
| 1.010 | 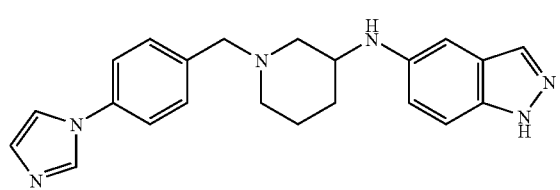<br>N-(1-(1H-imidazol-1-yl)benzyl)piperidin-3-yl)-1H-indazol-5-amine | 1c, 7, 8, 9, 10, 11, 14c |
| 1.011 | 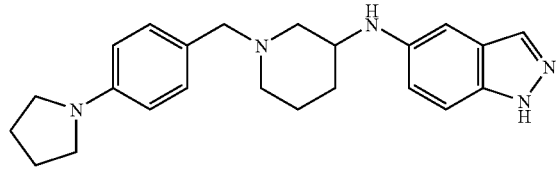<br>N-(1-(4-(pyrrolidin-1-yl)benzyl)piperidin-3-yl)-1H-indazol-5-amine | 1c, 7, 8, 9, 10, 11, 14c |
| 1.012 | 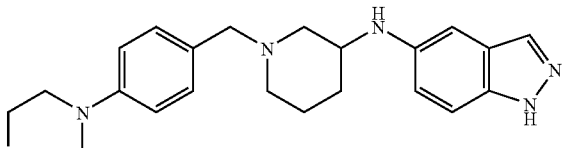<br>N-(1-(4-morpholinobenzyl)piperidin-3-yl)-1H-indazol-5-amine | 1c, 7, 8, 9, 10, 11, 14c |
| 1.013 | 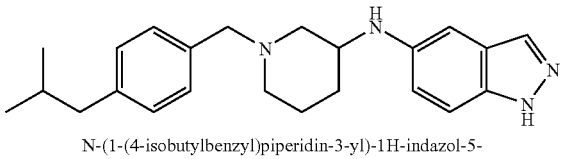<br>N-(1-(4-isobutylbenzyl)piperidin-3-yl)-1H-indazol-5-amine | 1c, 7, 8, 9, 10 |
| 1.014 | 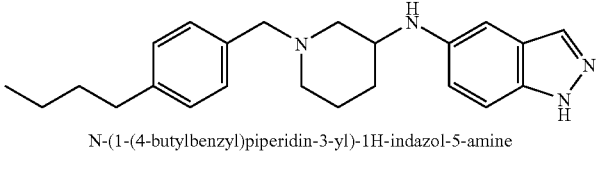<br>N-(1-(4-butylbenzyl)piperidin-3-yl)-1H-indazol-5-amine | 1c, 7, 8, 9, 10 |
| 1.015 | 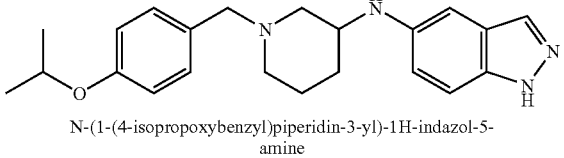<br>N-(1-(4-isopropoxybenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.016 | N-(1-(2,3-dimethylbenzyl)piperidin-3-yl)-1H-indazol-5-amine | 1c, 7, 8, 9, 10 |
| 1.017 | N-(1-(4-(ethylthio)benzyl)piperidin-3-yl)-1H-indazol-5-amine | 1c, 7, 8, 9, 10, 12b, 15c, 15e |
| 1.018 | 2-(4-((3-(1H-indazol-5-ylamino)piperidin-1-yl)methyl)phenoxy)ethanol | 1c, 7, 8, 9, 10, 12a, 15c, 15d |
| 1.019 | N-(1-(4-((dimethylamino)methyl)benzyl)piperidin-3-yl)-1H-indazol-5-amine | 1c, 7, 8, 9, 10, 13, 16c |
| 1.020 | N-(1-(4-cyclopropylbenzyl)piperidin-3-yl)-1H-indazol-5-amine | 1c, 7, 8, 9, 10, 11, 14c |
| 1.021 | N-(1-(3-cyclopropylbenzyl)piperidin-3-yl)-1H-indazol-5-amine | 1c, 7, 8, 9, 10, 11, 14c |
| 1.022 | N-(1-(4-(trifluoromethoxy)benzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.023 | N-(1-(4-isopropylbenzyl)piperidin-3-yl)-1H-indazol-5-amine | 1c, 7, 8, 9, 10 |
| 1.024 | N-(1-(2,4-dimethylbenzyl)piperidin-3-yl)-1H-indazol-5-amine | 1c, 7, 8, 9, 10 |
| 1.025 | (4-((3-(1H-indazol-5-ylamino)piperidin-1-yl)methyl)phenyl)methanol | 1c, 7, 8, 9, 10 |
| 1.026 | N-(1-(4-(cyclopropylthio)benzyl)piperidin-3-yl)-1H-indazol-5-amine | 1c, 7, 8, 9, 10, 12b, 15c, 15e |
| 1.027 | tert-butyl 4-((3-(1H-indazol-5-ylamino)piperidin-1-yl)methyl)benzylcarbamate | 1c, 7, 8, 9, 10, 13, 16c |
| 1.028 | N-(1-(4-(methylthiomethyl)benzyl)piperidin-3-yl)-1H-indazol-5-amine | 1c, 7, 8, 9, 10, 13, 16c |
| 1.029 | N-(1-(4-(methylsulfonylmethyl)benzyl)piperidin-3-yl)-1H-indazol-5-amine | 1c, 7, 8, 9, 10, 13, 16c |

TABLE A-continued

Exemplified Compounds.

| Compound | Structure | Select Embodiments 1-16 |
| --- | --- | --- |
| 1.030 | N-(1-(4-(thiophen-2-yl)benzyl)piperidin-3-yl)-1H-indazol-5-amine | 1c, 7, 8, 9, 10, 11, 14c |
| 1.031 | N-(1-benzylazepan-4-yl)-1H-indazol-5-amine | 1c, 7, 8, 9, 10 |
| 1.032 | N-(1-(4-(dimethylamino)benzyl)piperidin-3-yl)-1H-indazol-5-amine | 1c, 7, 8, 9, 10 |
| 1.033 | N-(1-(4-ethylbenzyl)piperidin-3-yl)-1H-indazol-5-amine | 1c, 7, 8, 9, 10 |
| 1.034 | N-(1-(4-ethynylbenzyl)piperidin-3-yl)-1H-indazol-5-amine | 1c, 7, 8, 9, 10, 11, 14c |
| 1.035 | N-(1-(4-(aminomethyl)benzyl)piperidin-3-yl)-1H-indazol-5-amine | 1c, 7, 8, 9, 10, 13, 16c |
| 1.036 | 1-(4-((3-(1H-indazol-5-ylamino)piperidin-1-yl)methyl)phenyl)ethanone | 1c, 7, 8, 9, 10 |

TABLE A-continued

Exemplified Compounds.

| Compound | Structure | Select Embodiments 1-16 |
|---|---|---|
| 1.037 | 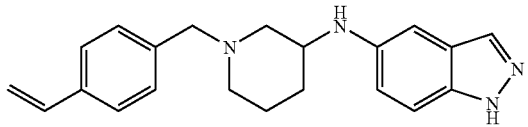<br>N-(1-(4-vinylbenzyl)piperidin-3-yl)-1H-indazol-5-amine | 1c, 7, 8, 9, 10, 11, 14c |
| 1.038 | 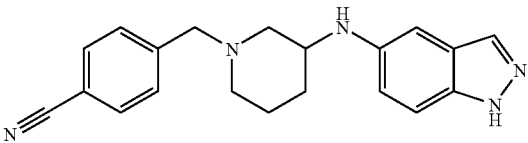<br>4-((3-(1H-indazol-5-ylamino)piperidin-1-yl)methyl)benzonitrile | 1c, 7, 8, 9, 10, 12, 15c |
| 1.039 | 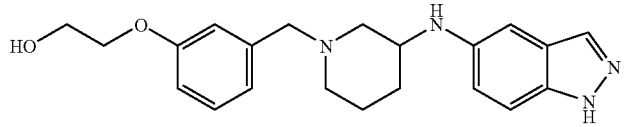<br>2-(3-((3-(1H-indazol-5-ylamino)piperidin-1-yl)methyl)phenoxy)ethanol | 1c, 7, 8, 9, 10, 12a, 15c, 15d |
| 1.040 | 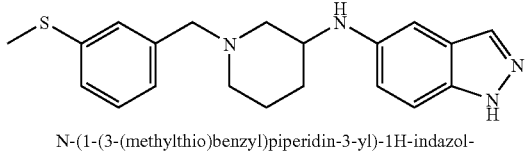<br>N-(1-(3-(methylthio)benzyl)piperidin-3-yl)-1H-indazol-5-amine | 1c, 7, 8, 9, 10, 12b, 15c, 15e |
| 1.041 | 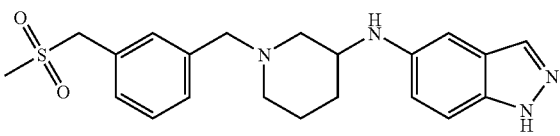<br>N-(1-(3-(methylsulfonylmethyl)benzyl)piperidin-3-yl)-1H-indazol-5-amine | 1c, 7, 8, 9, 10, 13, 16c |
| 1.042 | 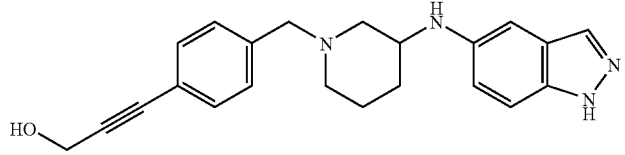<br>3-(4-((3-(1H-indazol-5-ylamino)piperidin-1-yl)methyl)phenyl)prop-2-yn-1-ol | 1c, 7, 8, 9, 10, 13, 16c |
| 1.043 | 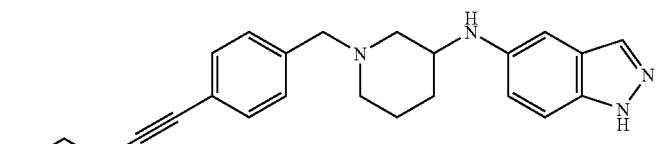<br>4-(4-((3-(1H-indazol-5-ylamino)piperidin-1-yl)methyl)phenyl)but-3-yn-1-ol | 1c, 7, 8, 9, 10, 13, 16c |

TABLE A-continued

Exemplified Compounds.

| Compound | Structure | Select Embodiments 1-16 |
|---|---|---|
| 1.044 | 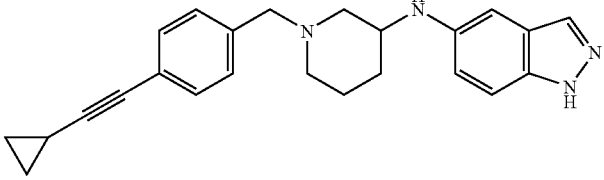<br>N-(1-(4-(cyclopropylethynyl)benzyl)piperidin-3-yl)-1H-indazol-5-amine | 1c, 7, 8, 9, 10, 11, 14c |
| 1.045 | 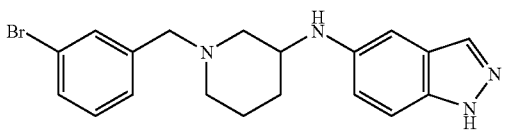<br>N-(1-(3-bromobenzyl)piperidin-3-yl)-1H-indazol-5-amine | 1c, 7, 8, 9, 10 |
| 1.046 | 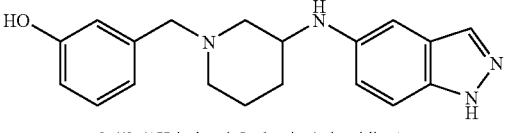<br>3-((3-(1H-indazol-5-ylamino)piperidin-1-yl)methyl)phenol | 1c, 7, 8, 9, 10 |
| 1.047 | 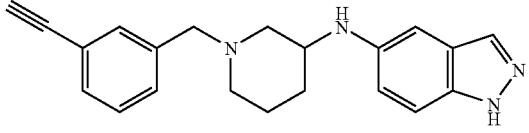<br>N-(1-(3-ethynylbenzyl)piperidin-3-yl)-1H-indazol-5-amine | 1c, 7, 8, 9, 10, 11, 14c |
| 1.048 | 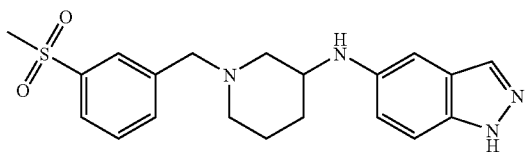<br>N-(1-(3-(methylsulfonyl)benzyl)piperidin-3-yl)-1H-indazol-5-amine | 1c, 7, 8, 9, 10, 12, 15c |
| 1.049 | 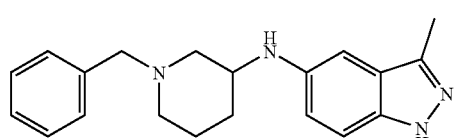<br>N-(1-benzylpiperidin-3-yl)-3-methyl-1H-indazol-5-amine | 1a, 6a, 8, 9, 10 |
| 1.050 | 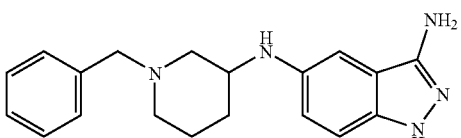<br>N5-(1-benzylpiperidin-3-yl)-1H-indazole-3,5-diamine | 1b, 6b, 8, 9, 10 |

TABLE A-continued

Exemplified Compounds.

| Compound | Structure | Select Embodiments 1-16 |
|---|---|---|
| 1.051 | 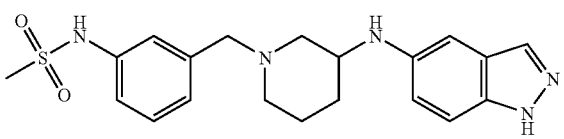<br>N-(3-((3-(1H-indazol-5-ylamino)piperidin-1-yl)methyl)phenyl)methanesulfonamide | 1c, 7, 8, 9, 10, 12a, 15c, 15d |
| 1.052 | 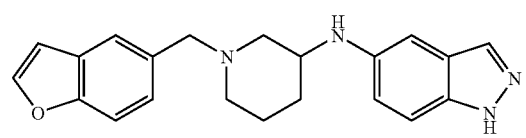<br>N-(1-(benzofuran-5-ylmethyl)piperidin-3-yl)-1H-indazol-5-amine | 1c, 7, 8, 9, 10 |
| 1.053 | 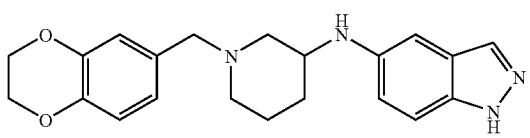<br>N-(1-((2,3-dihydrobenzo[b][1,4]dioxin-6-yl)methyl)piperidin-3-yl)-1H-indazol-5-amine | 1c, 7, 8, 9, 10 |
| 1.054 | 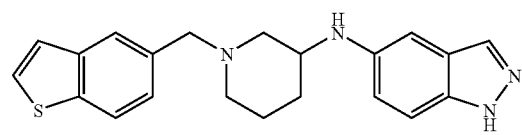<br>N-(1-(benzo[b]thiophen-5-ylmethyl)piperidin-3-yl)-1H-indazol-5-amine | 1c, 7, 8, 9, 10 |
| 1.055 | 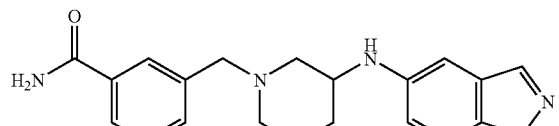<br>3-((3-(1H-indazol-5-ylamino)piperidin-1-yl)methyl)benzamide | 1c, 7, 8, 9, 10, 12, 15c |
| 1.056 | 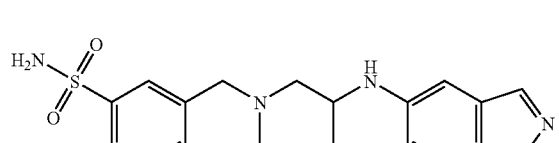<br>3-((3-(1H-indazol-5-ylamino)piperidin-1-yl)methyl)benzenesulfonamide | 1c, 7, 8, 9, 10, 12, 15c |
| 1.057 | 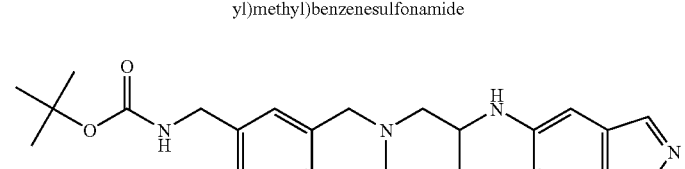<br>tert-butyl 3-((3-(1H-indazol-5-ylamino)piperidin-1-yl)methyl)benzylcarbamate | 1c, 7, 8, 9, 10, 13, 16c |

TABLE A-continued

Exemplified Compounds.

| Compound | Structure | Select Embodiments 1-16 |
|---|---|---|
| 1.058 | 2-(5-((3-(1H-indazol-5-ylamino)piperidin-1-yl)methyl)-2-methylphenoxy)ethanol | 1c, 7, 8, 9, 10, 12a, 15c, 15d |
| 1.059 | 5-((3-(1H-indazol-5-ylamino)piperidin-1-yl)methyl)-2-methylphenol | 1c, 7, 8, 9, 10 |
| 1.060 | ethyl 2-(3-((3-(1H-indazole-5-ylamino)piperidin-1-yl)methyl)phenoxy)acetate | 1c, 7, 8, 9, 10, 12a, 15c, 15d |
| 1.061 | N-(1-(3-(aminomethyl)benzyl)piperidin-3-yl)-1H-indazol-5-amine | 1c, 7, 8, 9, 10, 13, 16c |
| 1.062 | N-(1-(3,4-dichlorobenzyl)pyrrolidin-3-yl)-1H-indazol-5-amine | 1c, 7, 8, 9, 10 |
| 1.063 | N-(1-(3-(trifluoromethyl)benzyl)piperidin-3-yl)-1H-indazol-5-amine | 1c, 7, 8, 9, 10 |
| 1.064 | N-(1-(3-(trifluoromethyl)benzyl)pyrrolidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.065 | 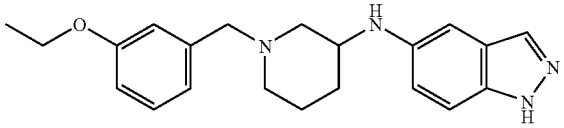<br>N-(1-(3-ethoxybenzyl)piperidin-3-yl)-1H-indazole-5-amine | 1c, 7, 8, 9, 10 |
| 1.066 | 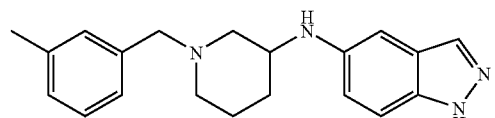<br>N-(1-(3-methylbenzyl)piperidin-3-yl)-1H-indazol-5-amine | 1c, 7, 8, 9, 10 |
| 1.067 | 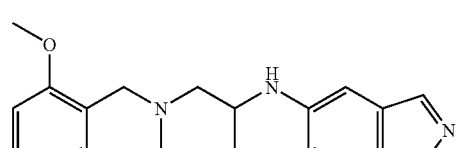<br>N-(1-(2-methoxybenzyl)piperidin-3-yl)-1H-indazol-5-amine | 1c, 7, 8, 9, 10 |
| 1.068 | 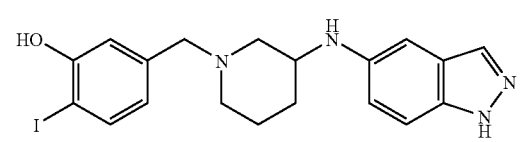<br>5-((3-(1H-indazol-5-ylamino)piperidin-1-yl)methyl)-2-iodophenol | 1c, 7, 8, 9, 10 |
| 1.069 | 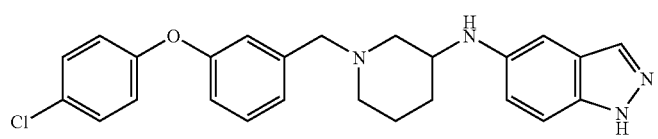<br>N-(1-(3-(4-chlorophenoxy)benzyl)piperidin-3-yl)-1H-indazol-5-amine | 1c, 7, 8, 9, 10 |
| 1.070 | 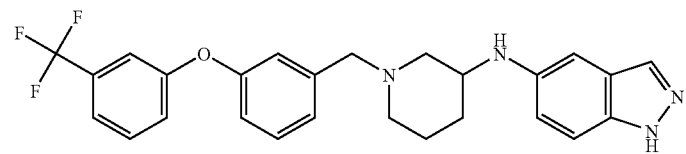<br>N-(1-(3-(3-(trifluoromethyl)phenoxy)benzyl)piperidin-3-yl)-1H-indazol-5-amine | 1c, 7, 8, 9, 10 |
| 1.071 | 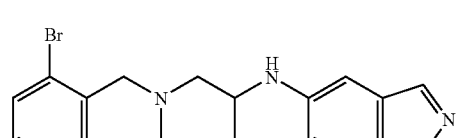<br>N-(1-(2,5-dibromobenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.072 | 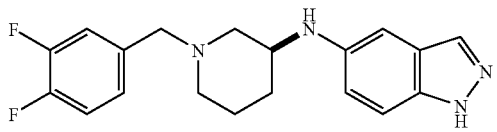<br>(S)-N-(1-(3,4-difluorobenzyl)piperidin-3-yl)-1H-indazol-5-amine | 1c, 7, 8, 9, 10 |
| 1.073 | 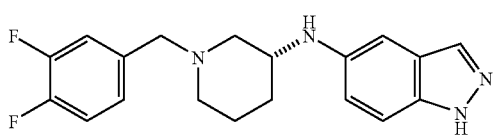<br>(R)-N-(1-(3,4-difluorobenzyl)piperidin-3-yl)-1H-indazol-5-amine | 1c, 7, 8, 9, 10 |
| 1.074 | 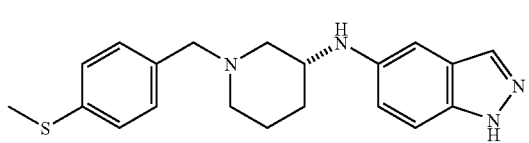<br>(R)-N-(1-(4-(methylthio)benzyl)piperidin-3-yl)-1H-indazol-5-amine | 1c, 7, 8, 9, 10, 12b, 15c, 15e |
| 1.075 | 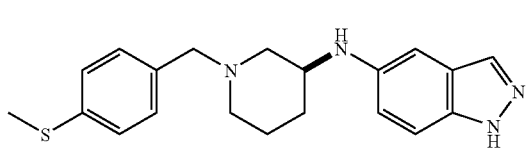<br>(S)-N-(1-(4-(methylthio)benzyl)piperidin-3-yl)-1H-indazol-5-amine | 1c, 7, 8, 9, 10, 12b, 15c, 15e |
| 1.076 | 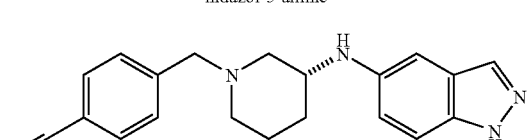<br>(R)-N-(1-(4-ethynylbenzyl)piperidin-3-yl)-1H-indazol-5-amine | 1c, 7, 8, 9, 10, 11, 14c |
| 1.077 | 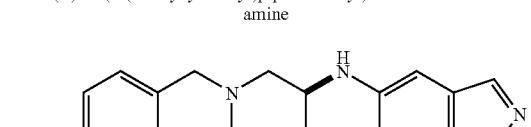<br>(S)-N-(1-(4-ethynylbenzyl)piperidin-3-yl)-1H-indazol-5-amine | 1c, 7, 8, 9, 10, 11, 14c |
| 1.078 | 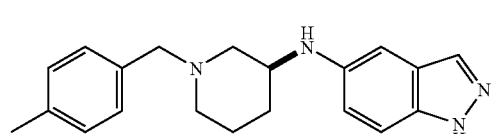<br>(S)-N-(1-(4-methylbenzyl)piperidin-3-yl)-1H-indazol-5-amine | 1c, 7, 8, 9, 10 |
| 1.079 | 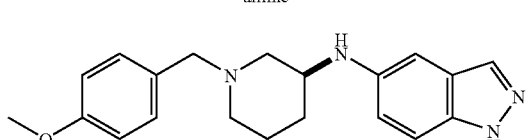<br>(S)-N-(1-(4-methoxybenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.080 | (S)-N-(1-(3,4-dichlorobenzyl)piperidin-3-yl)-1H-indazol-5-amine | 1c, 7, 8, 9, 10 |
| 1.082 | N-(1-((1H-indol-6-yl)methyl)piperidin-3-yl)-1H-indazol-5-amine | 1c, 7, 8, 9, 10 |
| 1.083 | 5-((3-(1H-indazol-5-ylamino)piperidin-1-yl)methyl)-2-ethynylphenol | 1c, 7, 8, 9, 10, 11, 14c |
| 1.084 | 3-(3-((3-(1H-indazol-5-ylamino)piperidin-1-yl)methyl)phenoxy)propan-1-ol | 1c, 7, 8, 9, 10, 12a, 15c, 15d |
| 1.085 | N-(1-(3-(2-aminoethoxy)benzyl)piperidin-3-yl)-1H-indazol-5-amine | 1c, 7, 8, 9, 10, 12a, 15c, 15d |
| 1.086 | 2-(3-((3-(1H-indazol-5-ylamino)piperidin-1-yl)methyl)phenoxy)acetic acid | 1c, 7, 8, 9, 10, 12a, 15c, 15d |
| 1.087 | N-(3-((3-(1H-indazol-5-ylamino)pyrrolidin-1-yl)methyl)phenyl)methanesulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.088 | 2-(3-((3-(1H-indazol-5-ylamino)pyrrolidin-1-yl)methyl)phenoxy)ethanol | 1c, 7, 8, 9, 10, 12a, 15c, 15d |
| 1.089 | N-(1-(3-amino-4-chlorobenzyl)piperidin-3-yl)-1H-indazol-5-amine | 1c, 7, 8, 9, 10 |
| 1.090 | (S)-2-(3-((3-(1H-indazol-5-ylamino)piperidin-1-yl)methyl)phenoxy)ethanol | 1c, 7, 8, 9, 10, 12a, 15c, 15d |
| 1.091 | (S)-N-(3-((3-(1H-indazol-5-ylamino)piperidin-1-yl)methyl)phenyl)methanesulfonamide | 1c, 7, 8, 9, 10, 12a, 15c, 15d |
| 1.092 | (R)-2-(3-((3-(1H-indazol-5-ylamino)piperidin-1-yl)methyl)phenoxy)ethanol | 1c, 7, 8, 9, 10, 12a, 15c, 15d |
| 1.093 | (R)-N-(3-((3-(1H-indazol-5-ylamino)piperidin-1-yl)methyl)phenyl)methanesulfonamide | 1c, 7, 8, 9, 10, 12a, 15c, 15d |
| 1.094 | (S)-2-(3-((3-(1H-indazol-5-ylamino)pyrrolidin-1-yl)methyl)phenoxy)ethanol | 1c, 7, 8, 9, 10, 12a, 15c, 15d |

TABLE A-continued

Exemplified Compounds.

| Compound | Structure | Select Embodiments 1-16 |
|---|---|---|
| 1.095 | (S)-N-(3-((3-(1H-indazol-5-ylamino)pyrrolidin-1-yl)methyl)phenyl)methanesulfonamide | 1c, 7, 8, 9, 10, 12a, 15c, 15d |
| 1.096 | (R)-2-(3-((3-(1H-indazol-5-ylamino)pyrrolidin-1-yl)methyl)phenoxy)ethanol | 1c, 7, 8, 9, 10, 12a, 15c, 15d |
| 1.097 | (R)-N-(3-((3-(1H-indazol-5-ylamino)pyrrolidin-1-yl)methyl)phenyl)methanesulfonamide | 1c, 7, 8, 9, 10, 12a, 15c, 15d |
| 1.098 | 2-(3-((3-(1H-indazol-5-ylamino)piperidin-1-yl)methyl)phenoxy)acetamide | 1c, 7, 8, 9, 10, 12a, 15c, 15d |
| 1.099 | 2-(6-((3-(1H-indazol-5-ylamino)piperidin-1-yl)methyl)-1H-indol-1-yl)acetamide | 1c, 7, 8, 9, 10, 13, 16c |
| 1.100 | N-(1-((1H-indol-5-yl)methyl)piperidin-3-yl)-1H-indazol-5-amine | 1c, 7, 8, 9, 10, 13, 16c |
| 1.101 | 2-(6-((3-(1H-indazol-5-ylamino)piperidin-1-yl)methyl)-1H-indol-1-yl)ethanol | 1c, 7, 8, 9, 10, 13, 16c |

TABLE A-continued

Exemplified Compounds.

| Compound | Structure | Select Embodiments 1-16 |
|---|---|---|
| 1.102 | 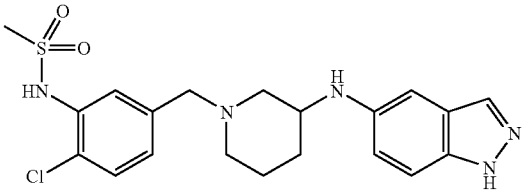<br>N-(5-((3-(1H-indazol-5-ylamino)piperidin-1-yl)methyl)-2-chlorophenyl)methanesulfonamide | 1c, 7, 8, 9, 10, 12a, 15c, 15d |
| 1.103 | 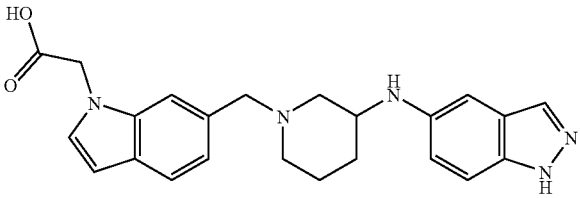<br>2-(6-((3-(1H-indazol-5-ylamino)piperidin-1-yl)methyl)-1H-indol-1-yl)acetic acid | 1c, 7, 8, 9, 10, 13, 16c |
| 1.104 | 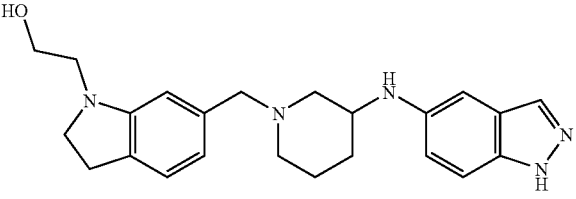<br>2-(6-((3-(1H-indazol-5-ylamino)piperidin-1-yl)methyl)indolin-1-yl)ethanol | 1c, 7, 8, 9, 10, 13, 16c |
| 1.105 | 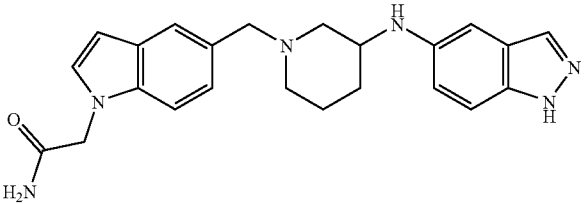<br>2-(5-((3-(1H-indazol-5-ylamino)piperidin-1-yl)methyl)-1H-indol-1-yl)acetamide | 1c, 7, 8, 9, 10, 13, 16c |
| 1.106 | 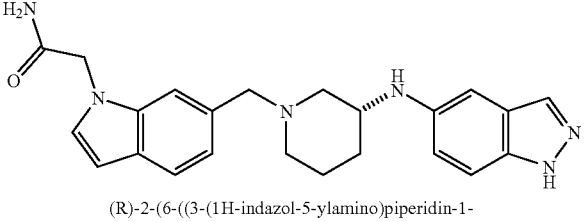<br>(R)-2-(6-((3-(1H-indazol-5-ylamino)piperidin-1-yl)methyl)-1H-indol-1-yl)acetamide | 1c, 7, 8, 9, 10, 13, 16c |
| 1.107 | 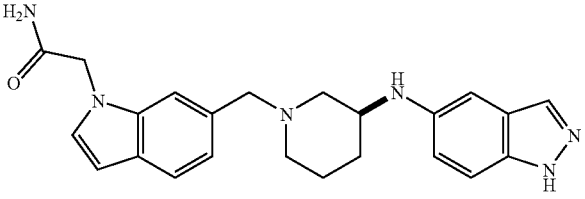<br>(S)-2-(6-((3-(1H-indazol-5-ylamino)piperidin-1-yl)methyl)-1H-indol-1-yl)acetamide | 1c, 7, 8, 9, 10, 13, 16c |

TABLE A-continued

Exemplified Compounds.

| Compound | Structure | Select Embodiments 1-16 |
|---|---|---|
| 1.108 | 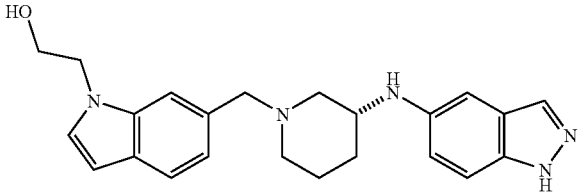<br>(R)-2-(6-((3-(1H-indazol-5-ylamino)piperidin-1-yl)methyl)-1H-indol-1-yl)ethanol | 1c, 7, 8, 9, 10, 13, 16c |
| 1.109 | 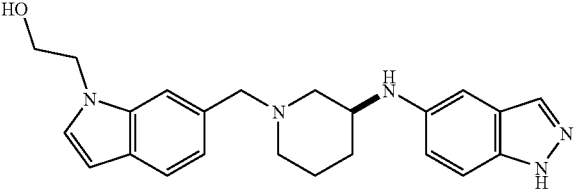<br>(S)-2-(6-((3-(1H-indazol-5-ylamino)piperidin-1-yl)methyl)-1H-indol-1-yl)ethanol | 1c, 7, 8, 9, 10, 13, 16c |
| 1.110 | 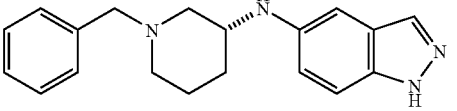<br>(R)-N-(1-benzylpiperidin-3-yl)-1H-indazol-5-amine | 1c, 7, 8, 9, 10 |
| 1.111 | 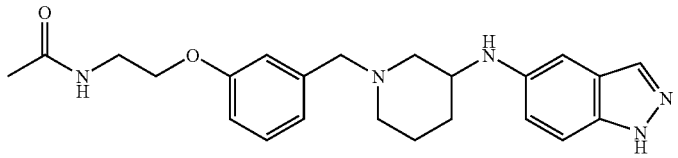<br>N-(2-(3-((3-(1H-indazol-5-ylamino)piperidin-1-yl)methyl)phenoxy)ethyl)acetamide | 1c, 7, 8, 9, 10, 12a, 15c, 15d |
| 1.112 | 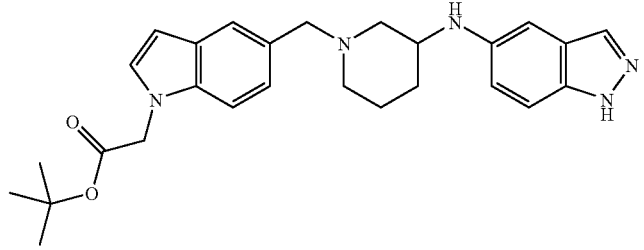<br>tert-butyl 2-(5-((3-(1H-indazol-5-ylamino)piperidin-1-yl)methyl)-1H-indol-1-yl)acetate | 1c, 7, 8, 9, 10, 13, 16c |
| 1.113 | 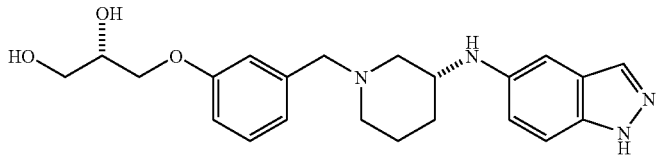<br>(S)-3-(3-(((R)-3-(1H-indazol-5-ylamino)piperidin-1-yl)methyl)phenoxy)propane-1,2-diol | 1c, 7, 8, 9, 10, 12a, 15c, 15d |

TABLE A-continued

Exemplified Compounds.

| Compound | Structure | Select Embodiments 1-16 |
|---|---|---|
| 1.114 | 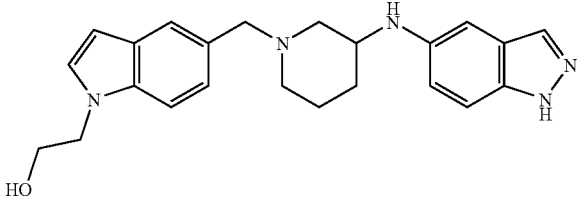<br>2-(5-((3-(1H-indazol-5-ylamino)piperidin-1-yl)methyl)-1H-indol-1-yl)ethanol | 1c, 7, 8, 9, 10, 13, 16c |
| 1.115 | 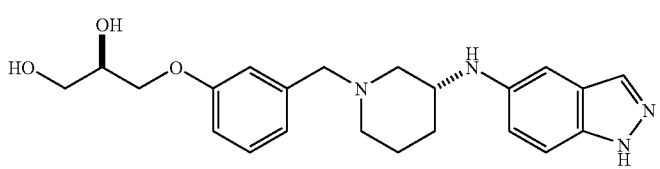<br>(R)-3-(3-(((R)-3-(1H-indazol-5-ylamino)piperidin-1-yl)methyl)phenoxy)propane-1,2-diol | 1c, 7, 8, 9, 10, 12a, 15c, 15d |
| 1.116 | 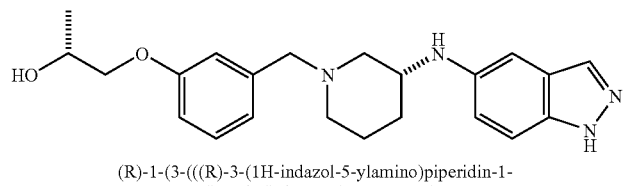<br>(R)-1-(3-(((R)-3-(1H-indazol-5-ylamino)piperidin-1-yl)methyl)phenoxy)propan-2-ol | 1c, 7, 8, 9, 10, 12a, 15c, 15d |
| 1.117 | 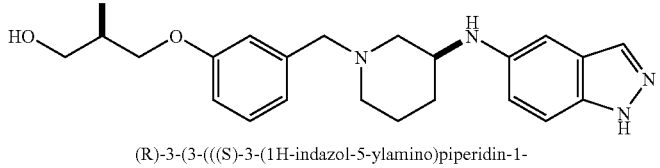<br>(R)-3-(3-(((S)-3-(1H-indazol-5-ylamino)piperidin-1-yl)methyl)phenoxy)propane-1,2-diol | 1c, 7, 8, 9, 10, 12a, 15c, 15d |
| 1.118 | 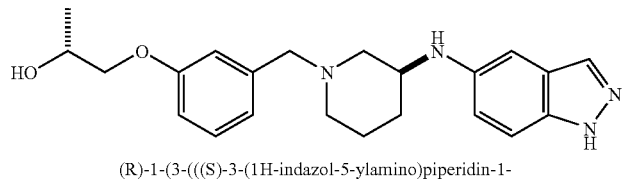<br>(R)-1-(3-(((S)-3-(1H-indazol-5-ylamino)piperidin-1-yl)methyl)phenoxy)propan-2-ol | 1c, 7, 8, 9, 10, 12a, 15c, 15d |
| 1.119 | 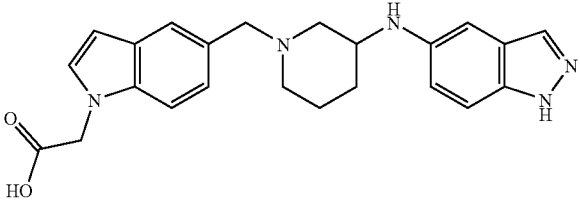<br>2-(5-((3-(1H-indazol-5-ylamino)piperidin-1-yl)methyl)-1H-indol-1-yl)acetic acid | 1c, 7, 8, 9, 10, 13, 16c |
| 1.120 | 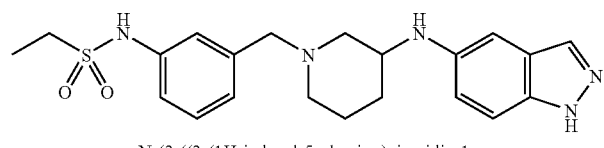<br>N-(3-((3-(1H-indazol-5-ylamino)piperidin-1-yl)methyl)phenyl)ethanesulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.121 | N-(3-((3-(1H-indazol-5-ylamino)piperidin-1-yl)methyl)phenyl)-N-methylmethanesulfonamide | 1c, 7, 8, 9, 10, 12a, 15c, 15d |
| 1.122 | N-(3-((3-(1H-indazol-5-ylamino)piperidin-1-yl)methyl)benzyl)acetamide | 1c, 7, 8, 9, 10, 13, 16c |
| 1.123 | (R)-N-(3-((3-(1H-indazol-5-ylamino)piperidin-1-yl)methyl)phenyl)ethanesulfonamide | 1c, 7, 8, 9, 10, 12a, 15c, 15d |
| 1.124 | (S)-N-(3-((3-(1H-indazol-5-ylamino)piperidin-1-yl)methyl)phenyl)ethanesulfonamide | 1c, 7, 8, 9, 10, 12a, 15c, 15d |
| 1.125 | (R)-2-(3-((3-(1H-indazol-5-ylamino)piperidin-1-yl)methyl)phenoxy)acetic acid | 1c, 7, 8, 9, 10, 12a, 15c, 15d |
| 1.126 | (R)-2-(3-((3-(1H-indazol-5-ylamino)piperidin-1-yl)methyl)phenoxy)-N-(pyridin-3-yl)acetamide | 1c, 7, 8, 9, 10, 12a, 15c, 15d |
| 1.127 | (R)-2-(3-((3-(1H-indazol-5-ylamino)piperidin-1-yl)methyl)phenoxy)-1-morpholinoethanone | 1c, 7, 8, 9, 10, 12a, 15c, 15d |

TABLE A-continued

Exemplified Compounds.

| Compound | Structure | Select Embodiments 1-16 |
|---|---|---|
| 1.128 | (R)-2-(3-((3-(1H-indazol-5-ylamino)piperidin-1-yl)methyl)phenoxy)-1-(4-methylpiperazin-1-yl)ethanone | 1c, 7, 8, 9, 10, 12a, 15c, 15d |
| 1.129 | (R)-diethyl (3-((3-(1H-indazol-5-ylamino)piperidin-1-yl)methyl)phenoxy)methylphosphonate | 1c, 7, 8, 9, 10, 12a, 15c, 15d |
| 1.130 | 2-(3-((4-(1H-indazol-5-ylamino)piperidin-1-yl)methyl)phenoxy)ethanol | 1c, 7, 8, 9, 10, 12a, 15c, 15d |
| 1.131 | (R)-N-(1-(benzofuran-5-ylmethyl)piperidin-3-yl)-1H-indazol-5-amine | 1c, 7, 8, 9, 10 |
| 1.132 | (R)-N-(1-(4-chlorobenzyl)piperidin-3-yl)-1H-indazol-5-amine | 1c, 7, 8, 9, 10 |
| 1.133 | (R)-N-(1-(4-methylbenzyl)piperidin-3-yl)-1H-indazol-5-amine | 1c, 7, 8, 9, 10 |
| 1.134 | (R)-N-(1-(4-bromobenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.136 | (R)-N-(1-(4-ethylbenzyl)piperidin-3-yl)-1H-indazol-5-amine | 1c, 7, 8, 9, 10 |
| 1.137 | (R)-N-(1-(2,4-dimethylbenzyl)piperidin-3-yl)-1H-indazol-5-amine | 1c, 7, 8, 9, 10 |
| 1.138 | (R)-N-(1-(benzo[b]thiophen-5-ylmethyl)piperidin-3-yl)-1H-indazol-5-amine | 1c, 7, 8, 9, 10 |
| 1.139 | (R)-N-(1-(3-(methylsulfonylmethyl)benzyl)piperidin-3-yl)-1H-indazol-5-amine | 1c, 7, 8, 9, 10, 12, 15c |
| 1.140 | (R)-tert-butyl 3-((3-(1H-indazol-5-ylamino)piperidin-1-yl)methyl)benzylcarbamate | 1c, 7, 8, 9, 10, 13, 16c |
| 1.141 | (S)-N-(1-(4-chlorobenzyl)piperidin-3-yl)-1H-indazol-5-amine | 1c, 7, 8, 9, 10 |
| 1.142 | (S)-N-(1-(4-bromobenzyl)piperidin-3-yl)-1H-indazol-5-amine | 1c, 7, 8, 9, 10 |
| 1.143 | (R)-N-(1-((1H-indol-5-yl)methyl)piperidin-3-yl)-1H-indazol-5-amine | 1c, 7, 8, 9, 10, 13, 16c |

TABLE A-continued

Exemplified Compounds.

| Compound | Structure | Select Embodiments 1-16 |
|---|---|---|
| 1.144 | 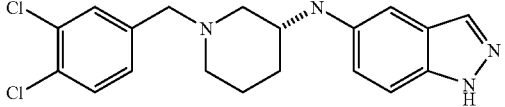<br>(R)-N-(1-(3,4-dichlorobenzyl)piperidin-3-yl)-1H-indazol-5-amine | 1c, 7, 8, 9, 10 |
| 1.145 | 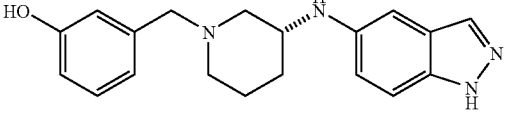<br>(R)-3-((3-(1H-indazol-5-ylamino)piperidin-1-yl)methyl)phenol | 1c, 7, 8, 9, 10 |
| 1.146 | 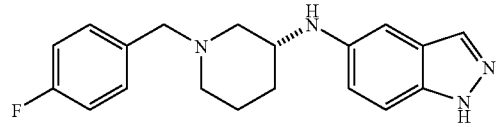<br>(R)-N-(1-(4-fluorobenzyl)piperidin-3-yl)-1H-indazol-5-amine | 1c, 7, 8, 9, 10 |
| 1.147 | 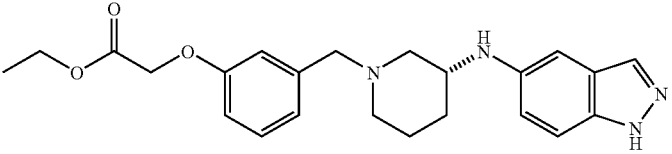<br>(R)-ethyl 2-(3-((3-(1H-indazol-5-ylamino)piperidin-1-yl)methyl)phenoxy)acetate | 1c, 7, 8, 9, 10, 12a, 15c, 15d |
| 1.148 | 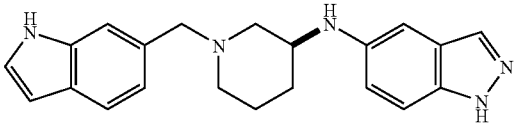<br>(S)-N-(1-((1H-indol-6-yl)methyl)piperidin-3-yl)-1H-indazol-5-amine | 1c, 7, 8, 9, 10 |
| 1.149 | 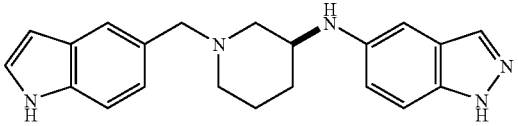<br>(S)-N-(1-((1H-indol-5-yl)methyl)piperidin-3-yl)-1H-indazol-5-amine | 1c, 7, 8, 9, 10 |
| 1.150 | 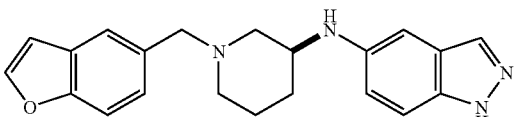<br>(S)-N-(1-(benzofuran-5-ylmethyl)piperidin-3-yl)-1H-indazol-5-amine | 1c, 7, 8, 9, 10 |
| 1.151 | 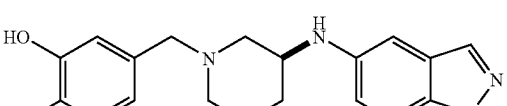<br>(S)-5-((3-(1H-indazol-5-ylamino)piperidin-1-yl)methyl)-2-methylphenol | 1c, 7, 8, 9, 10 |

TABLE A-continued

Exemplified Compounds.

| Compound | Structure | Select Embodiments 1-16 |
|---|---|---|
| 1.152 | 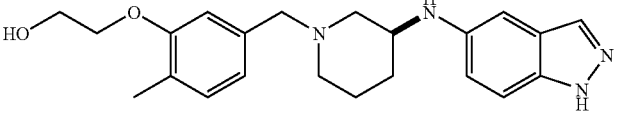<br>(S)-2-(5-((3-(1H-indazol-5-ylamino)piperidin-1-yl)methyl)-2-methylphenoxy)ethanol | 1c, 7, 8, 9, 10, 12a, 15c, 15d |
| 1.153 | 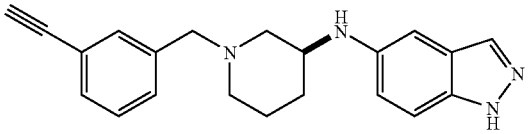<br>(S)-N-(1-(3-ethynylbenzyl)piperidin-3-yl)-1H-indazol-5-amine | 1c, 7, 8, 9, 10, 11, 14c |
| 1.154 | 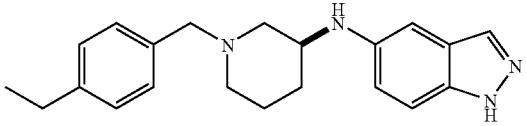<br>(S)-N-(1-(4-ethylbenzyl)piperidin-3-yl)-1H-indazol-5-amine | 1c, 7, 8, 9, 10 |
| 1.155 | 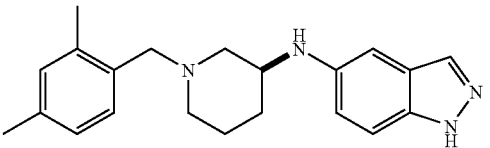<br>(S)-N-(1-(2,4-dimethylbenzyl)piperidin-3-yl)-1H-indazol-5-amine | 1c, 7, 8, 9, 10 |
| 1.156 | 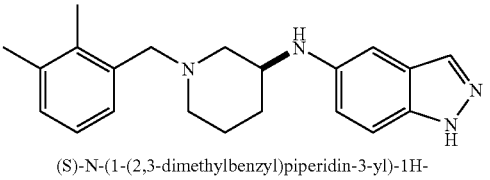<br>(S)-N-(1-(2,3-dimethylbenzyl)piperidin-3-yl)-1H-indazol-5-amine | 1c, 7, 8, 9, 10 |
| 1.157 | 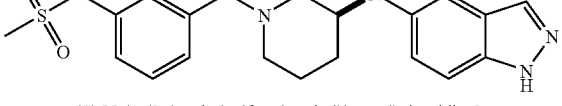<br>(S)-N-(1-(3-(methylsulfonylmethyl)benzyl)piperidin-3-yl)-1H-indazol-5-amine | 1c, 7, 8, 9, 10, 12, 15c |
| 1.158 | 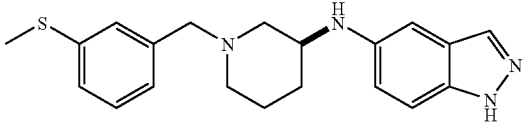<br>(S)-N-(1-(3-(methylthio)benzyl)piperidin-3-yl)-1H-indazol-5-amine | 1c, 7, 8, 9, 10, 12b, 15c, 15e |
| 1.159 | 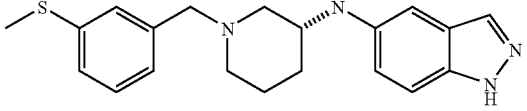<br>(R)-N-(1-(3-(methylthio)benzyl)piperidin-3-yl)-1H-indazol-5-amine | 1c, 7, 8, 9, 10, 12b, 15c, 15e |

TABLE A-continued

Exemplified Compounds.

| Compound | Structure | Select Embodiments 1-16 |
|---|---|---|
| 1.160 | (R)-N-(1-(3-(methylsulfonyl)benzyl)piperidin-3-yl)-1H-indazol-5-amine | 1c, 7, 8, 9, 10, 12, 15c |
| 1.161 | (R)-2-(5-((3-(1H-indazol-5-ylamino)piperidin-1-yl)methyl)-2-methylphenoxy)ethanol | 1c, 7, 8, 9, 10, 12a, 15c, 15d |
| 1.162 | (R)-2-(5-((3-(1H-indazol-5-ylamino)piperidin-1-yl)methyl)-1H-indol-1-yl)acetamide | 1c, 7, 8, 9, 10, 13, 16c |
| 1.163 | (S)-3-((3-(1H-indazol-5-ylamino)piperidin-1-yl)methyl)phenol | 1c, 7, 8, 9, 10 |
| 1.164 | (S)-N-(1-(4-fluorobenzyl)piperidin-3-yl)-1H-indazol-5-amine | 1c, 7, 8, 9, 10 |
| 1.165 | (S)-2-(5-((3-(1H-indazol-5-ylamino)piperidin-1-yl)methyl)-1H-indol-1-yl)acetamide | 1c, 7, 8, 9, 10, 13, 16c |
| 1.166 | (S)-N-(1-((2,3-dihydrobenzo[b][1,4]dioxin-6-yl)methyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.167 | (S)-N-(1-(4-(trifluoromethyl)benzyl)piperidin-3-yl)-1H-indazol-5-amine | 1c, 7, 8, 9, 10 |
| 1.168 | (S)-N-(1-(4-(ethylthio)benzyl)piperidin-3-yl)-1H-indazol-5-amine | 1C, 7, 8, 9, 10, 12b, 15c, 15e |
| 1.169 | (S)-N-(1-(3-(trifluoromethyl)benzyl)piperidin-3-yl)-1H-indazol-5-amine | 1c, 7, 8, 9, 10 |
| 1.170 | (S)-N-(1-(3-chlorobenzyl)piperidin-3-yl)-1H-indazol-5-amine | 1c, 7, 8, 9, 10 |
| 1.171 | (S)-N-(1-(3-methylbenzyl)piperidin-3-yl)-1H-indazol-5-amine | 1.171 |
| 1.172 | (R)-N-(1-(2,3-dimethylbenzyl)piperidin-3-yl)-1H-indazol-5-amine | 1.172 |
| 1.173 | (R)-5-((3-(1H-indazol-5-ylamino)piperidin-1-yl)methyl)-2-methylphenol | 1.173 |
| 1.174 | (R)-2-(3-((3-(1H-indazol-5-ylamino)piperidin-1-yl)methyl)phenoxy)acetamide | 1.174 |

TABLE A-continued

Exemplified Compounds.

| Compound | Structure | Select Embodiments 1-16 |
|---|---|---|
| 1.175 | (S)-N-(1-(benzo[b]thiophen-5-ylmethyl)piperidin-3-yl)-1H-indazol-5-amine | 1.175 |
| 1.176 | (S)-tert-butyl 3-((3-(1H-indazol-5-ylamino)piperidin-1-yl)methyl)benzylcarbamate | 1.176 |
| 1.177 | (R)-N-(1-((2,3-dihydrobenzo[b][1,4]dioxin-6-yl)methyl)piperidin-3-yl)-1H-indazol-5-amine | 1.177 |
| 1.178 | (R)-N-(1-(4-(trifluoromethyl)benzyl)piperidin-3-yl)-1H-indazol-5-amine | 1.178 |
| 1.179 | (S)-N-(1-(3-ethoxybenzyl)piperidin-3-yl)-1H-indazol-5-amine | 1.179 |
| 1.180 | (S)-N-(1-(4-isopropylbenzyl)piperidin-3-yl)-1H-indazol-5-amine | 1.180 |
| 1.181 | (S)-N-(1-(4-(methylsulfonyl)benzyl)piperidin-3-yl)-1H-indazol-5-amine | 1.181 |

TABLE A-continued

Exemplified Compounds.

| Compound | Structure | Select Embodiments 1-16 |
|---|---|---|
| 1.182 | 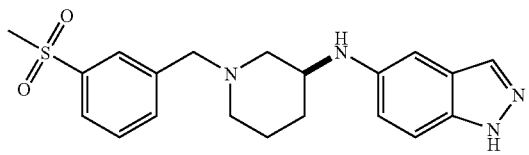<br>(S)-N-(1-(3-(methylsulfonyl)benzyl)piperidin-3-yl)-1H-indazol-5-amine | 1.182 |
| 1.183 | 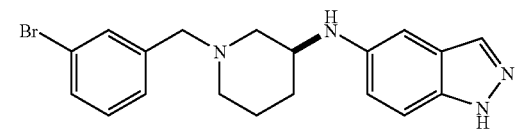<br>(S)-N-(1-(3-bromobenzyl)piperidin-3-yl)-1H-indazol-5-amine | 1.183 |
| 1.184 | 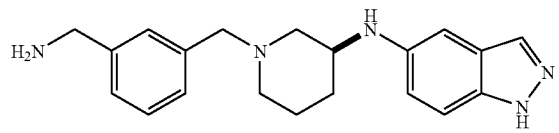<br>(S)-N-(1-(3-(aminomethyl)benzyl)piperidin-3-yl)-1H-indazol-5-amine | 1.184 |
| 1.185 | 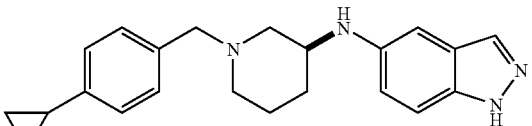<br>(S)-N-(1-(4-cyclopropylbenzyl)piperidin-3-yl)-1H-indazol-5-amine | 1.185 |
| 1.186 | 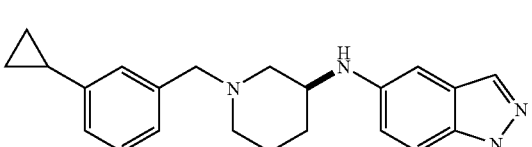<br>(S)-N-(1-(3-cyclopropylbenzyl)piperidin-3-yl)-1H-indazol-5-amine | 1.186 |
| 1.187 | 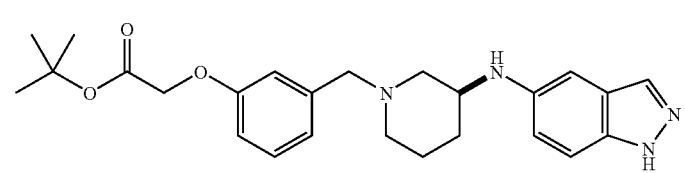<br>(S)-tert-butyl 2-(3-((3-(1H-indazol-5-ylamino)piperidin-1-yl)methyl)phenoxy)acetate | 1.187 |
| 1.188 | 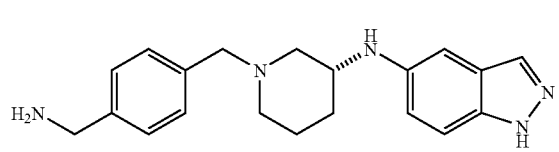<br>(R)-N-(1-(4-(aminomethyl)benzyl)piperidin-3-yl)-1H-indazol-5-amine | 1.188 |

| Compound | Structure | Select Embodiments 1-16 |
|---|---|---|
| 1.189 | (R)-N-(1-(4-(ethylthio)benzyl)piperidin-3-yl)-1H-indazol-5-amine | 1.189 |
| 1.190 | (R)-N-(1-(3-(trifluoromethyl)benzyl)piperidin-3-yl)-1H-indazol-5-amine | 1.190 |
| 1.191 | (R)-N-(1-(3-chlorobenzyl)piperidin-3-yl)-1H-indazol-5-amine | 1c, 7, 8, 9, 10 |
| 1.192 | (R)-N-(1-(3-methylbenzyl)piperidin-3-yl)-1H-indazol-5-amine | 1c, 7, 8, 9, 10 |
| 1.193 | (R)-N-(1-(3-ethynylbenzyl)piperidin-3-yl)-1H-indazol-5-amine | 1c, 7, 8, 9, 10, 11 14c |
| 1.194 | (R)-N-(1H-indazol-5-ylamino)piperidin-1-yl)methyl)benzyl)acetamide | 1c, 7, 8, 9, 10, 13, 16c |
| 1.195 | (S)-2-(3-((3-(1H-indazol-5-ylamino)piperidin-1-yl)methyl)phenyl-1H-indazol-5-ylamino)piperidin-1-yl)methyl)phenoxy)acetamide | 1c, 7, 8, 9, 10, 12a, 15c, 15d |

TABLE A-continued

Exemplified Compounds.

| Compound | Structure | Select Embodiments 1-16 |
|---|---|---|
| 1.196 | 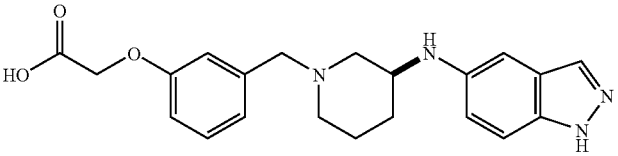<br>(S)-2-(3-((3-(1H-indazol-5-ylamino)piperidin-1-yl)methyl)phenoxy)acetic acid | 1c, 7, 8, 9, 10, 12a, 15c, 15d |
| 1.197 | 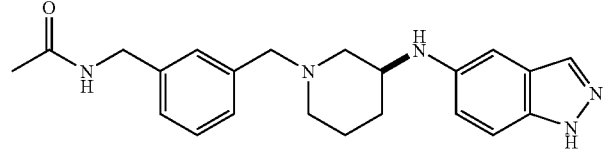<br>(S)-N-(1H-indazol-5-ylamino)piperidin-1-yl)methyl)benzyl)acetamide | 1c, 7, 8, 9, 10, 13, 16c |
| 1.198 | 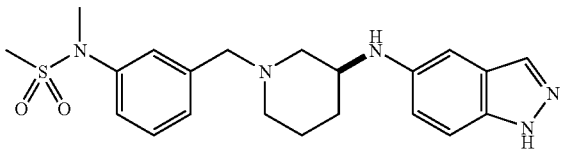<br>(S)-N-(3-((3-(1H-indazol-5-ylamino)piperidin-1-yl)methyl)phenyl)-N-methylmethanesulfonamide | 1c, 7, 8, 9, 10, 12a, 15c, 15d |
| 1.199 | 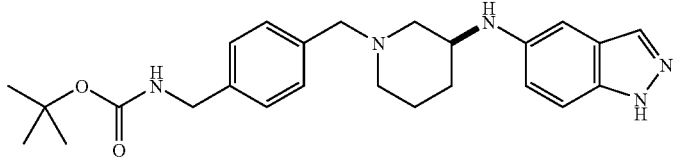<br>(S)-tert-butyl 4-((3-(1H-indazol-5-ylamino)piperidin-1-yl)methyl)benzylcarbamate | 1c, 7, 8, 9, 10, 13, 16c |
| 1.200 | 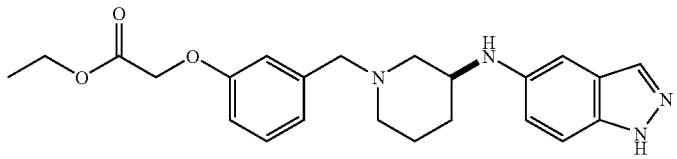<br>(S)-ethyl 2-(3-((3-(1H-indazol-5-ylamino)piperidin-1-yl)methyl)phenoxy)acetate | 1c, 7, 8, 9, 10, 12a, 15c, 15d |
| 1.201 | 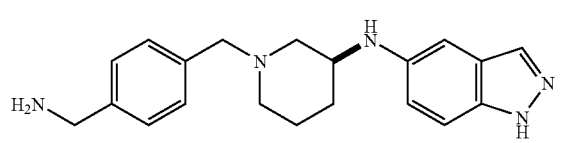<br>(S)-N-(1-(4-(aminomethyl)benzyl)piperidin-3-yl)-1H-indazol-5-amine | 1c, 7, 8, 9, 10, 13, 16c |
| 1.202 | 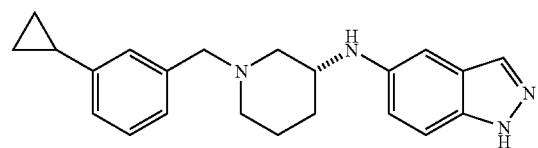<br>(R)-N-(1-(3-cyclopropylbenzyl)piperidin-3-yl)-1H-indazol-5-amine | 1c, 7, 8, 9, 10, 11, 14c |

TABLE A-continued

Exemplified Compounds.

| Compound | Structure | Select Embodiments 1-16 |
|---|---|---|
| 1.203 | (R)-N-(1-(3-ethoxybenzyl)piperidin-3-yl)-1H-indazol-5-amine | 1c, 7, 8, 9, 10 |
| 1.204 | (R)-N-(1-(4-isopropylbenzyl)piperidin-3-yl)-1H-indazol-5-amine | 1c, 7, 8, 9, 10 |
| 1.205 | (R)-N-(1-(4-methylsulfonyl)benzyl)piperidin-3-yl)-1H-indazol-5-amine | 1c, 7, 8, 9, 10, 12, 15c |
| 1.206 | (R)-N-(1-(4-cyclopropylbenzyl)piperidin-3-yl)-1H-indazol-5-amine | 1c, 7, 8, 9, 10, 11, 14c |
| 1.207 | (R)-N-(3-((3-(1H-indazol-5-ylamino)piperidin-1-yl)methyl)phenyl)-N-methylmethanesulfonamide | 1c, 7, 8, 9, 10, 12a, 15c, 15d |
| 1.208 | (R)-N-(1-(4-vinylbenzyl)piperidin-3-yl)-1H-indazol-5-amine | 1c, 7, 8, 9, 10, 11, 14c |
| 1.209 | (R)-ethyl 4-((3-(1H-indazol-5-ylamino)piperidin-1-yl)methyl)benzoate | 1c, 7, 8, 9, 10 |

TABLE A-continued

Exemplified Compounds.

| Compound | Structure | Select Embodiments 1-16 |
|---|---|---|
| 1.210 | (R)-N-(1-(3-bromobenzyl)piperidin-3-yl)-1H-indazol-5-amine | 1c, 7, 8, 9, 10 |
| 1.211 | (R)-N-(2-(3-((3-(1H-indazol-5-ylamino)piperidin-1-yl)methyl)phenoxy)ethyl)acetamide | 1c, 7, 8, 9, 10, 12a, 15c, 15d |
| 1.212 | (R)-N-(5-((3-(1H-indazol-5-ylamino)piperidin-1-yl)methyl)-2-chlorophenyl)methanesulfonamide | 1c, 7, 8, 9, 10, 12a, 15c, 15d |
| 1.213 | (S)-N-(5-((3-(1H-indazol-5-ylamino)piperidin-1-yl)methyl)-2-chlorophenyl)methanesulfonamide | 1c, 7, 8, 9, 10, 12a, 15c, 15d |
| 1.214 | N-((S)-1-(3-(((S)-2,2-dimethyl-1,3-dioxolan-4-yl)methoxy)benzyl)piperidin-3-yl)-1H-indazol-5-amine | 1c, 7, 8, 9, 10, 12a, 15c, 15d |
| 1.215 | (S)-3-((3-(1H-indazol-5-ylamino)piperidin-1-yl)methyl)benzenesulfonamide | 1c, 7, 8, 9, 10, 12, 15c |
| 1.216 | (S)-ethyl 4-((3-(1H-indazol-5-ylamino)piperidin-1-yl)methyl)benzoate | 1c, 7, 8, 9, 10 |

US 8,207,195 B2

85 86

TABLE A-continued

Exemplified Compounds.

| Compound | Structure | Select Embodiments 1-16 |
|---|---|---|
| 1.217 | 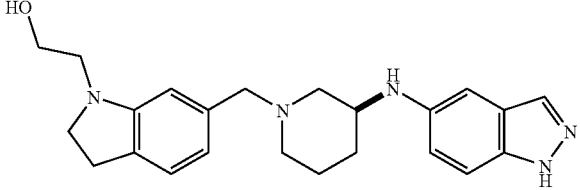<br>(S)-2-(6-((3-(1H-indazol-5-ylamino)piperidin-1-yl)methyl)indolin-1-yl)ethanol | 1c, 7, 8, 9, 10, 13, 16c |
| 1.218 | 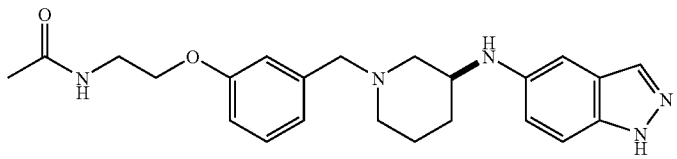<br>(S)-N-(2-(3-((3-(1H-indazol-5-ylamino)piperidin-1-yl)methyl)phenoxy)ethyl)acetamide | 1c, 7, 8, 9, 10, 12a, 15c, 15d |
| 1.219 | 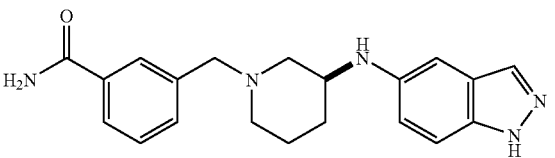<br>(S)-3-((3-(1H-indazol-5-ylamino)piperidin-1-yl)methyl)benzamide | 1c, 7, 8, 9, 10, 12, 15c |
| 1.221 | 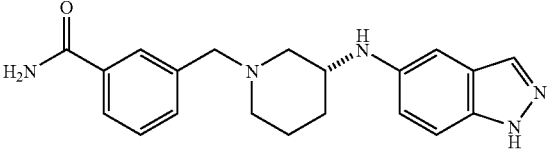<br>(R)-3-((3-(1H-indazol-5-ylamino)piperidin-1-yl)methyl)benzamide | 1c, 7, 8, 9, 10, 12, 15c |
| 1.222 | 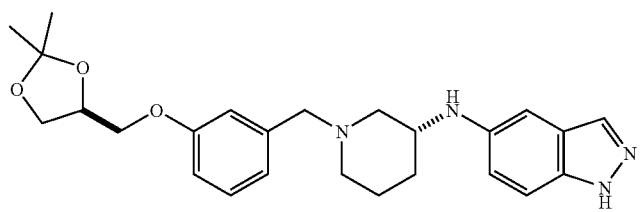<br>N-((R)-1-(3-(((S)-2,2-dimethyl-1,3-dioxolan-4-yl)methoxy)benzyl)piperidin-3-yl)-1H-indazol-5-amine | 1c, 7, 8, 9, 10,12a, 15c, 15d |
| 1.223 | 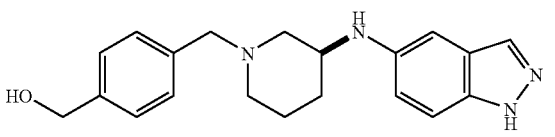<br>(S)-(4-((3-(1H-indazol-5-ylamino)piperidin-1-yl)methyl)phenyl)methanol | 1c, 7, 8, 9, 10, 13, 16c |
| 1.224 | 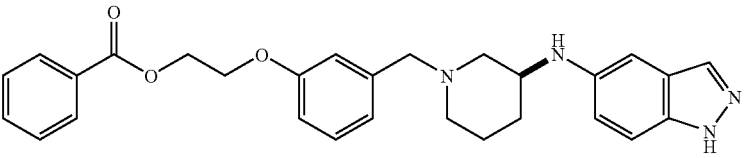<br>(S)-2-(3-((3-(1H-indazol-5-ylamino)piperidin-1-yl)methyl)phenoxy)ethyl benzoate | 1c, 7, 8, 9, 10, 12a, 15c, 15d |

TABLE A-continued

Exemplified Compounds.

| Compound | Structure | Select Embodiments 1-16 |
|---|---|---|
| 1.225 | 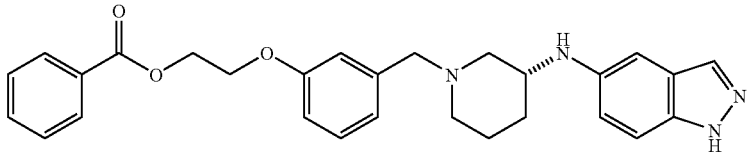<br>(R)-2-(3-((3-(1H-indazol-5-ylamino)piperidin-1-yl)methyl)phenoxy)methyl)ethyl benzoate | 1c, 7, 8, 9, 10, 12a, 15c, 15d |
| 1.226 | 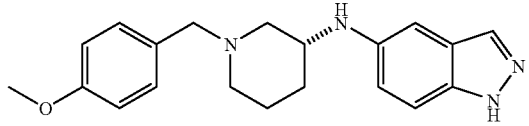<br>(R)-N-(1-(4-methoxybenzyl)piperidin-3-yl)-1H-indazol-5-amine | 1c, 7, 8, 9, 10 |
| 1.227 | 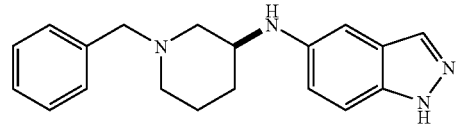<br>(S)-N-(1-benzylpiperidin-3-yl)-1H-indazol-5-amine | 1c, 7, 8, 9, 10 |
| 1.228 | 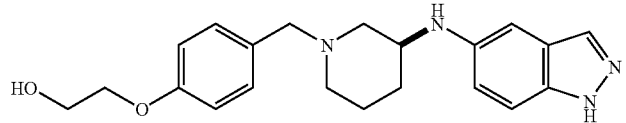<br>(S)-2-(4-((3-(1H-indazol-5-ylamino)piperidin-1-yl)methyl)phenoxy)ethanol | 1c, 7, 8, 9, 10, 12a, 15c, 15d |
| 1.229 | 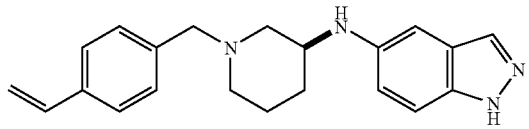<br>(S)-N-(1-(4-vinylbenzyl)piperidin-3-yl)-1H-indazol-5-amine | 1c, 7, 8, 9, 10, 11, 14c |
| 1.230 | 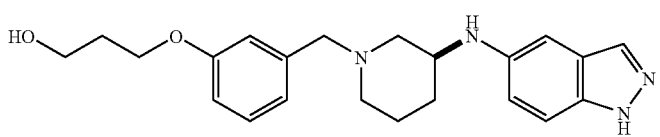<br>(S)-3-(3-((3-(1H-indazol-5-ylamino)piperidin-1-yl)methyl)phenoxy)propan-1-ol | 1c, 7, 8, 9, 10, 12a, 15c, 15d |
| 1.231 | 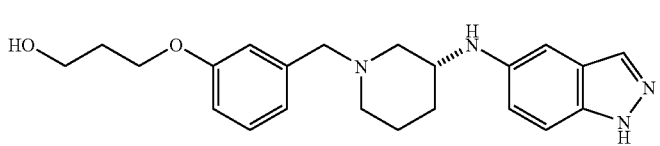<br>(R)-3-(3-((3-(1H-indazol-5-ylamino)piperidin-1-yl)methyl)phenoxy)propan-1-ol | 1c, 7, 8, 9, 10, 12a, 15c, 15d |
| 1.232 | 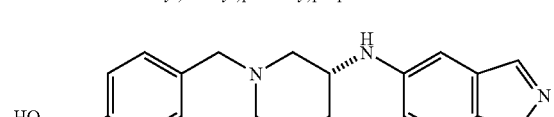<br>(R)-(4-((3-(1H-indazol-5-ylamino)piperidin-1-yl)methyl)phenyl)methanol | 1c, 7, 8, 9, 10 |

TABLE A-continued

Exemplified Compounds.

| Compound | Structure | Select Embodiments 1-16 |
|---|---|---|
| 1.233 | (S)-N-(5-((3-1H-indazol-5-ylamino)piperidin-1-yl)methyl)-2-methylphenyl)methanesulfonamide | 1c, 7, 8, 9, 10, 12a, 15c, 15d |
| 1.234 | (S)-N-(5-((3-(1H-indazol-5-ylamino)piperidin-1-yl)methyl)-2-methoxyphenyl)methanesulfonamide | 1c, 7, 8, 9, 10, 12a, 15c, 15d |
| 1.235 | (R)-N-(1-(3-(aminomethyl)benzyl)piperidin-3-yl)-1H-indazol-5-amine | 1c, 7, 8, 9, 10, 13, 16c |
| 1.236 | (S)-N-(5-((3-(1H-indazol-5-ylamino)piperidin-1-yl)methyl)-2-methylphenyl)butane-1-sulfonamide | 1c, 7, 8, 9, 10, 12a, 15c, 15d |
| 1.237 | (S)-N-(2-((3-(1H-indazol-5-ylamino)piperidin-1-yl)methyl)-5-methylphenyl)-N',N' dimethylaminosulfamide | 1c, 7, 8, 9, 10, 12a, 15c, 15d |
| 1.238 | (S)-N-(5-((3-(1H-indazol-5-ylamino)piperidin-1-yl)methyl)-2-methylphenyl)propane-1-sulfonamide | 1c, 7, 8, 9, 10, 12a, 15c, 15d |
| 1.239 | (S)-N-(5-((3-(1H-indazol-5-ylamino)piperidin-1-yl)methyl)-2-methylphenyl)-4-methylbenzenesulfonamide | 1c, 7, 8, 9, 10, 12a, 15c, 15d |

US 8,207,195 B2

TABLE A-continued

Exemplified Compounds.

| Compound | Structure | Select Embodiments 1-16 |
|---|---|---|
| 1.240 | 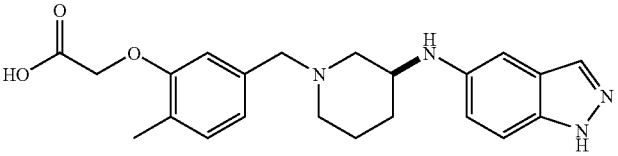<br>(S)-2-(5-((3-(1H-indazol-5-ylamino)piperidin-1-yl)methyl)-2-methylphenyl-1H-indazol-5-ylamino)piperidin-1-yl)methyl)-2-methylphenoxy)acetic acid | 1c, 7, 8, 9, 10, 12a, 15c, 15d |
| 1.241 | 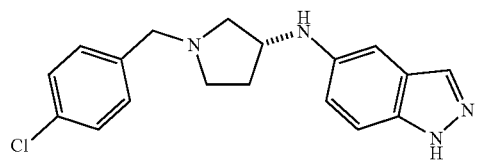<br>(R)-N-(1-(4-chlorobenzyl)pyrrolidin-3-yl)-1H-indazol-5-amine | 1c, 7, 8, 9, 10 |
| 1.242 | 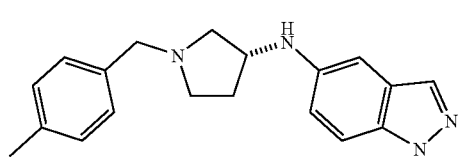<br>(R)-N-(1-(4-methylbenzyl)pyrrolidin-3-yl)-1H-indazol-5-amine | 1c, 7, 8, 9, 10 |
| 1.243 | 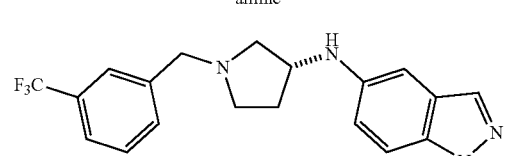<br>(R)-N-(1-(3-(trifluoromethyl)benzyl)pyrrolidin-3-yl)-1H-indazol-5-amine | 1c, 7, 8, 9, 10 |
| 1.244 | 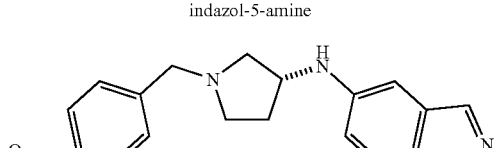<br>(R)-N-(1-(4-(methylsulfonyl)benzyl)pyrrolidin-3-yl)-1H-indazol-5-amine | 1c, 7, 8, 9, 10, 12b, 15c, 15e |
| 1.245 | 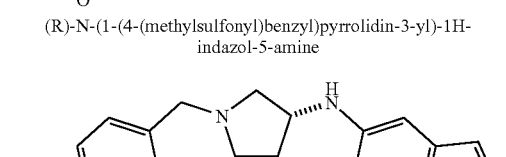<br>(R)-N-(1-(4-methoxybenzyl)pyrrolidin-3-yl)-1H-indazol-5-amine | 1c, 7, 8, 9, 10 |
| 1.246 | 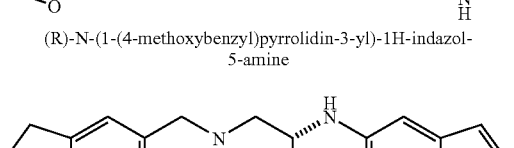<br>(R)-N-(1-((2,3-dihydrobenzofuran-5-yl)methyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.247 | (R)-N-(1-(pyridin-4-ylmethyl)piperidin-3-yl)-1H-indazol-5-amine | 1c, 7, 8, 9, 10 |
| 1.248 | (R)-N-(1-(4-(pyrrolidin-1-yl)benzyl)piperidin-3-yl)-1H-indazol-5-amine | 1c, 7, 8, 9, 10, 11, 14c |
| 1.249 | (R)-3-((3-(1H-indazol-5-ylamino)piperidin-1-yl)methyl)benzenesulfonamide | 1c, 7, 8, 9, 10, 12b, 15c, 15e |
| 1.250 | (R)-N-(1-(3-(furan-2-yl)benzyl)piperidin-3-yl)-1H-indazol-5-amine | 1c, 7, 8, 9, 10, 11, 14c |
| 1.251 | N-((3R)-1-(2-phenylpropyl)piperidin-3-yl)-1H-indazol-5-amine | 1c, 7, 8, 9 |
| 1.252 | (R)-N-(1-((1H-indol-3-yl)methyl)piperidin-3-yl)-1H-indazol-5-amine | 1c, 7, 8, 9, 10 |
| 1.253 | (S)-N-(5-((3-(1H-indazol-5-ylamino)piperidin-1-yl)methyl)-2-methylphenyl)ethanesulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.254 | (R)-N-(1-(3,4-dichlorobenzyl)pyrrolidin-3-yl)-1H-indazol-5-amine | 1c, 7, 8, 9, 10 |
| 1.255 | (S)-N-(1-(1H-imidazol-1-yl)benzyl)piperidin-3-yl)-1H-indazol-5-amine | 1c, 7, 8, 9, 10, 11, 14c |
| 1.256 | (S)-N-(1-((1H-imidazol-2-yl)methyl)piperidin-3-yl)-1H-indazol-5-amine | 1c, 7, 8, 9, 10 |
| 1.257 | (S)-N-(1-((1-methyl-1H-imidazol-2-yl)methyl)piperidin-3-yl)-1H-indazol-5-amine | 1c, 7, 8, 9, 10 |
| 1.258 | (R)-N-(5-((3-(1H-indazol-5-ylamino)piperidin-1-yl)methyl)-2-methylphenyl)methanesulfonamide | 1c, 7, 8, 9, 10, 12a, 15c, 15d |
| 1.259 | (R)-N-(5-((3-(1H-indazol-5-ylamino)piperidin-1-yl)methyl)-2-methylphenyl)ethanesulfonamide | 1c, 7, 8, 9, 10, 12a, 15c, 15d |
| 1.260 | (R)-N-(5-((3-(1H-indazol-5-ylamino)piperidin-1-yl)methyl)-2-methylphenyl)-4-methylbenzenesulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.261 | 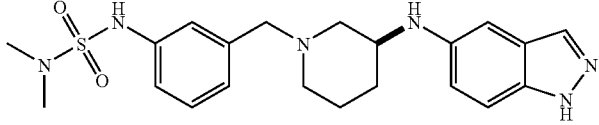  (S)-N-(3-((3-(1H-indazol-5-ylamino)piperidin-1-yl)methyl)phenyl)-N',N'dimethylaminosulfonamide | 1c, 7, 8, 9, 10, 12a, 15c, 15d |
| 1.262 | 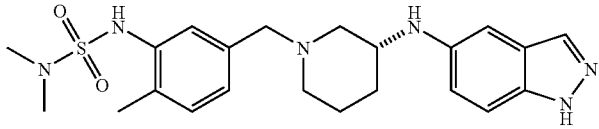  (R)-N-(2-((3-(1H-indazol-5-ylamino)piperidin-1-yl)methyl)-5-methylphenyl)-N',N' dimethylaminosulfamide | 1c, 7, 8, 9, 10, 12a, 15c, 15d |
| 1.263 | 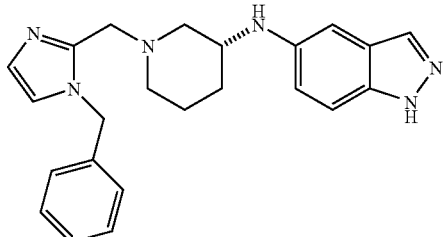  (R)-N-(1-((1-benzyl-1H-imidazol-2-yl)methyl)piperidin-3-yl)-1H-indazol-5-amine | 1c, 7, 8, 9, 10, 11, 14c |
| 1.264 | 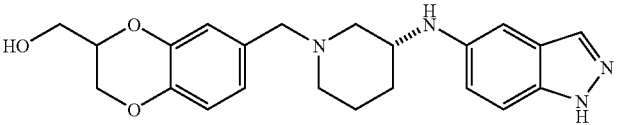  (7-(((R)-3-(1H-indazol-5-ylamino)piperidin-1-yl)methyl)-2,3-dihydrobenzo[b][1,4]dioxin-2-yl)methanol | 1c, 7, 8, 9, 10, 13, 16c |
| 1.265 | 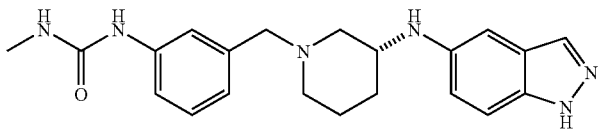  (R)-1-(3-((3-(1H-indazol-5-ylamino)piperidin-1-yl)methyl)phenyl)-3-methylurea | 1c, 7, 8, 9, 10, 12a, 15c, 15d |
| 1.266 | 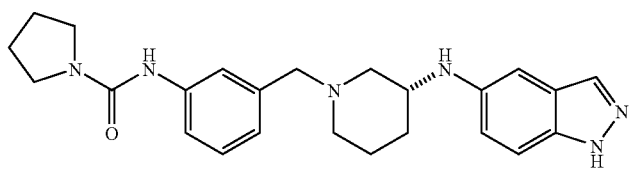  (R)-N-(3-((3-(1H-indazol-5-ylamino)piperidin-1-yl)methyl)phenyl)pyrrolidin-1-carboxamide | 1c, 7, 8, 9, 10, 12a, 15c, 15d |
| 1.267 | 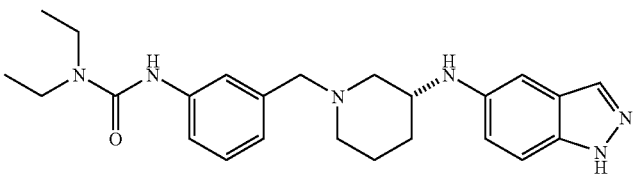  (R)-3-(3-((3-(1H-indazol-5-ylamino)piperidin-1-yl)methyl)phenyl)-1,1-diethylurea | 1c, 7, 8, 9, 10, 12a, 15c, 15d |

TABLE A-continued

Exemplified Compounds.

| Compound | Structure | Select Embodiments 1-16 |
|---|---|---|
| 1.268 | 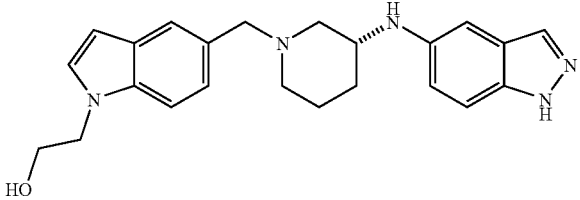<br>(R)-2-(5-((3-(1H-indazol-5-ylamino)piperidin-1-yl)methyl)-1H-indol-1-yl)ethanol | 1c, 7, 8, 9, 10, 13, 16c |
| 1.269 | 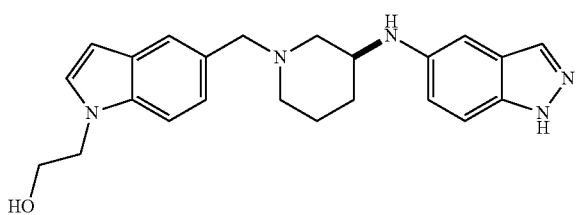<br>(S)-2-(5-((3-(1H-indazol-5-ylamino)piperidin-1-yl)methyl)-1H-indol-1-yl)ethanol | 1c, 7, 8, 9, 10, 13, 16c |
| 1.270 | 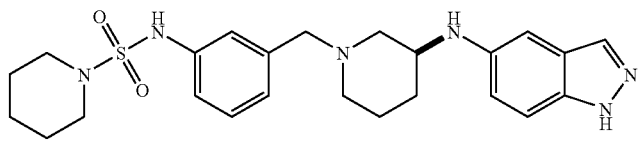<br>(S)-N-(3-((3-(1H-indazol-5-ylamino)piperidin-1-yl)methyl)phenyl)piperidine-1-sulfonamide | 1c, 7, 8, 9, 10, 12a, 15c, 15d |
| 1.271 | 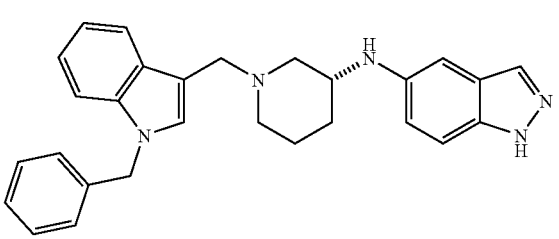<br>(R)-N-(1-((1-benzyl-1H-indol-3-yl)methyl)piperidin-3-yl)-1H-indazol-5-amine | 1c, 7, 8, 9, 10, 11, 14c |
| 1.272 | 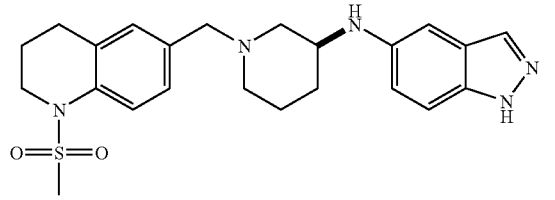<br>(S)-N-(1-((1-(methylsulfonyl)-1,2,3,4-tetrahydroquinolin-6-yl)methyl)piperidin-3-yl)-1H-indazol-5-amine | 1c, 7, 8, 9, 10, 12b, 15c, 15e |
| 1.273 | 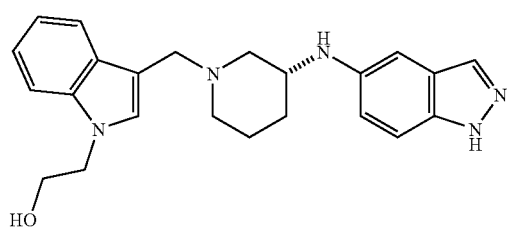<br>(R)-2-(3-((3-(1H-indazol-5-ylamino)piperidin-1-yl)methyl)-1H-indol-1-yl)ethanol | 1c, 7, 8, 9, 10, 13, 16c |

TABLE A-continued

Exemplified Compounds.

| Compound | Structure | Select Embodiments 1-16 |
|---|---|---|
| 1.274 | (S)-N-(3-((3-(1H-indazol-5-ylamino)piperidin-1-yl)methyl)-2-methylphenyl)methanesulfonamide | 1c, 7, 8, 9, 10, 12a, 15c, 15d |
| 1.275 | (S)-N-(3-((3-(1H-indazol-5-ylamino)piperidin-1-yl)methyl)-2-methylphenyl)-N',N'-dimethylaminosulfoamide | 1c, 7, 8, 9, 10, 12a, 15c, 15d |
| 1.276 | (R)-2-(5-((3-(1H-indazol-5-ylamino)pyrrolidin-1-yl)methyl)-2-methylphenyl)-1H-indazol-5-ylamino)pyrrolidin-1-yl)methyl-2-methylphenoxy)ethanol | 1c, 7, 8, 9, 10, 12a, 15c, 15d |
| 1.277 | (S)-N-(1-(thiophen-3-ylmethyl)piperidin-3-yl)-1H-indazol-5-amine | 1c, 7, 8, 9, 10 |
| 1.278 | (S)-N-(1-(thiophen-2-ylmethyl)piperidin-3-yl)-1H-indazol-5-amine | 1c, 7, 8, 9, 10 |
| 1.279 | (S)-N-(1-((2,5-dimethyloxazol-4-yl)methyl)piperidin-3-yl)-1H-indazol-5-amine | 1c, 7, 8, 9, 10 |
| 1.280 | (S)-N-(3-((3-(1H-indazol-5-ylamino)piperidin-1-yl)methyl)-2-methoxyphenyl)methanesulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.281 | (R)-2-(5-((3-(1H-indazol-5-ylamino)piperidin-1-yl)methyl)-2-methylphenyl-1H-indazol-5-ylamino)piperidin-2-yl)methyl)-2-methylphenoxy)acetamide | 1c, 7, 8, 9, 10, 12a, 15c, 15d |
| 1.282 | (S)-2-(5-(3-(1H-indazol-5-ylamino)piperidin-1-yl)methyl)-2-methylphenyl-1H-indazol-5-ylamino)piperidin-1-yl)methyl-2-methylphenoxy)acetamide | 1c, 7, 8, 9, 10, 12a, 15c, 15d |
| 2.001 | N-(1-(4-methoxybenzyl)piperidin-3-yl)isoquinolin-5-amine | 2c, 7, 8, 9, 10 |
| 2.002 | N-(1-(4-(methylsulfonyl)benzyl)piperidin-3-yl)isoquinolin-5-amine | 2c, 7, 8, 9, 10, 12, 15c |
| 2.003 | 3-((3-(isoquinolin-5-ylamino)piperidin-1-yl)methyl)benzonitrile | 2c, 7, 8, 9, 10, 12, 15c |
| 2.004 | N-(4-((3-(isoquinolin-5-ylamino)piperidin-1-yl)methyl)phenyl)acetamide | 2c, 7, 8, 9, 10, 12a, 15c, 15d |

TABLE A-continued

Exemplified Compounds.

| Compound | Structure | Select Embodiments 1-16 |
|---|---|---|
| 2.005 | N-(1-(4-(methylsulfonyl)benzyl)pyrrolidin-3-yl)isoquinolin-5-amine | 2c, 7, 8, 9, 10, 12, 15c |
| 2.006 | N-(1-benzylpyrrolidin-3-yl)isoquinolin-5-amine | 2c, 7, 8, 9, 10 |
| 2.007 | 3-((3-(isoquinolin-5-ylamino)pyrrolidin-1-yl)methyl)benzonitrile | 2c, 7, 8, 9, 10, 12, 15c |
| 2.008 | N-(4-((3-(isoquinolin-5-ylamino)pyrrolidin-1-yl)methyl)phenyl)acetamide | 2c, 7, 8, 9, 10, 12a, 15c, 15d |
| 2.009 | N-(1-(4-(methylthio)benzyl)piperidin-3-yl)isoquinolin-5-amine | 2c, 7, 8, 9, 10, 12b, 15c, 15e |
| 2.010 | N-(1-(4-cyclopropylbenzyl)piperidin-3-yl)isoquinolin-5-amine | 2c, 7, 8, 9, 10, 11, 14c |

TABLE A-continued

Exemplified Compounds.

| Compound | Structure | Select Embodiments 1-16 |
|---|---|---|
| 2.011 | 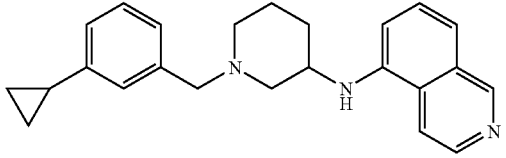<br>N-(1-(3-cyclopropylbenzyl)piperidin-3-yl)isoquinolin-5-amine | 2c, 7, 8, 9, 10, 11, 14c |
| 2.012 | 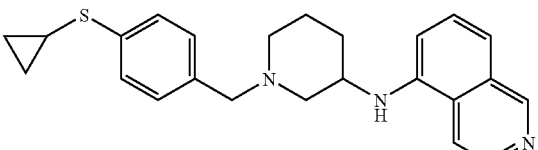<br>N-(1-(4-(cyclopropylthio)benzyl)piperidin-3-yl)isoquinolin-5-amine | 2c, 7, 8, 9, 10, 12b, 15c, 15e |
| 2.013 | 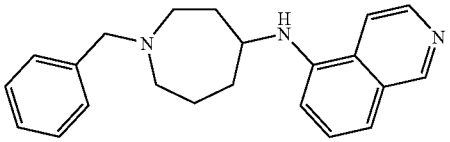<br>N-(1-benzylazepan-4-yl)isoquinolin-5-amine | 2c, 7, 8, 9, 10 |
| 2.014 | 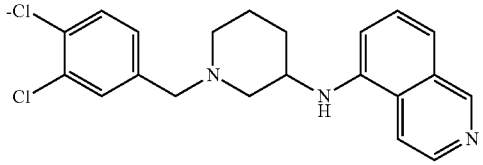<br>N-(1-(3,4-dichlorobenzyl)piperidin-3-yl)isoquinolin-5-amine | 2c, 7, 8, 9, 10 |
| 2.015 | 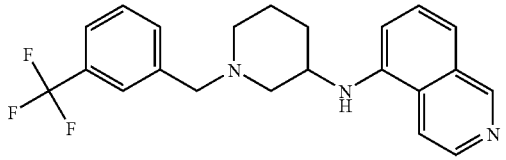<br>N-(1-(3-(trifluoromethyl)benzyl)piperidin-3-yl)isoquinolin-5-amine | 2c, 7, 8, 9, 10 |
| 2.016 | 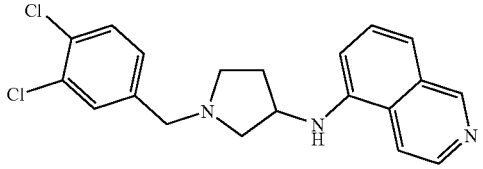<br>N-(1-(3,4-dichlorobenzyl)pyrrolidin-3-yl)isoquinolin-5-amine | 2c, 7, 8, 9, 10 |
| 2.017 | 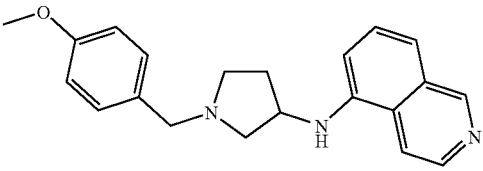<br>N-(1-(4-methoxybenzyl)pyrrolidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.018 | 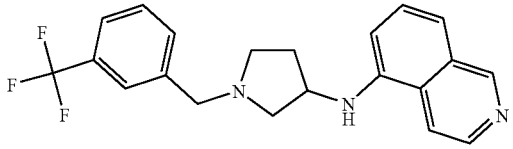<br>N-(1-(3-(trifluoromethyl)benzyl)pyrrolidin-3-yl)isoquinolin-5-amine | 2c, 7, 8, 9, 10 |
| 2.019 | 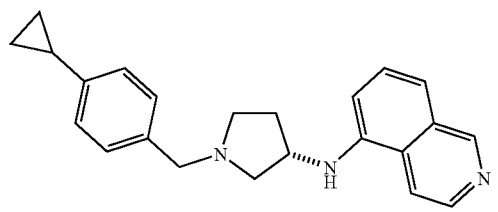<br>(S)-N-(1-(4-cyclopropylbenzyl)pyrrolidin-3-yl)isoquinolin-5-amine | 2c, 7, 8, 9, 10, 11, 14c |
| 2.020 | 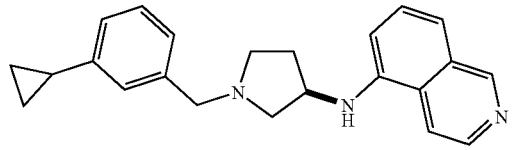<br>(R)-N-(1-(3-cyclopropylbenzyl)pyrrolidin-3-yl)isoquinolin-5-amine | 2c, 7, 8, 9, 10, 11, 14c |
| 2.021 | 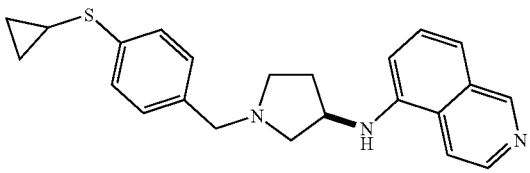<br>(R)-N-(1-(4-(cyclopropylthio)benzyl)pyrrolidin-3-yl)isoquinolin-5-amine | 2c, 7, 8, 9, 10, 12b, 15c, 15e |
| 2.022 | 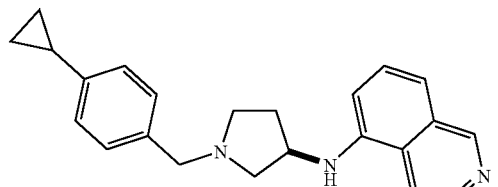<br>(R)-N-(1-(4-cyclopropylbenzyl)pyrrolidin-3-yl)isoquinolin-5-amine | 2c, 7, 8, 9, 10, 11, 14c |
| 2.023 | 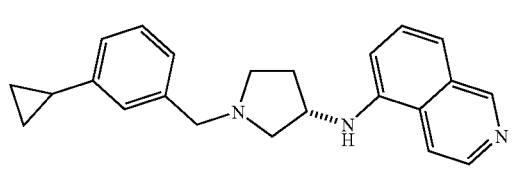<br>(S)-N-(1-(3-cyclopropylbenzyl)pyrrolidin-3-yl)isoquinolin-5-amine | 2c, 7, 8, 9, 10, 11, 14c |

TABLE A-continued

Exemplified Compounds.

| Compound | Structure | Select Embodiments 1-16 |
|---|---|---|
| 2.024 | 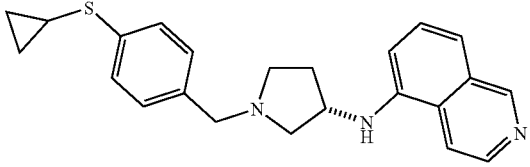<br>(S)-N-(1-(4-(cyclopropylthio)benzyl)pyrrolidin-3-yl)isoquinolin-5-amine | 2c, 7, 8, 9, 10, 12b, 15c, 15e |
| 2.025 | 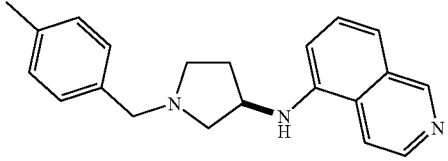<br>(R)-N-(1-(4-methylbenzyl)pyrrolidin-3-yl)isoquinolin-5-amine | 2c, 7, 8, 9, 10 |
| 2.026 | 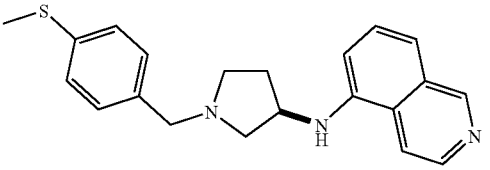<br>(R)-N-(1-(4-(methylthio)benzyl)pyrrolidin-3-yl)isoquinolin-5-amine | 2c, 7, 8, 9, 10, 12b, 15c, 15e |
| 2.027 | 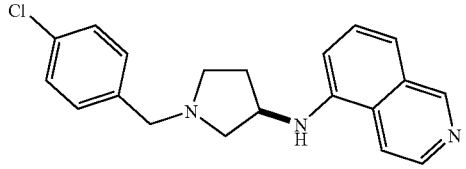<br>(R)-N-(1-(4-chlorobenzyl)pyrrolidin-3-yl)isoquinolin-5-amine | 2c, 7, 8, 9, 10 |
| 2.028 | 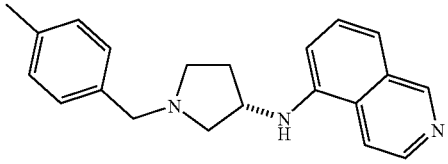<br>(S)-N-(1-(4-methylbenzyl)pyrrolidin-3-yl)isoquinolin-5-amine | 2c, 7, 8, 9, 10 |
| 2.029 | 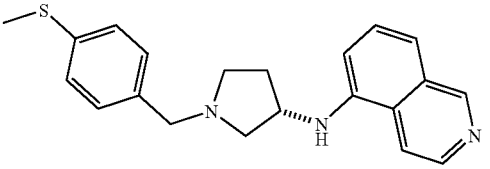<br>(S)-N-(1-(4-(methylthio)benzyl)pyrrolidin-3-yl)isoquinolin-5-amine | 2c, 7, 8, 9, 10, 12b, 15c, 15e |

TABLE A-continued

Exemplified Compounds.

| Compound | Structure | Select Embodiments 1-16 |
|---|---|---|
| 2.030 | (S)-N-(1-(4-chlorobenzyl)pyrrolidin-3-yl)isoquinolin-5-amine | 2c, 7, 8, 9, 10 |
| 2.031 | (R)-N-(1-(4-ethynylbenzyl)pyrrolidin-3-yl)isoquinolin-5-amine | 2c, 7, 8, 9, 10, 11, 14c |
| 2.032 | (S)-2-(3-((3-(isoquinolin-5-ylamino)pyrrolidin-1-yl)methyl)phenoxy)ethanol | 2c, 7, 8, 9, 10, 12a, 15c, 15d |
| 2.033 | (R)-N-(3-((3-(isoquinolin-5-ylamino)piperidin-1-yl)methyl)phenyl)methanesulfonamide | 2c, 7, 8, 9, 10, 12a, 15c, 15d |
| 2.034 | (R)-2-(3-((3-(isoquinolin-5-ylamino)piperidin-1-yl)methyl)phenoxy)ethanol | 2c, 7, 8, 9, 10, 12a, 15c, 15d |
| 2.035 | (S)-N-(3-((3-(isoquinolin-5-ylamino)pyrrolidin-1-yl)methyl)phenyl)methanesulfonamide | 2c, 7, 8, 9, 10, 12a, 15c, 15d |
| 2.036 | (S)-2-(3-((3-(isoquinolin-5-ylamino)piperidin-1-yl)methyl)phenoxy)ethanol | 2c, 7, 8, 9, 10, 12a, 15c, 15d |

TABLE A-continued

Exemplified Compounds.

| Compound | Structure | Select Embodiments 1-16 |
|---|---|---|
| 2.037 | 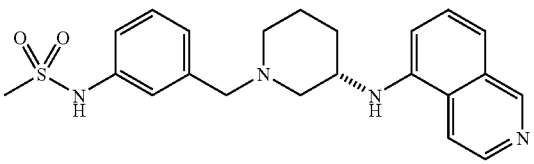

(S)-N-(3-((3-(isoquinolin-5-ylamino)piperidin-1-yl)methyl)phenyl)methanesulfonamide | 2c, 7, 8, 9, 10, 12a, 15c, 15d |
| 2.038 | 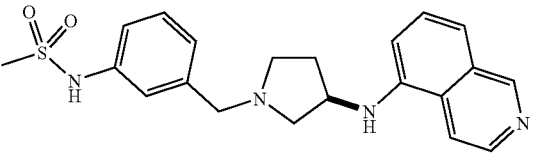

(R)-N-(3-((3-(isoquinolin-5-ylamino)pyrrolidin-1-yl)methyl)phenyl)methanesulfonamide | 2c, 7, 8, 9, 10, 12a, 15c, 15d |
| 2.039 | 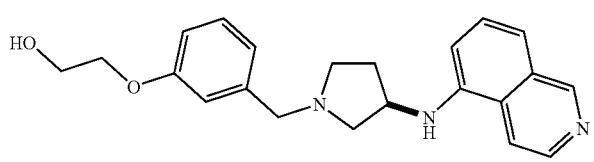

(R)-2-(3-((3-(isoquinolin-5-ylamino)pyrrolidin-1-yl)methyl)phenoxy)ethanol | 2c, 7, 8, 9, 10, 12a, 15c, 15d |
| 2.040 | 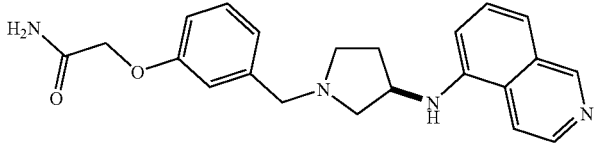

(R)-2-(3-((3-(isoquinolin-5-ylamino)pyrrolidin-1-yl)methyl)phenoxy)acetamide | 2c, 7, 8, 9, 10, 12a, 15c, 15d |
| 2.041 | 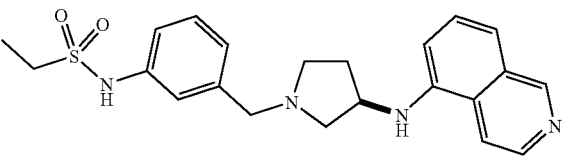

(R)-N-(3-((3-(isoquinolin-5-ylamino)pyrrolidin-1-yl)methyl)phenyl)ethanesulfonamide | 2c, 7, 8, 9, 10, 12a, 15c, 15d |
| 2.042 | 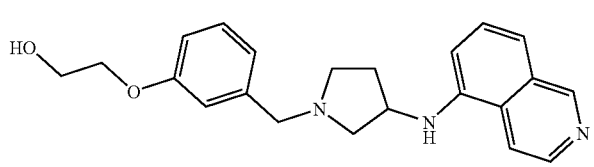

2-(3-((3-(isoquinolin-5-ylamino)pyrrolidin-1-yl)methyl)phenoxy)ethanol | 2c, 7, 8, 9, 10, 12a, 15c, 15d |
| 2.043 | 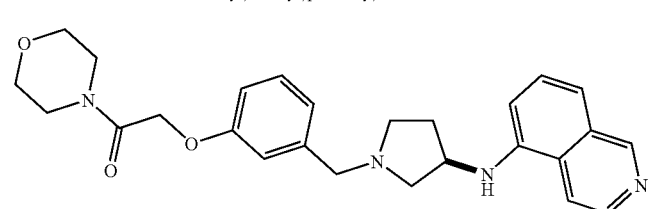

(R)-2-(3-((3-(isoquinolin-5-ylamino)pyrrolidin-1-yl)methyl)phenoxy)-1-morpholinoethanone | 2c, 7, 8, 9, 10, 12a, 15c, 15d |

TABLE A-continued

Exemplified Compounds.

| Compound | Structure | Select Embodiments 1-16 |
|---|---|---|
| 2.044 | (R)-2-(3-((3-(isoquinolin-5-ylamino)pyrrolidin-1-yl)methyl)phenoxy)acetic acid | 2c, 7, 8, 9, 10, 12a, 15c, 15d |
| 2.045 | (S)-N-(1-(4-methylbenzyl)piperidin-3-yl)isoquinolin-5-amine | 2c, 7, 8, 9, 10 |
| 2.046 | (R)-N-(1-benzylpyrrolidin-3-yl)isoquinolin-5-amine | 2c, 7, 8, 9, 10 |
| 2.047 | (R)-N-(1-(4-methoxybenzyl)pyrrolidin-3-yl)isoquinolin-5-amine | 2c, 7, 8, 9, 10 |
| 2.048 | (R)-N-(1-(3,4-dichlorobenzyl)pyrrrolidin-3-yl)isoquinolin-5-amine | 2c, 7, 8, 9, 10 |
| 2.049 | (R)-N-(1-(3-trifluoromethyl)benzyl)pyrrolidin-3-yl)isoquinolin-5-amine | 2c, 7, 8, 9, 10 |
| 2.050 | (S)-N-(1-benzylpiperidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.051 | (S)-N-(1-(4-(methylthio)benzyl)piperidin-3-yl)isoquinolin-5-amine | 2c, 7, 8, 9, 10, 12b, 15c, 15e |
| 2.052 | (S)-N-(1-(4-chlorobenzyl)piperidin-3-yl)isoquinolin-5-amine | 2c, 7, 8, 9, 10 |
| 2.053 | (S)-N-(1-(4-methoxybenzyl)piperidin-3-yl)isoquinolin-5-amine | 2c, 7, 8, 9, 10 |
| 2.054 | (R)-N-(5-((3-(isoquinolin-5-ylamino)pyrrolidin-1-yl)methyl)-2-methylphenyl)ethanesulfonamide | 2c, 7, 8, 9, 10, 12a, 15c, 15d |
| 2.055 | (R)-N-(1-(benzofuran-5-ylmethyl)pyrrolidin-3-yl)isoquinolin-5-amine | 2c, 7, 8, 9, 10 |
| 2.056 | (R)-N-(1-((2,3-dihydrobenzo[b][1,4]dioxin-6-yl)methyl)pyrrolidin-3-yl)isoquinolin-5-amine | 2c, 7, 8, 9, 10 |
| 2.057 | (R)-N-(1-((1H-indol-6-yl)methyl)pyrrolidin-3-yl)isoquinolin-5-amine | 2c, 7, 8, 9, 10 |

TABLE A-continued

Exemplified Compounds.

| Compound | Structure | Select Embodiments 1-16 |
| --- | --- | --- |
| 2.058 | (R)-2-(6-((3-(isoquinolin-5-ylamino)pyrrolidin-1-yl)methyl)-1H-indol-1-yl)acetamide | 2c, 7, 8, 9, 10, 13, 16c |
| 2.059 | (R)-2-(5-((3-(isoquinolin-5-ylamino)pyrrolidin-1-yl)methyl)-1H-indol-1-yl)acetamide | 2c, 7, 8, 9, 10, 13, 16c |
| 2.060 | (R)-2-(6-((3-(isoquinolin-5-ylamino)pyrrolidin-1-yl)methyl)-1H-indol-1-yl)ethanol | 2c, 7, 8, 9, 10, 13, 16c |
| 2.061 | (R)-3-((3-(isoquinolin-5-ylamino)pyrrolidin-1-yl)methyl)phenol | 2c, 7, 8, 9, 10 |
| 2.062 | (R)-N-(1-(3,4-difluorobenzyl)pyrrolidin-3-yl)isoquinolin-5-amine | 2c, 7, 8, 9, 10 |
| 2.063 | (R)-N-(3-((3-(isoquinolin-5-ylamino)pyrrolidin-1-yl)methyl)benzyl)acetamide | 2c, 7, 8, 9, 10, 13, 16c |

TABLE A-continued

Exemplified Compounds.

| Compound | Structure | Select Embodiments 1-16 |
|---|---|---|
| 2.064 | (R)-2-(5-((3-(isoquinolin-5-ylamino)pyrrolidin-1-yl)methyl)-2-methylphenoxy)ethanol | 2c, 7, 8, 9, 10, 12a, 15c, 15d |
| 2.065 | (R)-N-(1-((1H-indol-5-yl)methyl)pyrrolidin-3-yl)isoquinolin-5-amine | 2c, 7, 8, 9, 10 |
| 2.066 | (R)-2-(5-((3-(isoquinolin-5-ylamino)pyrrolidin-1-yl)methyl)-1H-indol-1-yl)ethanol | 2c, 7, 8, 9, 10, 13, 16c |
| 2.067 | (R)-2-(5-((3-(isoquinolin-5-ylamino)pyrrolidin-1-yl)methyl)-2-methoxyphenoxy)ethanol | 2c, 7, 8, 9, 10, 12a, 15c, 15d |
| 2.068 | (R)-2-(2-fluoro-5-((3-(isoquinolin-5-ylamino)pyrrolidin-1-yl)methyl)phenoxy)ethanol | 2c, 7, 8, 9, 10, 12a, 15c, 15d |
| 2.069 | (R)-N-(2-((3-(isoquinolin-5-ylamino)pyrrolidin-1-yl)methyl)phenyl)piperidine-1-sulfonamide | 2c, 7, 8, 9, 10, 12a, 15c, 15d |

| Compound | Structure | Select Embodiments 1-16 |
|---|---|---|
| 2.070 | (R)-N-(1-((1-(methylsulfonyl)-1,2,3,4-tetrahydroquinolin-6-yl)methyl)pyrrolidin-3-yl)isoquinolin-5-amine | 2c, 7, 8, 9, 10, 12b, 15c, 15e |
| 2.071 | (R)-tert-butyl 2-(5-((3-(isoquinolin-5-ylamino)pyrrolidin-1-yl)methyl)-2-methylphenoxy)acetate | 2c, 7, 8, 9, 10, 12a, 15c, 15d |
| 2.072 | (R)-2-(3-((3-(isoquinolin-5-ylamino)pyrrolidin-1-yl)methyl)-1H-indol-1-yl)ethanol | 2c, 7, 8, 9, 10, 13, 16c |
| 2.073 | (R)-2-(5-((3-(isoquinolin-5-ylamino)pyrrolidin-1-yl)methyl)-2-methylphenoxy)acetic acid | 2c, 7, 8, 9, 10, 12a, 15c, 15d |
| 2.074 | (R)-N-(1-((1H-benzo[d]imidazol-2-yl)methyl)pyrrolidin-3-yl)isoquinolin-5-amine | 2c, 7, 8, 9, 10 |
| 2.075 | (R)-N-(1-((1-methyl-1H-benzo[d]imidazol-2-yl)methyl)pyrrolidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.076 | (R)-N-(5-((3-isoquinolin-5-ylamino)pyrrolidin-1-yl)methyl)-2-methylphenyl)methanesulfonamide | 2c, 7, 8, 9, 10, 12a, 15c, 15d |
| 2.077 | (R)-N-(5-((3-isoquinolin-5-ylamino)pyrrolidin-1-yl)methyl)-2-methylphenyl)-N',N' dimethylaminosulfamide | 2c, 7, 8, 9, 10, 12a, 15c, 15d |
| 2.078 | (R)-N-(3-((3-isoquinolin-5-ylamino)pyrrolidin-1-yl)methyl)-2-methylphenyl)methanesulfonamide | 2c, 7, 8, 9, 10, 12a, 15c, 15d |
| 2.079 | (R)-N-(3-((3-(isoquinolin-5-ylamino)pyrrolidin-1-yl)methyl)-2-methylphenyl)-N',N' dimethylaminosulfamide | 2c, 7, 8, 9, 10, 12a, 15c, 15d |
| 2.080 | (R)-5-(1-(3-(2-hydroxyethoxy)-4-methylbenzyl)pyrrolidin-3-ylamino)isoquinoline 2-oxide | 2b, 6b, 8, 9, 10, 12a, 15b, 15d |
| 2.081 | (R)-5-(1-(3-(2-hydroxyethoxy)benzyl)pyrrolidin-3-ylamino)isoquinoline 2-oxide | 2b, 6b, 8, 9, 10, 12a, 15b, 15d |
| 2.082 | (R)-N-(1-((2-(methylthio)pyrimidin-4-yl)methyl)pyrrolidin-3-yl)isoquinolin-5-amine | 2c, 7, 8, 9, 10, 12b, 15c, 15e |

| Compound | Structure | Select Embodiments 1-16 |
|---|---|---|
| 2.083 | (R)-N-(1-(pyrimidin-4-ylmethyl)pyrrolidin-3-yl)isoquinolin-5-amine | 2c, 7, 8, 9, 10 |
| 2.084 | (R)-N-(1-(pyrimidin-5-ylmethyl)pyrrolidin-3-yl)isoquinolin-5-amine | 2c, 7, 8, 9, 10 |
| 2.085 | (R)-N-(1-(pyrimidin-2-ylmethyl)pyrrolidin-3-yl)isoquinolin-5-amine | 2c, 7, 8, 9, 10 |
| 2.086 | (R)-N-(1-(pyrazin-2-ylmethyl)pyrrolidin-3-yl)isoquinolin-5-amine | 2c, 7, 8, 9, 10 |
| 2.087 | (R)-2-((3-(isoquinolin-5-ylamino)pyrrolidin-1-yl)methyl)-1H-benzo[d]imidazole-6-sulfonamide | 2c, 7, 8, 9, 10, 12b, 15c, 15e |
| 2.088 | (R)-N-(1-(thiophen-3-ylmethyl)pyrrolidin-3-yl)isoquinolin-5-amine | 2c, 7, 8, 9, 10 |
| 2.089 | (R)-N-(1-((5-nitrothiophen-3-yl)methyl)pyrrolidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.090 | 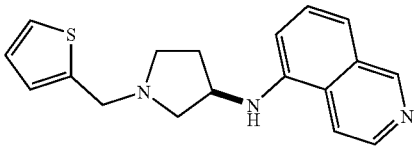<br>(R)-N-(1-(thiophen-2-ylmethyl)pyrrolidin-3-yl)isoquinolin-5-amine | 2c, 7, 8, 9, 10 |
| 2.091 | 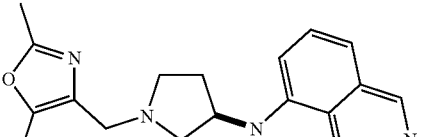<br>(R)-N-(1-((2,5-dimethyloxazol-4-yl)methyl)pyrrolidin-3-yl)isoquinolin-5-amine | 2c, 7, 8, 9, 10 |
| 2.092 | 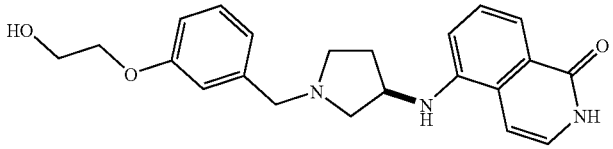<br>(R)-5-(1-(3-(2-hydroxyethoxy)benzyl)pyrrolidin-3-ylamino)isoquinolin-1(2H)-one | 2b, 6b, 8, 9, 10, 12a, 15b, 15d |
| 2.093 | 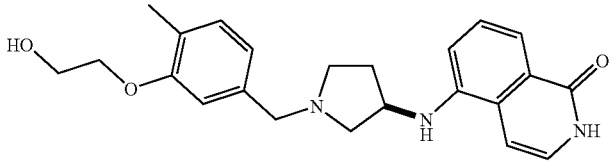<br>(R)-5-(1-(3-(2-hydroxyethoxy)-4-methylbenzyl)pyrrolidin-3-ylamino)isoquinolin-1(2H)-one | 2b, 6b, 8, 9, 10, 12a, 15b, 15d |
| 2.094 | 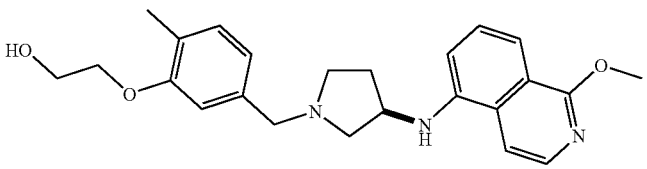<br>(R)-2-(5-((3-(1-methoxyisoquinolin-5-ylamino)pyrrolidin-1-yl)methyl)-2-methylphenoxy)ethanol | 2b, 6b, 8, 9, 10, 12a, 15b, 15d |
| 2.095 | 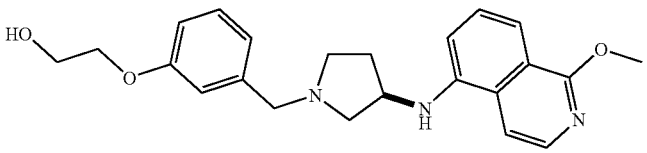<br>(R)-2-(3-((3-(1-methoxyisoquinolin-5-ylamino)pyrrolidin-1-yl)methyl)phenoxy)ethanol | 2b, 6b, 8, 9, 10, 12a, 15b, 15d |
| 2.096 | 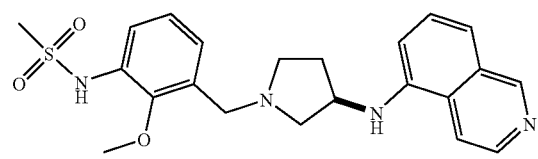<br>(R)-N-(3-((3-(isoquinolin-5-ylamino)pyrrolidin-1-yl)methyl)-2-methoxyphenyl)methanesulfonamide | 2c, 7, 8, 9, 10, 12a, 15c, 15d |

TABLE A-continued

Exemplified Compounds.

| Compound | Structure | Select Embodiments 1-16 |
|---|---|---|
| 2.097 | 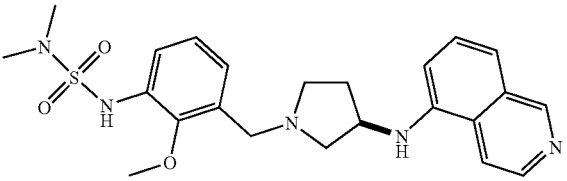<br>(R)-N-(3-((3-(isoquinolin-5-ylamino)pyrrolidin-1-yl)methyl)-2-methoxyphenyl)-N',N' dimethylaminosulfamide | 2c, 7, 8, 9, 10, 12a, 15c, 15d |
| 2.098 | 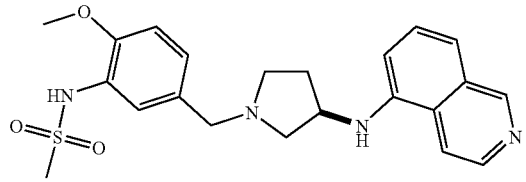<br>(R)-N-(5-((3-(isoquinolin-5-ylamino)pyrrolidin-1-yl)methyl)-2-methoxyphenyl)methanesulfonamide | 2c, 7, 8, 9, 10, 12a, 15c, 15d |
| 2.099 | 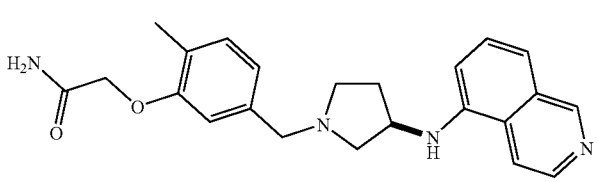<br>(R)-2-(5-((3-(isoquinolin-5-ylamino)pyrrolidin-1-yl)methyl)-2-methylphenoxy)acetamide | 2c, 7, 8, 9, 10, 12a, 15c, 15d |
| 2.100 | 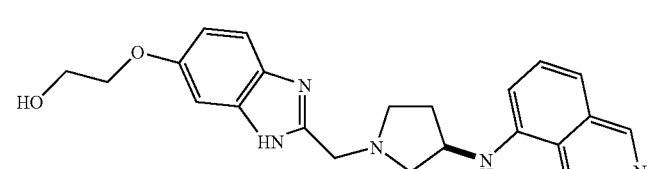<br>(R)-2-(2-((3-(isoquinolin-5-ylamino)pyrrolidin-1-yl)methyl)-1H-benzo[d]imidazol-6-yloxy)ethanol | 2c, 7, 8, 9, 10, 12a, 15c, 15d |
| 3.001 | 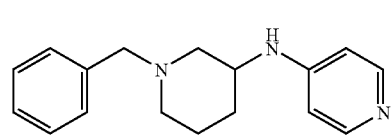<br>N-(1-benzylpiperidin-3-yl)pyridin-4-amine | 3c, 7, 8, 9, 10 |
| 3.002 | 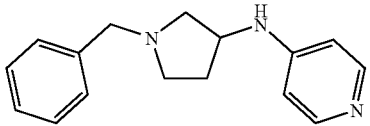<br>N-(1-benzylpyrrolidin-3-yl)pyridin-4-amine | 3c, 7, 8, 9, 10 |
| 4.001 | 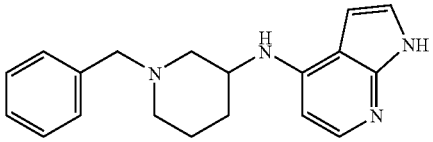<br>N-(1-benzylpiperidin-3-yl)-1H-pyrrolo[2,3-b]pyridin-4-amine | 4c, 7, 8, 9, 10 |

TABLE A-continued

Exemplified Compounds.

| Compound | Structure | Select Embodiments 1-16 |
|---|---|---|
| 4.002 | 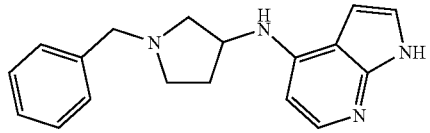<br>N-(1-benzylpyrrolidin-3-yl)-1H-pyrrolo[2,3-b]pyridin-4-amine | 4c, 7, 8, 9, 10 |
| 5.001 | 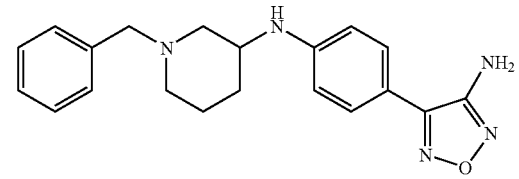<br>4-(4-(1-benzylpiperidin-3-ylamino)phenyl)-1,2,5-oxadiazol-3-amine | 5a, 7, 8, 9, 10 |
| 5.002 | 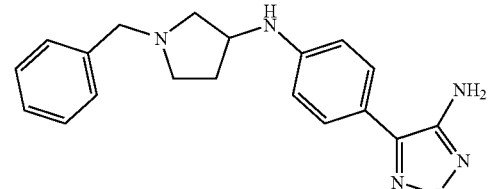<br>4-(4-(1-benzylpyrrolidin-3-ylamino)phenyl)-1,2,5-oxadiazol-3-amine | 5a, 7, 8, 9, 10 |

Preferred ROCK inhibitor compounds of this invention include, but are not limited to the ROCK inhibitor compounds of embodiments 5, 14, 15, 16, 17, 18, 19, 20, and 21 as described above, and their associated salts, tautomers, solvates, or hydrates. In particular, preferred Compounds include 1.074, 1.075, 1.076, 1.077, 1.079, 1.091, 1.093, 1.108, 1.109, 1.123, 1.124, 1.126, 1.131, 1.132, 1.133, 1.134, 1.135, 1.136, 1.137, 1.138, 1.141, 1.148, 1.149, 1.150, 1.152, 1.153, 1.155, 1.156, 1.157, 1.158, 1.161, 1.162, 1.163, 1.164, 1.165, 1.166, 1.171, 1.173, 1.175, 1.176, 1.186, 1.193, 1.195, 1.197, 1.200, 1.206, 1.212, 1.213, 1.215, 1.217, 1.219, 1.223, 1.233, 1.236, 1.237, 1.238, 1.239, 1.249, 1.252, 1.253, 1.258, 1.259, 1.260, 1.261, 1.262, 1.270, 1.273, 1.275, 1.277, 1.281, 2.025, 2.026, 2.031, 2.038, 2.039, 2.041, 2.046, 2.047, 2.054, 2.055, 2.057, 2.058, 2.059, 2.060, 2.061, 2.064, 2.065, 2.066, 2.067, 2.068, 2.069, 2.072, 2.073, 2.076, 2.077, 2.078, 2.079, 2.082, 2.096, 2.097, and 2.099.

Pharmaceutical Formulations

The present invention provides a pharmaceutical formulation comprising compounds of Formula I or II and a pharmaceutically acceptable carrier. Pharmaceutically acceptable carriers can be selected by those skilled in the art using conventional criteria. Pharmaceutically acceptable carriers include, but are not limited to, saline solution, aqueous electrolyte solutions, isotonicity modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical formulation useful for the present invention in general is an aqueous solution comprising water, suitable ionic or non-ionic tonicity modifiers, suitable buffering agents, and a compound of Formula I or II. In one embodiment, the compound is at 0.005 to 3% w/v, and the aqueous solution has a tonicity of 200-400 mOsm/kG and a pH of 4-9.

In one embodiment, the tonicity modifier is ionic such as NaCl, for example, in the amount of 0.5-0.9% w/v, preferably 0.6-0.9% w/v.

In another embodiment, the tonicity modifier is non-ionic, such as mannitol, dextrose, in the amount of at least 2%, or at least 2.5%, or at least 3%, and no more than 7.5%; for example, in the range of 3-5%, preferably 4-5% w/v.

The pharmaceutical formulation can be sterilized by filtering the formulation through a sterilizing grade filter, preferably of a 0.22-micron nominal pore size. The pharmaceutical formulation can also be sterilized by terminal sterilization using one or more sterilization techniques including but not limited to a thermal process, such as an autoclaving process, or a radiation sterilization process, or using pulsed light to produce a sterile formulation. In one embodiment, the pharmaceutical formulation is a concentrated solution of the active ingredient; the formulation can be serially diluted using appropriate acceptable sterile diluents prior to systemic administration.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Pharmaceutical compositions of the invention can be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions can also contain sweetening and flavoring agents.

Pharmaceutical compositions of the invention can be in the form of an aerosol suspension of respirable particles comprising the active compound, which the subject inhales. The respirable particles can be liquid or solid, with a particle size sufficiently small to pass through the mouth and larynx upon inhalation. In general, particles having a size of about 1 to 10 microns, preferably 1-5 microns, are considered respirable.

The pharmaceutical formulation for systemic administration such as injection and infusion is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile injectable preparation can be a sterile injectable solution or suspension in a non-toxic acceptable diluent or solvent. Among the acceptable vehicles and solvents that can be employed are sterile water, saline solution, or Ringer's solution.

The pharmaceutical compositions for oral administration contain active compounds in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

The pharmaceutical compositions can be in the form of suppositories, which are prepared by mixing the active ingredient with a suitable non-irritating excipient that is solid at ordinary temperatures but liquid at the rectal temperature and will thus melt in the rectum to release the compound. Such excipients include cocoa butter and polyethylene glycols.

Method of Treating Neurological and Neuropathic Diseases Using Formula I/II Compounds The present invention is useful in treating diseases associated with excessive inflammation, neurodegeneration, and axonal/neurite retraction. The present invention is particularly effective in treating neurological diseases such as cerebral ischemia, stroke, neuropathic pain, spinal cord injury, Alzheimer's disease, and multiple sclerosis.

Cerebral Ischemia and Stroke

The inventors have discovered that ROCK inhibitor Compounds of Formula I or II inhibit the inflammation and neurodegeneration associated with cerebral ischemia and stroke. The present invention is directed to a method of treating cerebral ischemia and stroke. The method comprises the steps of first identifying a subject suffering from cerebral ischemia/stroke, then administering to the subject an effective amount of a ROCK inhibitor Compound of Formula I or II to treat said disease.

Statistical and demonstrable improvement in the following variables would all indicate efficacious treatment of cerebral ischemia, corresponding to a reduction in brain damage and/or an increase in healing of damaged vessels and tissue: increased recanalization, greater restoration of lumen, reduction of size of brain infarction (measured by neural imaging from MRI, CT, CTA, MRA, or ultrasound), improved results from an EKG, reduced concentration of neutrophils and other leukocytes both systemically and in the affected area, and a decrease in NIHSS (National Institute of Health Stroke Scale) score from baseline before treatment to later timepoints.

Spinal Cord Injury

The inventors have discovered that ROCK inhibitor Compounds of Formula I or II inhibit the neurodegeneration and neurite retraction associated with spinal cord injury. The present invention is directed to a method of treating spinal cord injury. The method comprises the steps of first identifying a subject suffering from spinal cord injury, then administering to the subject an effective amount of a ROCK inhibitor Compound of Formula I or II to treat said disease.

Indicia of efficacy for spinal cord injury include demonstrable improvement in measurable signs and symptoms. Improvements include recuperating muscle strength, mobility, independence, and fine motor skills. Other signs include regaining control of bladder, bowel, pain, muscle spasms, breathing, and consciousness. The following three tests that demonstrate sensory recovery include the pinprick sensation, light touch sensation, and motor function. Diagnostic tests such as X-rays, CT scans, and MRI's allow closer look at the vertebrae to see signs of a decrease in compression while the myelography allows visualization of spinal nerves. Improvements also include restoring the ability to move arms and legs and function sexually, which includes male fertility, erectile function, ejaculatory function, and better sperm quality. Other signs consist of a decrease in extreme back pain and pressure around the neck and back, increase in body coordination and decrease in paralysis in parts of the body. Cardiovascular improvements consequential of SPI diagnosed patients include reduced occurrence of autonomic dysreflexia, coronary heart disease, deep venous thrombosis, pulmonary embolism and orthostatic hypotension. The following are improvements in urinary complications resultant of SCI: no vesicoureteral reflux, renal failure, nephrolithiasis, bladder dysfunction, detrusor hyperactivity, sphincter hyperactivity, bladder flaccidity, urinary tract infection, urinary calculi, vesicoureteral reflux and renal insufficiency. Factors associated with a general improvement in the quality of life consist of a decreased need for hospitalization, medical office visits, or medical procedures.

Neuropathic Pain

The inventors have discovered that ROCK inhibitor Compounds of Formula I or II inhibit the neuro-remodeling associated with increased neuro-sensation associated with neuropathic pain. The present invention is directed to a method of treating neuropathic pain. The method comprises the steps of first identifying a subject suffering from neuropathic pain, then administering to the subject an effective amount of a ROCK inhibitor Compound of Formula I or II to treat said disease.

Indicia of efficacy for neuropathic pain include demonstrable improvement in measurable signs, symptoms, and other variables clinically relevant to neuropathy. Such improvements include decrease in abnormal sensation, neural regeneration, neural functional recovery, reduced pain symptoms, improved sleeping patterns, decreased secondary myofacial pain, increased ambulatory activities, decreased abnormal skin sensation, decreased allodynia (painful response to non-painful stimulus), decreased hyperalgesia (increased painful response to painful stimulus), decreased ER/office visits, decreased length of hospital stay, decreased usage of unsafe pain therapies, decrease in missed work or school days, decreased depression, increased feelings of well-being and overall improved quality of life.

Alzheimer's Disease

The inventors have discovered that ROCK inhibitor Compounds of Formula I or II inhibit the neurodegeneration associated with Alzheimer's disease. The present invention is directed to a method of treating Alzheimer's disease. The method comprises the steps of first identifying a subject suffering from Alzheimer's disease, then administering to the subject an effective amount of a ROCK inhibitor Compound of Formula I or II to treat said disease.

Indicia of efficacy for Alzheimer's disease include demonstrable improvement in measurable signs, symptoms and other variables clinically relevant to Alzheimer's. Such improvements include an increase in ability to make decisions, increase in focal motor skills, improved memory, a decrease in the number of unprovoked falls, fewer urinary symptoms not explained by urinary disease (frequency, urgency), fewer mood changes, decreased depression, decrease in number of hospital visits, decrease in length of hospital stay, increased feelings of well-being and improved quality of life, survival, improvement in the COGDRAS tests of attention and visuospatial orientation, in the Alzheimer's Disease Cooperative Study-Activities of Daily Living (ADCS-ADL) Inventory, in the Alzheimer's Disease Cooperative Study-Clinicians Global Impression of Change (ADCS-CGIC) or in the Alzheimer's Disease Assessment Scale Cognitive (ADAS-Cog).

Multiple Sclerosis

The inventors have discovered that ROCK inhibitor Compounds of Formula I or II inhibit the inflammation and neurodegeneration associated with multiple sclerosis. The present invention is directed to a method of treating multiple sclerosis. The method comprises the steps of first identifying a subject suffering from multiple sclerosis, then administering to the subject an effective amount of a ROCK inhibitor Compound of Formula I or II to treat said disease.

Indicia of efficacy for treating multiple sclerosis by the present invention include demonstrable improvements in visual symptoms including a decreased incidence of blurred vision and eye pain, recovering eyesight and color vision, not experiencing double vision or jerky eye movements, and experiencing coordination between two eyes and normal pupil responses. Improvements in motor symptoms consist of increased muscle strength, lack of muscle spasms, regaining muscle tone and posture, and decreased slurred speech and jerky muscle movements. Indications that the patient is improving in terms of sensation include a decreased frequency of numbness and tingling sensations, regaining sensation and awareness of body parts, and a lessening pain throughout the body and face. In terms of coordination and balance, the patient shows progress if they do not shake, regain coordination, can control limb movements, experience normal balance function in the inner ear, does not experience nausea or vomiting, can coordinate speech, and has ability to produce rhythmic movements. Improvements associated with the urogenital system comprise urinary continence and retention, erectile function, and normal ejaculation. Cognitive progress includes not suffering short-term and long-term memory problem and ability to comprehend speech. Other signs of improvement include a reduced incidence of acid reflux, epileptic seizures, and swallowing and respiratory difficulties.

Methods of Administration

The present invention is particularly effective in treating neurological diseases or conditions such as cerebral ischemia, stroke, neuropathic pain, spinal cord injury, Alzheimer's disease, and multiple sclerosis. Any method of delivering the compound to the target tissues, including local administration and systemic administration, is suitable for the present invention.

In one embodiment, the active compound is delivered by systemic administration; the compound first reaches plasma and then distributes into the target tissues. Examples of systemic administration include oral ingestion, or intravenous or subcutaneous or intraperitoneal or intrathecal or intramuscular administration.

Additional method of systemic administration of the active compound to a subject involves administering a suppository form of the active compound, such that a therapeutically effective amount of the compound reaches the target sites via systemic absorption and circulation.

Another method of systemically administering the active compounds to the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

The active compounds can also be systemically administered to the subject through absorption by the skin using transdermal patches or pads. The active compounds are absorbed into the bloodstream through the skin. Plasma concentration of the active compounds can be controlled by using patches containing different concentrations of active compounds.

For systemic administration, plasma concentrations of active compounds delivered can vary according to compounds; but are generally $1\times10^{-10}$–$1\times10^{-4}$ moles/liter, and preferably $1\times10^{-8}$–$1\times10^{-5}$ moles/liter.

Dosage levels about 0.01-140 mg per kg, preferably 0.1-100 mg/kg of body weight per day are useful in the treatment or preventions of conditions involving an inflammatory response (about 0.5 mg to about 7 g per patient per day). Preferred dosage levels are about 0.05-25, or 0.1-10 mg/kg body weight per day. The amount of active ingredient that can be combined with the carrier materials to produce a single dosage form will vary depending upon the host treated and the particular mode of administration. Dosage unit forms will generally contain between from about 1 mg to about 500 mg of an active ingredient.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more can be administered to achieve adequate steady state levels. The maximum total dose in general does not exceed about 2 g/day for a 40 to 80 kg human patient.

Frequency of dosage can also vary depending on the compound used and the particular disease treated. However, for treatment of most disorders, a dosage regimen of p.r.n, 4 times daily, three times daily, or less is preferred, with a dosage regimen of once daily or 2 times daily being particularly preferred.

In another embodiment, the active compound is delivered by inhalation, topical application, or targeted drug delivery to the target tissue. Methods of inhalation include liquid instillation, instillation as a pressurized fluid preparation via metered dose inhaler or equivalent, or inhalation of an aerosolized solution via nebulizer (preferred), inhalation of dry powder (more preferred), and directing soluble or dried material into the air stream during mechanical ventilation (also more preferred).

One administration method is administering to a subject an aerosol suspension of respirable particles comprising the active compound by inhalation. The respirable particles can be liquid or solid, with a particle size sufficiently small to pass through the mouth and larynx upon inhalation; in general, particles ranging from about 1 to 10 microns, but more preferably 1-5 microns, in size are considered respirable. The surface concentrations of active compounds delivered via inhalation can vary according to compounds; but are generally $1\times10^{-10}$–$1\times10^{-4}$ moles/liter, and preferably $1\times10^{-8}$–$1\times10^{-5}$ moles/liter.

It is understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Preferred compounds of the invention will have favorable pharmacological properties. Such properties include, but are not limited to bioavailability, low toxicity, low serum protein binding and desirable in vitro and in vivo half-life. Distribution in the body to sites of complement activity is also desirable, e.g., compounds used to treat CNS disorders will preferably penetrate the blood brain barrier, while low brain levels of compounds used to treat peripheral disorders are typically preferred.

An example of targeted drug delivery is enclosure of the compound within a liposome, where the liposome is coated with a specific antibody whose antigen is expressed in the targeted tissue. It can be advantageous to construe a controlled delivery system of the compounds since such an inhaled product targets the site of action, presents the compound of interest in small regimented quantities and reduces/minimizes any unwanted side effects.

Another example of a delivery system includes microparticulate compositions of the compound. In such a case, the compound is formulated as a microparticulate wherein the carrier is loaded with the compound; such a preparation is then filtered through a fine porous membrane or suitable filtering medium or is exposed to solvent interchanges to produce nanoparticles. Such preparations can be freeze dried or held in suspension in an aqueous or physiologically compatible medium. The preparation so obtained can be inhaled by suitable means.

Another example of a suitable preparation includes a reconstitutable preparation. In this case, the compound is formulated in a preparation to contain the necessary adjuvant to make it physiologically compatible. Such a preparation can be reconstituted by addition of water for injection or suitable physiological fluids, admixed by simple agitation and inhaled using appropriate techniques described above.

The compounds described above can also be prepared into dry powder or equivalent inhalation powders using the well known art of super critical fluid technology. In such a case, the compound is admixed with appropriate excipients and milled into a homogenous mass using suitable solvents or adjuvants. Following this, this mass is subjected to mixing using super critical fluid technology and suitable particle size distribution achieved. The particles in the formulation need to be of a desired particle size range such that the particles can be inhaled into the lungs using a suitable inhalation technique or introduced into the lungs via a mechanical ventilator. Alternatively, a formulation can be designed such that the particles are large enough in size thereby offering sufficient surface area to dissolve completely in a suitable fluid when admixed together or to dissolve sufficiently enough prior to nebulization into the lungs.

High doses are sometimes required for therapeutic agents to achieve the desired levels of analgesic response, but high drug doses are often associated with a greater frequency of dose-related adverse effects. Thus, another advantage of the use of the compounds in this invention may be to reduce the number and/or severity of such side effects as tolerance, dependence, constipation, respiratory depression, sedation, and/or gastrointestinal side effects from drugs used to treat neurological and neuropathic diseases claimed in this invention.

The invention is illustrated further by the following examples that are not to be construed as limiting the invention in scope to the specific procedures described in them.

EXAMPLES

Example 1

Rho Kinase Inhibition Assay

Relevance:

This assay demonstrates a compound's ability to inhibit ROCK2 and ROCK1 in an in vitro setting using the isolated enzyme. Compounds having ROCK2 IC$_{50}$ values on the order of 2 μM or below have been shown to possess efficacy in many studies using in vivo models of the disease processes described in this application.

Protocol

Inhibition of ROCK2 and ROCK1 activity was determined using the IMAP™ Screening Express Kit (Molecular Devices product number #8073). ROCK2 enzyme (Upstate/Chemicon #14-451), ROCK1 (Upstate/Chemicon #14-601) and Flourescein tagged substrate peptide Fl-AKRRRLSSLRA (Molecular Devices product number R7184) was pre-incubated with a test compound (a Formula I or II compound or other rho kinase compound such as fasudil, H-1152, H7, Y-27632, Y-39983) for 5 minutes in buffer containing 10 mM Tris-HCl pH 7.2, 10 mM MgCl$_2$, and 0.1% BSA. Following the pre-incubation, 10 μM ATP was added to initiate the reaction. After 60 minutes at room temperature, Molecular Devices IMAP™ binding solution was added to bind phosphorylated substrate. After 30 minutes of incubation in the presence of the IMAP™ beads, the fluorescence polarization was read and the ratio was reported as mP. IC$_{50}$ values for compounds and EC$_{50}$ values for ATP were calculated using the Prism software from Graphpad.

Results:

TABLE 1

Rho Kinase I and II Potency Data

| Compound | ROCK1 Ki, Avg, nM | ROCK1 Ki, StdDev, nM | ROCK2 Ki, Avg, nM | ROCK2 Ki, StdDev, nM |
| --- | --- | --- | --- | --- |
| 1.008 | 30.5 | 0.8 | 3.9 | 0.1 |
| 1.034 | 36.0 | 22.2 | 5.3 | 2.6 |
| 1.039 | 208.6 | 109.0 | 24.7 | 8.4 |
| 1.051 | 37.2 | 4.0 | 3.8 | 0.0 |
| 1.072 | 33.7 | 22.1 | 5.6 | 3.1 |
| 1.074 | 40.1 | 3.3 | 4.1 | 1.5 |
| 1.075 | 48.7 | 2.8 | 4.4 | 0.3 |
| 1.076 | 14.3 | 5.4 | 2.6 | 0.6 |
| 1.077 | 76.1 | 30.9 | 11.1 | 5.8 |
| 1.078 | 36.3 | 10.1 | 3.6 | 0.9 |
| 1.079 | 71.5 | 9.1 | 4.7 | 1.1 |
| 1.080 | 130.8 | 42.6 | 15.2 | 4.4 |
| 1.087 | 84.1 | 11.1 | 15.4 | 1.4 |
| 1.090 | 281.0 | 103.7 | 24.9 | 7.9 |
| 1.091 | 71.4 | 22.0 | 3.3 | 1.0 |
| 1.092 | 190.5 | 42.2 | 28.4 | 10.6 |
| 1.093 | 64.5 | 21.9 | 7.7 | 5.2 |
| 1.095 | 274.8 | 88.0 | 49.5 | 35.9 |
| 1.098 | 205.6 | 69.4 | 25.0 | 6.4 |
| 1.106 | 223.4 | 82.0 | 15.1 | 4.9 |
| 1.107 | 233.7 | 137.2 | 14.0 | 8.5 |
| 1.108 | 25.6 | 3.2 | 6.5 | 0.3 |
| 1.109 | 58.8 | 25.8 | 9.6 | 2.5 |
| 1.110 | 59.0 | 4.1 | 11.2 | 0.3 |
| 1.115 | 89.7 | 17.5 | 20.6 | 1.7 |
| 1.116 | 257.8 | 45.6 | 48.9 | 5.5 |
| 1.117 | 208.0 | 1.9 | 35.8 | 2.3 |
| 1.118 | 461.7 | 28.3 | 81.7 | 52.7 |
| 1.123 | 82.3 | 11.0 | 9.6 | 4.3 |
| 1.124 | 64.5 | 7.9 | 3.3 | 0.8 |
| 1.125 | 557.1 | 1.7 | 50.9 | 16.8 |
| 1.126 | 76.2 | 16.7 | 17.2 | 3.9 |
| 1.127 | 96.6 | 11.6 | 11.2 | 0.4 |
| 1.130 | 577.1 | 340.0 | 142.0 | 38.1 |
| 1.131 | 19.7 | 5.9 | 3.8 | 0.9 |
| 1.132 | 22.5 | 6.5 | 3.5 | 0.4 |
| 1.133 | 25.0 | 7.2 | 4.3 | 1.1 |
| 1.134 | 22.4 | 6.0 | 4.4 | 0.6 |
| 1.136 | 40.3 | 15.3 | 5.4 | 0.4 |
| 1.137 | 25.8 | 10.7 | 5.1 | 1.2 |
| 1.138 | 36.3 | 12.2 | 7.2 | 1.1 |
| 1.139 | 200.3 | 26.3 | 23.2 | 9.6 |
| 1.140 | 236.1 | 199.3 | 32.9 | 24.9 |
| 1.141 | 28.5 | 11.1 | 3.8 | 1.1 |

TABLE 1-continued

Rho Kinase I and II Potency Data

| Compound | ROCK1 Ki, Avg, nM | ROCK1 Ki, StdDev, nM | ROCK2 Ki, Avg, nM | ROCK2 Ki, StdDev, nM |
| --- | --- | --- | --- | --- |
| 1.142 | 104.2 | 26.6 | 12.0 | 4.4 |
| 1.143 | 49.7 | 30.8 | 12.6 | 11.9 |
| 1.144 | 97.6 | 65.0 | 19.5 | 13.0 |
| 1.145 | 35.0 | 13.5 | 6.4 | 0.9 |
| 1.146 | 39.8 | 10.9 | 10.7 | 1.5 |
| 1.147 | 58.3 | 15.6 | 45.7 | 52.0 |
| 1.148 | 24.3 | 13.7 | 3.6 | 0.9 |
| 1.149 | 46.8 | 21.3 | 4.2 | 2.2 |
| 1.150 | 33.2 | 17.5 | 3.2 | 1.2 |
| 1.151 | 22.8 | 6.0 | 2.9 | 0.5 |
| 1.152 | 19.8 | 13.3 | 3.3 | 0.9 |
| 1.153 | 62.8 | 8.7 | 4.2 | 0.8 |
| 1.154 | 52.7 | 9.5 | 6.6 | 1.0 |
| 1.155 | 45.4 | 14.7 | 7.0 | 2.0 |
| 1.156 | 135.8 | 34.3 | 13.0 | 3.0 |
| 1.157 | 263.8 | 73.9 | 8.8 | 1.6 |
| 1.158 | 64.1 | 20.1 | 5.1 | 1.0 |
| 1.159 | 48.1 | 9.2 | 10.1 | 2.6 |
| 1.160 | 218.3 | 28.3 | 49.4 | 13.4 |
| 1.161 | 9.9 | 3.4 | 2.5 | 0.5 |
| 1.162 | 15.2 | 1.5 | 2.8 | 0.8 |
| 1.163 | 33.6 | 5.8 | 2.9 | 0.4 |
| 1.164 | 42.4 | 7.2 | 6.1 | 1.2 |
| 1.165 | 50.7 | 4.4 | 3.4 | 0.6 |
| 1.166 | 95.2 | 8.6 | 8.0 | 0.8 |
| 1.167 | 118.6 | 17.1 | 18.5 | 1.7 |
| 1.168 | 162.2 | 68.3 | 22.9 | 10.4 |
| 1.169 | 256.2 | 132.7 | 33.8 | 20.0 |
| 1.170 | 80.0 | 25.9 | 12.5 | 6.1 |
| 1.171 | 109.2 | 60.1 | 16.0 | 8.4 |
| 1.172 | 103.0 | 40.6 | 20.5 | 7.3 |
| 1.173 | 15.1 | 6.8 | 3.6 | 1.0 |
| 1.175 | 65.9 | 28.3 | 7.6 | 1.5 |
| 1.176 | 314.3 | 77.6 | 11.2 | 3.2 |
| 1.177 | 156.1 | 55.0 | 18.2 | 5.5 |
| 1.178 | 137.6 | 58.0 | 24.9 | 17.6 |
| 1.179 | 292.0 | 70.7 | 19.3 | 4.4 |
| 1.180 | 138.5 | 46.5 | 23.1 | 4.8 |
| 1.181 | 567.8 | 191.3 | 32.8 | 3.5 |
| 1.182 | 408.3 | 106.6 | 30.6 | 4.3 |
| 1.183 | 165.1 | 46.3 | 16.8 | 3.7 |
| 1.184 | 843.1 | 53.0 | 90.9 | 13.9 |
| 1.185 | 81.6 | 33.0 | 12.6 | 6.4 |
| 1.186 | 129.3 | 42.2 | 11.9 | 4.9 |
| 1.187 | 296.2 | 78.8 | 17.3 | 5.8 |
| 1.188 | 3468.8 | | 652.7 | |
| 1.189 | 187.9 | 62.0 | 34.3 | 5.1 |
| 1.190 | 325.6 | 38.9 | 71.8 | 9.0 |
| 1.191 | 147.3 | 24.7 | 33.4 | 2.0 |
| 1.192 | 158.4 | 33.5 | 37.7 | 4.7 |
| 1.193 | 64.9 | 4.2 | 14.8 | 1.2 |
| 1.194 | 175.7 | 6.3 | 20.2 | 2.4 |
| 1.195 | 196.2 | 58.0 | 10.3 | 3.6 |
| 1.196 | 710.7 | 191.7 | 39.8 | 15.0 |
| 1.197 | 120.2 | 36.0 | 5.0 | 1.4 |
| 1.198 | 584.5 | 139.5 | 24.7 | 9.9 |
| 1.199 | 1856.6 | | 213.0 | 34.4 |
| 1.200 | 76.5 | 17.9 | 5.9 | 0.9 |
| 1.201 | 1585.4 | | 229.5 | |
| 1.202 | 203.5 | 40.9 | 33.0 | 2.1 |
| 1.203 | 329.4 | 67.4 | 41.6 | 6.4 |
| 1.204 | 196.1 | 42.0 | 31.9 | 2.2 |
| 1.205 | 498.1 | 95.2 | 46.4 | 3.7 |
| 1.206 | 64.4 | 15.1 | 9.1 | 3.8 |
| 1.207 | 516.3 | 27.5 | 43.7 | 1.1 |
| 1.208 | 54.2 | 25.0 | 12.9 | 2.8 |
| 1.209 | 4591.0 | | 469.6 | 58.3 |
| 1.210 | 95.1 | 18.2 | 25.5 | 3.8 |
| 1.211 | 395.5 | 58.5 | 57.6 | 0.6 |
| 1.212 | 44.2 | 11.2 | 3.9 | 0.2 |
| 1.213 | 106.3 | 10.9 | 3.0 | 0.5 |
| 1.214 | 546.5 | 10.9 | 143.0 | 7.0 |
| 1.215 | 102.8 | 5.8 | 3.5 | 0.3 |
| 1.216 | 1885.4 | | 402.9 | 79.5 |
| 1.217 | 70.1 | 9.5 | 12.1 | 1.1 |

TABLE 1-continued

Rho Kinase I and II Potency Data

| Compound | ROCK1 Ki, Avg, nM | ROCK1 Ki, StdDev, nM | ROCK2 Ki, Avg, nM | ROCK2 Ki, StdDev, nM |
|---|---|---|---|---|
| 1.218 | 401.8 | 34.4 | 30.7 | 3.0 |
| 1.219 | 343.6 | 37.6 | 15.4 | 2.3 |
| 1.221 | 264.4 | 41.6 | 30.0 | 2.6 |
| 1.222 | 228.8 | 41.9 | 75.5 | 1.2 |
| 1.223 | 239.5 | 21.5 | 15.7 | 1.9 |
| 1.224 | 487.0 | 151.5 | 77.5 | 23.0 |
| 1.225 | 605.0 | 133.2 | 189.4 | 48.9 |
| 1.226 | 91.7 | 31.5 | 8.8 | 2.6 |
| 1.227 | 47.5 | 2.8 | 5.3 | 0.4 |
| 1.228 | 1883.4 | 681.9 | 139.6 | 28.2 |
| 1.229 | 121.4 | 86.2 | 18.4 | 5.8 |
| 1.230 | 345.9 | 85.2 | 35.3 | 9.8 |
| 1.231 | 305.1 | 62.8 | 60.3 | 18.2 |
| 1.232 | 136.6 | 41.1 | 20.8 | 8.8 |
| 1.233 | 47.2 | 7.2 | 1.3 | 0.1 |
| 1.234 | 1735.2 | 179.0 | 166.4 | 11.6 |
| 1.235 | 1386.4 | 173.1 | 335.4 | 29.4 |
| 1.236 | 49.3 | 7.1 | 2.1 | 0.1 |
| 1.237 | 286.7 | 55.0 | 4.0 | 0.4 |
| 1.238 | 61.2 | 22.1 | 1.5 | 0.3 |
| 1.239 | 282.6 | 36.2 | 6.3 | 0.6 |
| 1.240 | 624.8 | 74.2 | 60.1 | 9.3 |
| 1.241 | 65.1 | 11.8 | 21.0 | 6.4 |
| 1.242 | 71.4 | 14.1 | 17.5 | 1.8 |
| 1.243 | 219.3 | 29.7 | 84.3 | 17.2 |
| 1.244 | 683.1 | 80.9 | 138.7 | 25.4 |
| 1.245 | 199.0 | 27.7 | 49.5 | 7.9 |
| 1.246 | 92.1 | 6.3 | 11.2 | 0.8 |
| 1.247 | 1312.4 | 268.7 | 242.6 | 53.1 |
| 1.248 | 2349.7 | | 890.6 | 509.8 |
| 1.249 | 91.7 | 25.0 | 8.6 | 3.8 |
| 1.250 | 247.0 | 63.7 | 45.8 | 13.8 |
| 1.251 | 206.8 | 44.0 | 49.2 | 10.5 |
| 1.252 | 30.5 | 1.5 | 4.5 | 0.4 |
| 1.253 | 59.9 | 7.4 | 1.7 | 0.2 |
| 1.254 | 116.0 | 19.4 | 39.0 | 8.7 |
| 1.255 | 3559.3 | 1202.9 | 358.9 | 99.3 |
| 1.256 | 700.1 | 179.5 | 85.5 | 18.8 |
| 1.257 | 1273.7 | 237.3 | 168.0 | 35.4 |
| 1.258 | 9.5 | 3.5 | 1.3 | 0.4 |
| 1.259 | 19.5 | 11.6 | 2.1 | 0.3 |
| 1.260 | 70.9 | 48.0 | 7.1 | 1.9 |
| 1.261 | 307.4 | 139.0 | 14.8 | 6.5 |
| 1.262 | 54.9 | 13.3 | 4.0 | 0.7 |
| 1.263 | 2130.5 | 673.5 | 453.4 | 105.3 |
| 1.264 | 494.5 | 1.1 | 59.4 | 9.5 |
| 1.265 | 161.7 | 25.9 | 21.6 | 0.8 |
| 1.266 | 53.8 | 15.1 | 17.1 | 2.8 |
| 1.267 | 98.8 | 21.6 | 23.9 | 6.2 |
| 1.268 | 403.6 | 78.8 | 40.7 | 7.5 |
| 1.269 | 239.1 | 62.6 | 22.8 | 9.0 |
| 1.270 | 130.5 | 45.0 | 9.9 | 0.6 |
| 1.271 | 332.1 | 99.9 | 77.7 | 5.8 |
| 1.272 | 1823.7 | 1294.6 | 194.3 | 17.0 |
| 1.273 | 31.3 | 8.3 | 8.2 | 1.0 |
| 1.274 | 223.4 | 46.3 | 10.7 | 1.1 |
| 1.275 | 401.7 | 44.9 | 14.1 | 2.0 |
| 1.276 | 64.2 | 5.2 | 12.3 | 2.5 |
| 1.277 | 42.3 | 10.4 | 4.6 | 1.3 |
| 1.278 | 80.2 | 10.5 | 10.2 | 1.8 |
| 1.279 | 455.9 | 20.3 | 34.2 | 1.6 |
| 1.280 | 746.0 | 58.3 | 38.0 | 4.0 |
| 1.281 | 71.8 | | 7.4 | |
| 2.007 | 390.4 | | 179.1 | |
| 2.016 | 100.5 | 14.8 | 42.4 | 10.2 |
| 2.020 | 100.5 | 13.1 | 36.5 | 4.7 |
| 2.022 | 44.8 | 6.9 | 15.3 | 1.1 |
| 2.025 | 6.9 | 1.3 | 2.9 | 0.5 |
| 2.026 | 38.0 | 15.2 | 13.0 | 4.1 |
| 2.027 | 15.7 | 3.8 | 7.4 | 2.3 |
| 2.031 | 14.6 | 4.9 | 5.3 | 1.2 |
| 2.034 | 1002.6 | 392.4 | 221.1 | 312.7 |
| 2.035 | 601.0 | | 201.9 | |
| 2.036 | 579.5 | 139.9 | 232.8 | |
| 2.037 | 920.8 | | 182.2 | |
| 2.038 | 28.9 | 4.5 | 6.3 | 1.0 |
| 2.039 | 18.8 | 9.6 | 6.7 | 1.9 |
| 2.040 | 59.6 | 10.7 | 25.4 | 5.0 |
| 2.041 | 30.8 | 2.6 | 9.6 | 2.6 |
| 2.043 | 49.4 | 9.5 | 21.5 | 2.4 |
| 2.044 | 81.4 | 20.2 | 24.1 | 3.7 |
| 2.045 | 90.6 | 64.6 | 88.0 | 57.3 |
| 2.046 | 16.7 | 1.1 | 5.6 | 0.8 |
| 2.047 | 26.4 | 3.6 | 7.0 | 2.3 |
| 2.048 | 71.5 | 22.8 | 34.6 | 9.7 |
| 2.049 | 113.0 | 42.1 | 48.0 | 17.1 |
| 2.050 | 367.7 | 115.4 | 250.7 | |
| 2.051 | 1437.2 | 595.4 | 1179.8 | |
| 2.052 | 508.5 | 169.1 | 142.6 | |
| 2.053 | 951.6 | 157.1 | 182.4 | |
| 2.054 | 17.1 | 2.3 | 3.7 | 0.1 |
| 2.055 | 16.0 | 5.3 | 6.4 | 1.2 |
| 2.056 | 106.6 | 12.7 | 48.7 | 26.5 |
| 2.057 | 6.2 | 1.3 | 3.7 | 0.7 |
| 2.058 | 15.3 | 2.8 | 3.3 | 0.6 |
| 2.059 | 3.9 | 0.3 | 2.7 | 0.2 |
| 2.060 | 4.9 | 0.3 | 3.2 | 0.1 |
| 2.061 | 10.5 | 3.2 | 1.8 | 0.4 |
| 2.062 | 63.4 | 25.1 | 30.5 | 2.2 |
| 2.063 | 206.2 | 88.8 | 73.9 | 3.5 |
| 2.064 | 4.1 | 1.8 | 2.2 | 0.4 |
| 2.065 | 4.1 | 1.4 | 1.8 | 0.2 |
| 2.066 | 10.2 | 3.4 | 2.3 | 0.4 |
| 2.067 | 19.6 | 5.8 | 4.2 | 0.5 |
| 2.068 | 8.0 | 2.0 | 5.8 | 0.4 |
| 2.069 | 16.7 | 4.9 | 2.4 | 0.3 |
| 2.070 | 285.9 | 122.0 | 48.4 | 6.1 |
| 2.071 | 21.2 | 2.7 | 11.9 | 0.5 |
| 2.072 | 7.5 | 1.4 | 4.4 | 0.5 |
| 2.073 | 12.7 | 2.6 | 4.2 | 0.4 |
| 2.074 | 133.3 | 31.1 | 36.4 | 7.7 |
| 2.075 | 123.0 | 25.7 | 21.7 | 1.5 |
| 2.076 | 8.0 | 1.8 | 2.4 | 0.3 |
| 2.077 | 33.7 | 12.5 | 5.0 | 0.8 |
| 2.078 | 18.3 | 4.4 | 2.6 | 0.0 |
| 2.079 | 18.5 | 5.5 | 2.3 | 0.2 |
| 2.080 | 213.7 | 18.5 | 125.9 | 17.7 |
| 2.081 | 1446.1 | 317.4 | 1111.2 | 989.8 |
| 2.082 | 131.7 | 30.1 | 9.0 | 2.9 |
| 2.083 | 1882.9 | 380.5 | 857.6 | 706.9 |
| 2.084 | 1174.6 | 172.9 | 349.6 | 116.2 |
| 2.085 | 2391.7 | 219.6 | 812.0 | 417.7 |
| 2.086 | 1246.0 | 57.7 | 358.0 | 28.5 |
| 2.087 | 896.4 | 67.0 | 59.3 | 6.2 |
| 2.088 | 38.7 | 6.1 | 13.6 | 1.6 |
| 2.089 | 102.1 | 3.7 | 32.9 | 3.1 |
| 2.090 | 53.3 | 10.2 | 19.5 | 2.4 |
| 2.091 | 776.1 | 94.2 | 236.7 | 16.1 |
| 2.092 | 1132.5 | 128.2 | 458.0 | 73.1 |
| 2.093 | 576.3 | 99.5 | 127.7 | 19.5 |
| 2.094 | 16570.6 | 1465.6 | | |
| 2.096 | 70.2 | 9.7 | 9.6 | 1.5 |
| 2.097 | 35.4 | 2.1 | 2.8 | 0.8 |
| 2.098 | 382.5 | 13.6 | 73.5 | 3.6 |
| 2.099 | 15.0 | | 3.8 | |
| fasudil | 346.3 | 17.6 | 96.4 | 6.4 |
| H-1152 | 18.5 | 5.3 | 2.0 | 0.3 |
| H7 | | | 124.7 | 5.6 |
| Y-27632 | 197.2 | 50.6 | 60.9 | 16.9 |
| Y-39983 | 34.7 | 11.1 | 3.6 | 0.9 |

Conclusion

Most of the compounds studied inhibited ROCK2 with a $K_i$ below 600 nM, many of these values below 60 nM. The most potent compounds in this assay showed $K_i$ values below 15 nM.

Example 2

Human Neutrophil Chemotaxis

Relevance

This assay is an in vitro assay of neutrophil chemotaxis that can be used to evaluate the ability of Rho Kinase inhibitor compounds of Formula I or II to inhibit the migration of human neutrophils, an inflammatory cell that has been implicated in the pathophysiology of cerebral ischemia and stroke.

Protocol

Peripheral blood from healthy human volunteers was collected and the neutrophils were isolated by Ficoll-paque density centrifugation followed by dextran sedimentation and hypotonic lysis of the red blood cells. Neutrophil chemotaxis was assessed using a modified Boyden Chamber (Neuroprobe, 96-well) with a 3 µm pore polycarbonate membrane. The ability of the tested compounds to block chemotaxis induced by a 1 µM fMLP challenge during a one hour incubation at 37° C. with 5% $CO_2$ was assessed in a dose response manner. The results are shown in Table 2.

Results

The results demonstrate that Rho Kinase inhibition by Formula I or II compounds inhibited human neutrophil migration toward a chemotactic stimulant in vitro with $IC_{50}$ potencies ranging from less than 1 µM to nearly 24 µM (Table 2)

TABLE 2

Inhibition of fMLP-induced neutrophil chemotaxis by Rho kinase inhibitors compounds of Formula I and/or II.

| Compound Number | Chemotaxis Avg. $IC_{50}$ (nM) | Chemotaxis SEM (nM) |
| --- | --- | --- |
| 2.038 | 734 | 367 |
| Y-39983 | 1,390 | 803 |
| 1.131 | 1,587 | 916 |
| 2.039 | 1,643 | 949 |
| 2.025 | 1,650 | 636 |
| 1.138 | 1,850 | 212 |
| 1.091 | 2,332 | 2,077 |
| 1.136 | 2,600 | 424 |
| 1.092 | 2,747 | 1,586 |
| 2.036 | 2,767 | 1,597 |
| 1.123 | 3,050 | 778 |
| 1.124 | 3,402 | 1,964 |
| 2.026 | 3,800 | 2,970 |
| H-1152 | 4,350 | 1,202 |
| 1.087 | 4,500 | 2,598 |
| 2.034 | 4,733 | 2,733 |
| 1.034 | 5,601 | 3,234 |
| 2.035 | 6,600 | 3,811 |
| Y-27632 | 6,765 | 1,747 |
| Fasudil | 23,800 | 13,741 |

Example 3

Carotid Artery Occlusion Model of Forebrain Ischaemia

Protocol

The following assay is useful for evaluating the effects of focal cerebral ischemia on morphological, neurological, and behavioral outcomes, and for evaluating potential therapeutic agents for anti-ischemic and anti-stroke activities. Cerebral infarcts in rats were produced with a silicone-coated 8-0 nylon filament inserted through the right carotid artery for 2 hr, followed by withdrawal of filament and reperfusion to induce permanent ischemia (Endres M, et al., *Proc Natl Acad Sci USA*. 95: 8880-8885, 1998; Rikitake Y, et al, *Stroke*. 36:2251-2257, 2005) Animals are anesthetized with halothane by a face mask. Regional cerebral blood flow and physiologic parameters are monitored using routine methodologies. (Huang, et al., *J. Cereb. Blood Flow Metab.* 16, 981-987, 1996). In randomly selected animals the left femoral artery is cannulated for arterial blood pressure and blood gas determination. Arterial blood samples are analyzed for pH, arterial oxygen pressure and partial pressure of carbon dioxide by using a blood gas/pH analyzer. Rectal temperature is maintained at 36.5±1° C. with a temperature control unit during the monitoring period. A variety of outcomes are measured 12-24 hr after initial reperfusion, including cerebral blood flow to both ischemic and non-ischemic brain areas, cerebral infarct size, neurological deficit scoring using standard methodologies. (Yamashita K, et al., *Brain Res.* 1154: 215-24, 2007; Rikitake Y, et al, *Stroke*. 36:2251-2257, 2005). Compounds are administered at up to 30 minutes before and after occlusion by a single i.p. injection at doses in the range of 1-100 mg/kg. Control animals receive i.p. injection of saline vehicle.

Results

At 12-24 hr following initial reperfusion, animals are evaluated for cerebral blood flow to both ischemic and non-ischemic brain areas, cerebral infarct size, and neurological deficit. Improvement in at least one of these outcomes is seen in compound-treated animals verse vehicle treated animals.

Example 4

Spinal Cord Injury Assay

The following spinal cord injury assay is useful to evaluate the effects of potential therapeutic agents in improving a variety of outcomes associated with spinal cord injury. BALB-c mice are anesthetized, and a segment of the thoracic spinal cord is exposed using fine rongeurs to remove the bone, and a dorsal over-hemisection is made at T7. (Dergham P et al. *The Journal of Neuroscience*, 22(15):6570-6577, 2002). The dorsal part of the spinal cord is cut such that the lesion extends past the central canal. A fibrin adhesive delivery system is prepared using a Tisseel VH kit. Lyophilized fibrinogen is reconstituted in an aprotinin solution; thrombin is reconstituted in a calcium chloride solution; and both solutions are warmed to 37° C. to allow polymerization. The thrombin solution is mixed with the fibrinogen solution just before application to the spinal cord to allow infiltration of the mixture in the lesion site before polymerization and the mixed solution forms a matrix that supports tissue repair. Dosing of compounds of this invention is done by mixing compounds in 50 µL of dosing solution containing compound at a concentration in the range 0.01-10 mg/mL with 25 µL of the thrombin solution. Control dosing involves mixing saline with thrombin solutions. For retransections 3 weeks after SCI, the spinal cords are cut at T6 as described above, and the animals are tested using the Basso-Beattie-Bresnahan (BBB) locomotor rating scale on days 1, 2, and 6 after the second surgery (Dergham P, et al., *The Journal of Neuroscience*, 22(15): 6570-6577, 2002).

Results

The measurable experimental outcomes include quantification of the regeneration length of axons in mice after SCI and behavior recovery as recorded using the BBB locomotor rating. Compound-treated mice show improvement in at least one of these outcome measures when compared with saline control.

Example 5

Animal Model of Neuropathy

This example illustrates the efficacy of compounds of Formula I or II in this invention in treatment of neuropathy in the rat.

Protocol

The model is created as in Fournier A E et al. *J Neurosci,* 23(4):1416-23, 2003. Adult female Sprague Dawley rats are maintained under standard conditions with free access to water and rodent laboratory feed. They are anesthetized with ketamine (60 mg/kg) and xylazine (10 mg/kg), laminectomy is performed at spinal levels T3 and T4, and the spinal cord is exposed. The dorsal half of the spinal cord is severed with microscissors at a depth of 1.5 mm. This is similar to spinal cord injury in the human (Mueller B K et al. *Nat Rev Drug Discovery,* 4(5): 387-98, 2005). An osmotic minipump (200 µl solution at 0.5 µl per hour over 2 weeks) filled with a Rho kinase inhibitor or PBS is sutured to muscles under the skin on the back of the rat. A catheter connected to the minipump is inserted into the intrathecal space of the spinal cord at T4 through the small hole in the dura. Two weeks later, a burr hole is made on each side of the skull overlying the sensimotor cortex of the lower limbs. The anterograde neuronal tracer BDA (10% biotin dextran amine in PBS, 4 µl total) is applied at 7 injection sites at 1, 1.5, and 2 mm depths from the cortical surface. Animals are sacrificed 2 weeks after BDA injection by intracardial perfusion of PBS followed by 4% Paraformaldehyde.

Histological Examination

Cryostat sections of the spinal cord through the lesion are cut parasagitally (50 µm). Transverse sections are collected from the spinal cord rostral and caudal to the site of injury. Sections are blocked in TBS with 0.5% BSA for 1 hour and then incubated for 2 d with avidin-biotin peroxidase in TBS with 0.15% BSA. Bound peroxidase is visualized with diaminobenzidine. The sections are mounted on coated slides for analysis.

Behavioral Analysis

Animals are given behavioral examinations prior to injury and at 2 d, and 1, 2 and 4 weeks after surgery. Animals are assessed on limb movement, weight support, forelimb-hindlimb coordination, paw rotation, toe clearance, trunk stability, and tail placement.

Results 4 weeks after injury, and 2 weeks after BDA injection, prepared sections of spinal cord of the injured area and surrounding tissue are analyzed, and those from the PBS group are compared with those from the Rho kinase inhibitor-treated group. Regenerative growth of axons in the dorsal grey matter and/or increased numbers of neural fibers in the dorsal white and grey matter is observed in the Rho kinase inhibitor-treated group when compared to the control group. Recovery of locomotor activity is accelerated in the Rho kinase inhibitor-treated group when compared to control.

Example 6

Animal Model of Nociceptive Pain

This example illustrates the efficacy of compounds in this invention in treatment of nociceptive pain in the mouse.

Protocol

The model is created as in Büyükafşar K et al. *Eur J Pharmacol,* 541(1-2):49-52, 2006. Male balb/c mice are housed under standard conditions with access to water and mice chow ad libitum. In the hot plate test, the mice are administered vehicle (saline) or compound of Formula I or II (1-100 mg/kg, i.p. injection) and are then placed on a hot plate apparatus, which is thermostatically maintained at 55±1° C. Latency is the time elapsed in seconds until the mouse licks its forepaws. The latency is recorded in control and treatment groups with a cut-off time of 30 s.

In the abdominal constriction response test, the mice are administered vehicle (saline) or Rho kinase inhibitor (1-10 mg/kg, i.p. injection). Thirty minutes later, 0.6% acetic acid is injected into the mice by the intraperitoneal route. Thereafter, each mouse is placed in an individual clear plastic observation chamber and the total number of writhes made by each mouse is counted for 15 min.

Results

Latency on the hot plate and number of writhes are compared between control animals and those treated with compounds of Formula I or II. Latency is increased and number of writhes is decreased in those animals treated with compounds of Formula I or II, demonstrating an antinociceptive effect.

Example 7

Animal Model Alzheimer's Disease Involving $A\beta_{42}$ Regulation

This example illustrates efficacy of compounds in this invention in treatment of Alzheimer's disease in mice.

Protocol 6-week old transgenic PDAPP mice are used in the experiments (Zhou Y et al. *Science,* 302: 1215-17, 2003). The animals are dosed by intracerebroventricular (ICV) injection. Mice are anesthetized and body temperature maintained at a consistent 37° C. The animals are placed in a stereotaxic apparatus with the incisor bar set at 3.3 mm below the interaural line. Small burr holes are made in the parietal bone to allow for the insertion of the injection cannula. All stereotaxic coordinates are determined based on the atlas of Paxinos and Watson. Brain levels of total $A\beta$ and $A\beta_{42}$ are measured 28 hours after injection. Other parameters which could be measured include histological analysis of the plaque volume area as well as memory retention.

Amyloid Extraction

Animals are euthanized and brain tissue is harvested. A total of 100 mg of brain tissue is homogenized in 1 mL of pure formic acid. Two microliters of the brain homogenate are used for the dot-blotting, or 50 µL are evaporated under nitrogen, solubilized in 50 µL of the SDS sample buffer (5% SDS, 20% glycerol, 2% β-mercaptoethanol, 150 mM Tris-HCl pH 6.8), and boiled 10 minutes before electrophoresis. A total of 10 µL (100 µg of protein) are loaded per well. Amyloid pathology is analyzed using electrophoresis adapted to the separation of small peptides. After the proteins are blotted on nitrocellulose membranes, the upper part is reacted with AD2 for the estimation of tau pathology. The lower part of the membranes is reacted first with ADA40 for the detection of $A\beta$ 40 and then, after stripping, with 21F12 or ADA42 for the detection of $A\beta_{42}$ species.

Plaque Volume Analysis

All animals are euthanized by a pentobarbital overdose and perfused with 4% paraformaldehyde. The brains are removed and coronal sections, 30 µm in thickness, are cut using a cryostat from the entire brain. Sections from the mouse brains are stained using appropriate antibodies and sections are examined under a light microscope; all consecutive sections throughout the plaque region are used to measure the plaque volume by an investigator blinded to the identity of the brains. Hemispheric areas for both sides of the tissue are measured to account for any brain swelling due to the stroke. Plaque volume is calculated in millimeters squared by multiplying the individual area measurements by the number of sections and by the distance between each section (Whitehead et al. *Stroke,* 38(12): 3245-3250, 2007).

Circular Platform Test

Memory and spatial learning behavioral skills are assessed using the Barnes circular platform pest. The behavioral test is divided into 3 phases: training, testing, and reacquisition phases. The time to reach the escape hole is measured as well as the number of errors (nose poked into wrong hole location). There are 3 recovery periods (7, 14, and 28 days after surgery), after which a single trial is performed with the hole at the initial training location (test). During the reacquisition phase, mice relearn the behavioral task (14 trials) with the hole location rotated by 135° (Whitehead et al. *Stroke,* 38(12): 3245-3250, 2007).

Dosing of Compounds of this Invention

Compounds of this invention are dosed via ICV injection at the dose of 0.1 mg/kg to 20 mg/kg of body weight. A control group of animals receive the same volume of vehicle.

Results

The ratio of $A\beta/A\beta_{42}$ levels in the brain, the plaque volume in the brain tissue and memory retention are measured and compared in the compound-treated mice vs. vehicle treated mice. An improvement in at least one of the above-mentioned endpoints is observed.

Example 8

Model of Experimental Autoimmune Encephalomyelitis in Mice

This assay of experimental autoimmune encyphalomyelitis (EAE) is a useful model of animal multiple sclerosis (MS) and is used to evaluate the effects of pharmacological agents on preventing or ameliorating the MS-like effects produced by the model.

Protocol

The strain of SJL/J mice (6-7 weeks old) is immunized with a proteolipid protein (PLP) peptide (200 μg emulsified in complete Freund's adjuvant containing heat-killed *mycobacterium tuberculosis*) by injection subcutaneously in both sides of the rear flank. 200 ng of pertussis toxin is given i.p. at the time of immunization and 48 hr later. This protocol gives rise to signs and symptoms of animal MS. Mice are weighed and examined for clinical signs of EAE and are scored from 0 to 5 for severity of EAE (0=normal, 1=limp tail; 2=impaired rightening reflex; 3=partial hind limb paralysis; 4=total hind limb paralysis; 5=moribund or death). (Sun X., et al., *J Neuroimmunol.* 180:126-134. 2006). Compounds of this invention are administered i.p. at dose range of 1-100 mg/kg/day beginning 4 days before immunization and/or for 14-42 days following immunization. Control animals are given i.p. vehicle injections at the same time of dosing of compound.

Histopathology and immunohistochemistry are conducted on mice with experimental EAE following anesthesia and perfusion with PBS and 4% paraformaldehyde. Spinal cords are collected on various days (beginning at day 14 and up to day 70) after antigen immunization. Routine fixation, paraffin embedding, and hemotoxylin-eosin staining techniques are used to evaluate spinal cord pathology and for the infiltration of inflammatory cells as graded by CF45 immunostaining. Percentages of demyelinated areas per total white matter areas are examined by myelin basic protein (MBP) staining and areas of axonal loss per total white matter area are examined by neurofilament immunostatining. Axonal transaction is evaluated by amlyoid precursor protein (APP) immunostaining and quantified by counting APP positive axons in a defined quarter of each section and calculated as positive axons per mm². Detailed protocol can be found in Sun X., et al., *J Neuroimmunol.* 180:126-134. 2006

Results

The following outcomes are evaluated in the murine model of EAE: (1) clinical signs of EAE (scored 1-5); (2) reduction of inflammatory cell infiltration; (3) attenuated demyelination; and (4) acute axonal transaction. Improvements in at least one of these outcomes are seen with compounds of this invention compared with vehicle treatment.

Example 9

NIH/3T3 Cell Morphology Assay

Relevance

The assay demonstrates that a compound's in vitro ROCK inhibition activity manifests itself in morphology changes, such as actin stress fiber disassembly and alteration in focal adhesions in intact cells leading to inhibition of acto-myosin driven cellular contraction. These morphology changes provide the basis for the beneficial pharmacological effects sought in the setting of the disease processes described in this application, specifically the disruption of the actin stress fibers and regulation of focal adhesions and its impact neuroremodeling and axonal/neurite retraction Protocol NIH/3T3 cells were grown in DMEM-H containing glutamine and 10% Colorado Calf Serum. Cells were passaged regularly prior to reaching confluence. Eighteen to 24 hours prior to experimentation, the cells were plated onto Poly-L-Lysine-coated glass bottom 24-well plates. On the day of experimentation, the cell culture medium was removed and was replaced with the same medium containing from 10 nM to 25 μM of the test compound, and the cells were incubated for 60 minutes at 37° C. The culture medium was then removed and the cells were washed with warmed PBS and fixed for 10 minutes with warmed 4% paraformaldehyde. The cells were permeabilized with 0.5% Triton-X, stained with TRITC-conjugated phalloidin and imaged using a Nikon Eclipse E600 epifluorescent microscope to determine the degree of actin disruption. Results were expressed as a numerical score indicating the observed degree of disruption of the actin cytoskeleton at the test concentration, ranging from 0 (no effect) to 4 (complete disruption), and were the average of at least 2 determinations.

All compounds tested show measurable activity in the cell morphology assay, with most of the compounds providing substantial effects (score of ≧2 at 1 μM) on the actin cytoskeleton at the tested concentration (see Table 3).

TABLE 3

Cell Morphology Assay Data

| Compound | Cell score at 1 μM |
|---|---|
| 1.002 | 1.4 |
| 1.004 | 1.8 |
| 1.005 | 1.3 |

TABLE 3-continued

Cell Morphology Assay Data

| Compound | Cell score at 1 μM |
|---|---|
| 1.006 | 2 |
| 1.008 | 2 |
| 1.024 | 2.4 |
| 1.025 | 2 |
| 1.034 | 2 |
| 1.039 | 2 |
| 1.041 | 2.5 |
| 1.046 | 2.5 |
| 1.048 | 1.5 |
| 1.051 | 2.5 |
| 1.052 | 2.8 |
| 1.062 | 2.3 |
| 1.066 | 2 |
| 2.002 | 1.8 |
| 2.006 | 2.8 |
| 2.008 | 1 |
| 2.016 | 1.8 |
| 2.017 | 2 |
| 2.018 | 1.8 |
| 2.026 | 2 |

Example 10

In Vivo Anti-inflammatory Activity

Relevance

The mouse ovalbumin sensitization model has been developed by investigators to study malfunctioning of the immune system, cellular infiltration composed primarily of eosinophils and neutrophils, acute and chronic inflammation and fluid accumulation (edema), especially in asthma. Although this model is mostly utilized in the context of asthma, this model is utilized to demonstrate the in vivo anti-inflammatory properties of Compounds of Formula I or II.

Protocol

Male BALB/c mice were ordered from Charles River Laboratories (Raleigh, N.C.). The animals were approximately 19 to 21 grams at time of receipt. Upon arrival, the animals were randomized into groups of five males per cage and assigned to a dosing group. Animals were quarantined for 7 days under test conditions. They were observed daily for general health status and ability to adapt to the water bottles. Animals were sensitized on day 0 and 14 of study by an intraperitoneal injection with 20 μg of ovalbumin (ova) and 2.0 mg aluminum hydroxide (alum) which initiates the development of a specific T-helper (Th) cells type 2 resulting in asthmatic animals (denoted as Ova in the figures). One group of animals received an injection of saline to use as control animals (denoted as normal in the figures). All animals were challenged with aerosolized 1% ova once daily for 25 minutes on days 28, 29, and 30 (Zosky, et al. *Respiratory Research*. 2004; 5:15). Aerosol challenge consists of using an Aerogen Aeroneb nebulizer and controller with a particle size of 4-6 μm mass median aerodynamic diameter (MMAD) with a distribution of 400 μl per minute. This aerosol challenge is necessary to target the Th2-driven allergic inflammation in the lower airways.

The anti-inflammatory dosing paradigm (FIG. 1) was utilized to evaluate the anti-inflammatory effects of experimental compounds. The anti-inflammatory dosing paradigm consists of dosing the animals once a day starting on day 27 and finishing on either day 30 or 31 (1 hr prior to the aerosolized ovalbumin challenges on days 28 to 30) but not on day 32 when hyperreactivity evaluation occurs (described in Example 11). On day 32 of the experiment, after measurement of airway hyperreactivity, BALF was collected and all animals were anesthetized, bled and euthanized.

Bronchoalveolar lavage fluid (BALF) was collected by infusing 3.0 ml of saline with 10% fetal calf serum into the lungs via the trachea and then withdrawing the fluid. The total amount of cells/ml of BALF fluid was determined via manual cell count on hemocytometer. The BALF was centrifuged, supernatant removed and analyzed for cytokine concentrations as described below, and cell pellet reconstituted in 500 μL of fluid. Cytospin slides were prepared from the cell pellet using 100 μL of fluid and spinning samples for 5 minutes at 5000 rpms in a cytospin centrifuge. Following Hema3 stain, relative percentages of individual leukocytes were determined on a 200 cell count for each sample. The final concentration of individual leukocyte cell types per ml of BALF was determined by multiplication of the relative percentage of individual leukocytes with the total amount of cells/ml of BALF fluid.

Figure 2:
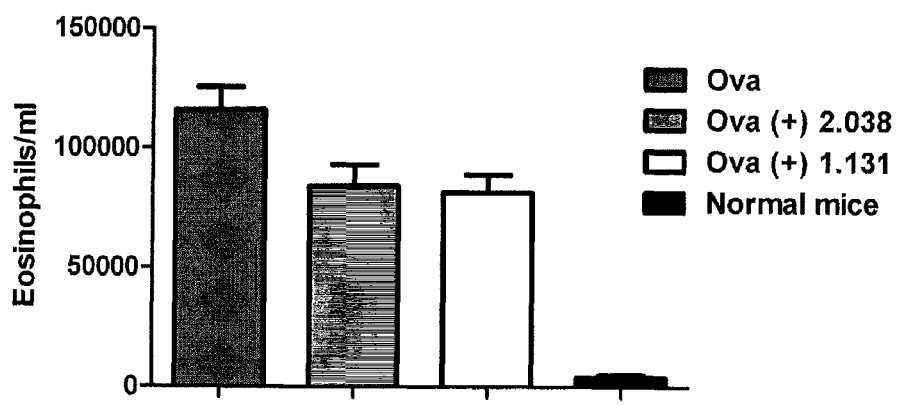
FIG. 2 shows the eosinophils per mL in ova-sensitized, ova-challenged mice treated with Compound 2.038, mice treated with Compound 1.131 and normal mice.
Figure 3:
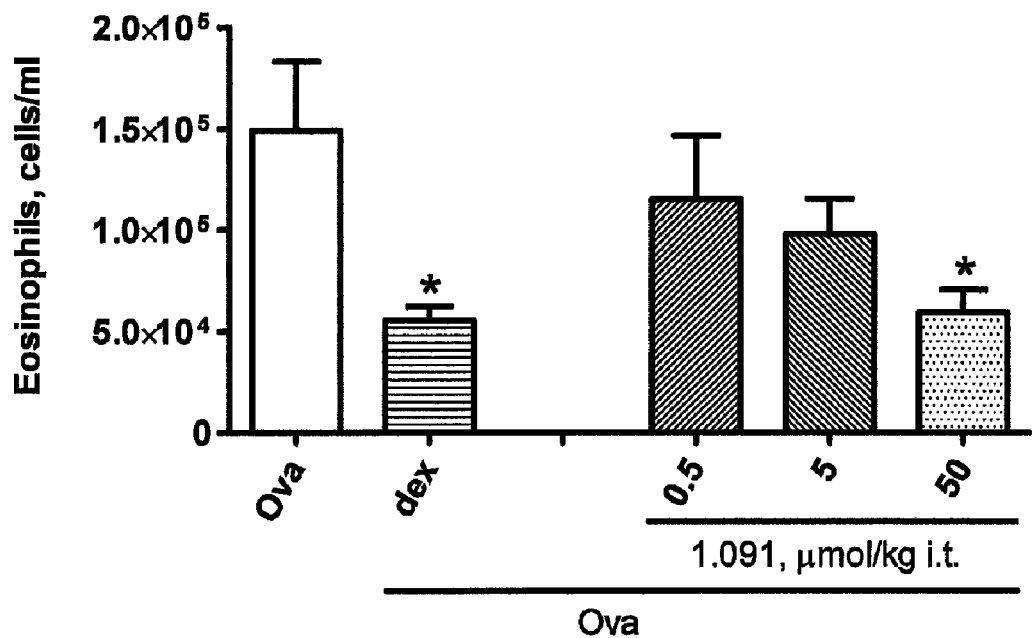
FIG. 3 shows the dose response effect of Compound 1.091 on eosinophil influx when dosed to ova-sensitized, ova-challenged mice, *, $p<0.05$ when compared to ova-sensitized, ova-challenged mice using Student's t-test.

Evaluation of the differential counts performed on these samples showed an increased number of inflammatory cells in the asthmatic animals. FIG. 2 shows the eosinophils per ml of BALF in asthmatic mice, mice treated with Compound 2.038, mice treated with Compound 1.131 and normal mice. Compounds were dosed orally to day 31 according to the anti-inflammatory dosing paradigm shown in FIG. 1. Airway eosinophil infiltration was reduced in animals treated with the two tested compounds (FIG. 2). As shown in FIG. 3, Compound 1.091 generates a reduction of eosinophils when dosed i.t. to day 30 according to the anti-inflammatory dosing paradigm shown in FIG. 1.

The concentrations of cytokines in the BALF samples were determined using commercially available Bio-plex kits (Bio-Rad) for the detection of mouse IL-5, IL-13, and Eotaxin. The analysis of cytokine levels was measured using the Bio-Plex 200 (Bio-Rad) system according to the manufacturer's instructions. Substantial evidence suggests that cytokines play an important role in orchestrating and regulating inflammatory processes through the involvement of T-helper type 2 lymphocytes.

Figure 4:
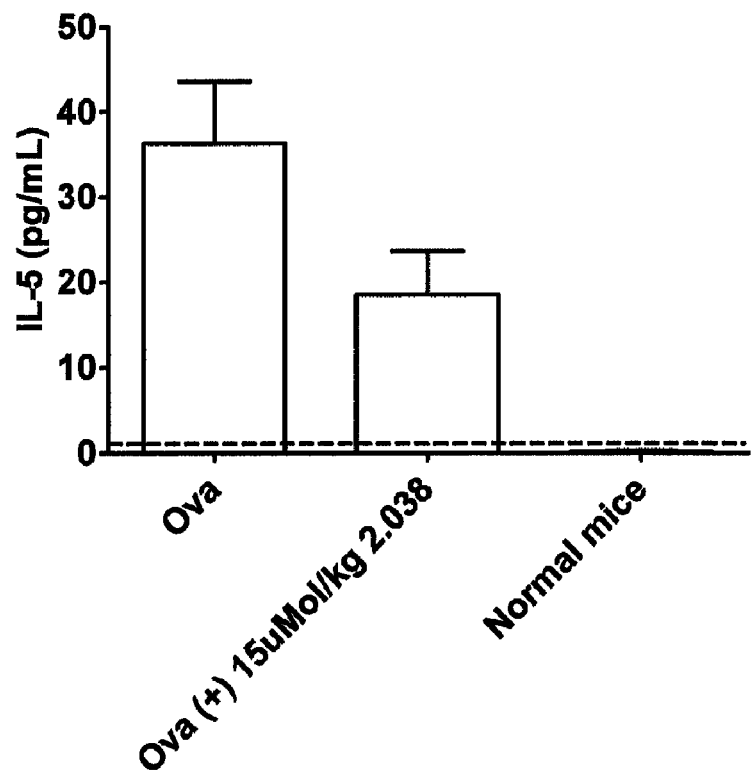
FIG. 4 shows the concentration of IL-5 (pg/mL) in BALF of (1) ova-sensitized, ova-challenged mice, (2) ova-sensitized, ova-challenged mice treated with Compound 2.038 (15 μmol/kg/oral), and (3) normal, saline-sensitized mice. Dashed line indicates the lower limit of detection for the cytokine of interest. Data represent mean±SEM, n=10 for ova-sensitized, ova-challenged mice, treated or untreated; n=5 for normal mice.
Figure 5:
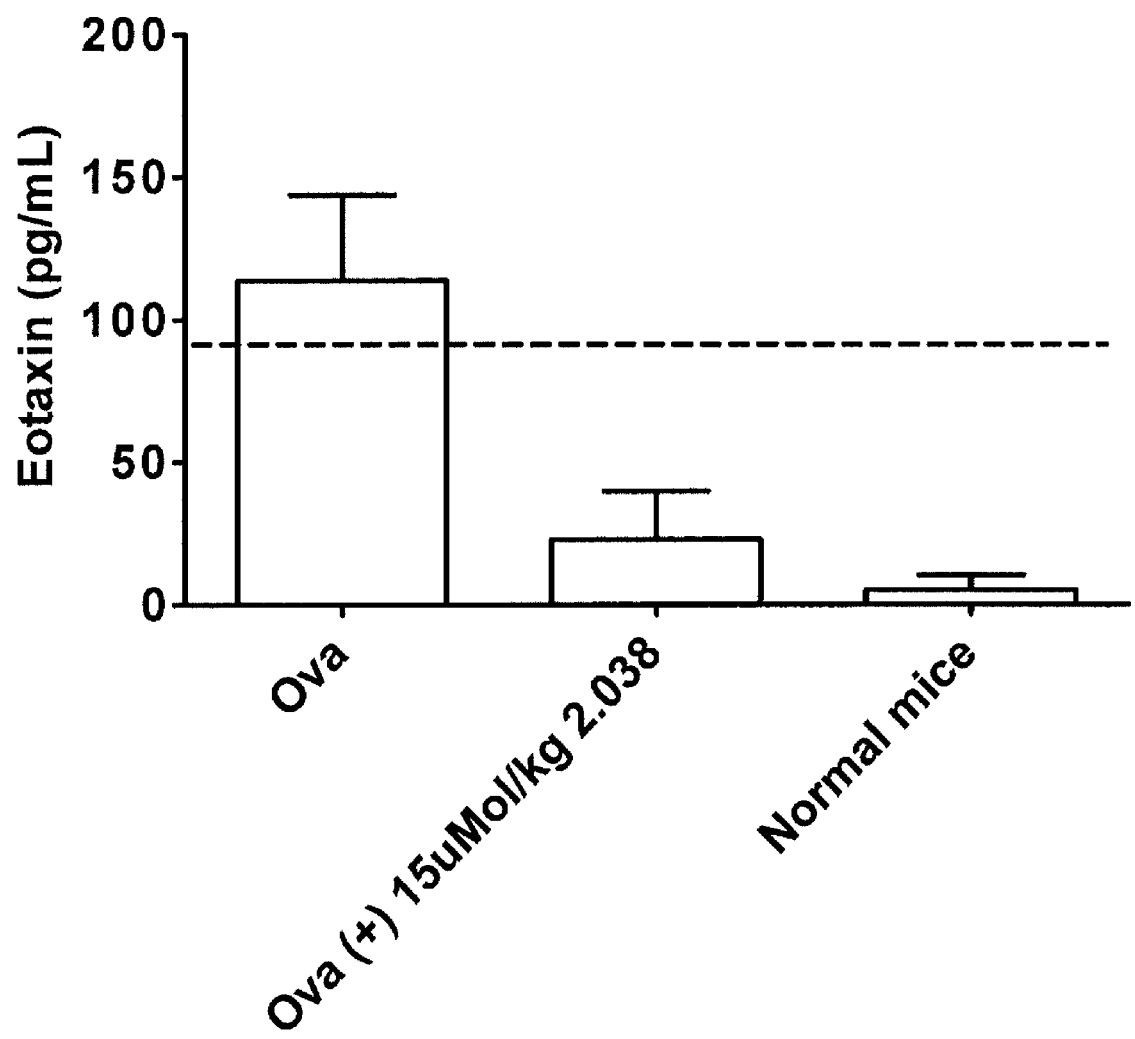
FIG. 5 shows the concentration of Eotaxin (pg/mL) in BALF of (1) ova-sensitized, ova-challenged, (2) ova-sensitized, ova-challenged mice treated with Compound 2.038 (15 μmol/kg/oral), and (3) normal, saline-sensitized mice. Dashed line indicates the lower limit of detection for the cytokine of interest. Data represent mean±SEM, n=10 for ova-sensitized, ova-challenged mice, treated or untreated; n=5 for normal mice.
Figure 6:
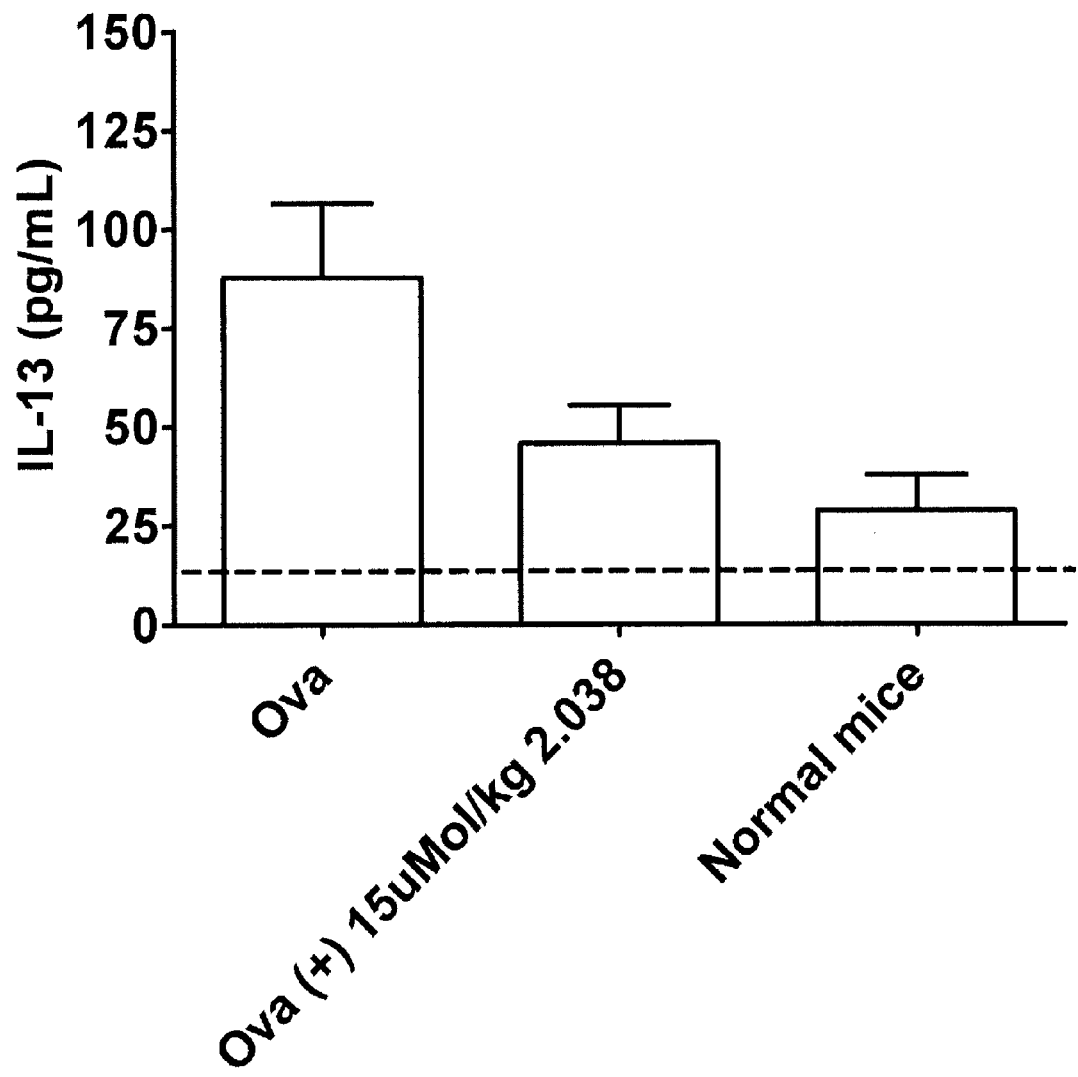
FIG. 6 shows the concentration of IL-13 (pg/mL) in BALF of (1) ova-sensitized, ova-challenged, (2) ova-sensitized, ova-challenged mice treated with Compound 2.038 (15 μmol/kg/oral), and (3) normal, saline-sensitized mice. Dashed line indicates the lower limit of detection for the cytokine of interest. Data represent mean±SEM, n=10 for ova-sensitized, ova-challenged mice, treated or untreated; n=5 for normal mice.

FIGS. 4-6 show the concentration of IL-5, Eotaxin, and IL-13 in (1) ova-sensitized, ova-challenged mice, (2) ova-sensitized, ova-challenged mice treated with Compound 2.038 (15 μmol/kg/oral on days 27 to 31), and (3) normal, saline-sensitized mice. The results showed that ova-sensitized, ova-challenged mice treated with Compound 2.038 had reduced levels of IL-5, Eotaxin, and IL-13.

Example 11

Prevention of Airway Hyperreactivity Development Via Decrease in Inflammation Relevance Airway hyperreactivity is a downstream physiologic effect of inflammation in the mouse ovalbumin sensitization model. The objective of the experiment was to answer whether the decrease in inflammation due to ROCK inhibitor anti-inflammatory dosing results in the prevention of downstream physiological consequences as measured by Penh. Although this concept is demonstrated in a model of airway hyperreactivity due to pulmonary inflammation, these data support the general use of these compounds as anti-inflammatory agents to prevent the downstream physiological consequences of inflammation in an in vivo model.

Protocol

Mouse model of ovalbumin sensitization was created as described in Example 10, The anti-inflammatory dosing paradigm (FIG. 1) was utilized to evaluate the prevention of airway hyperreactivity due to the anti-inflammatory effects of experimental compounds. The anti-inflammatory dosing paradigm consists of dosing the animals once a day starting on day 27 and finishing on either day 30 or 31 (1 hr prior to the aerosolized ovalbumin challenges on days 28 to 30) but not on day 32 when hyperreactivity evaluation occurs. On day 32 of the experiment, airway hyperreactivity was evaluated by placing conscious, unrestrained animals in a whole body plethysmometer (Buxco Wilmington, N.C.) and exposing them to escalating doses of nebulized methacholine, a known bronchial constrictor which acts through the muscarinic receptors of the lungs, (doses: 0.325-50 mg/ml). Exposure to the methacholine doses consisted of a 3 minute period during which a nebulizer was aerosolizing the methacholine and an additional 3 minute period following the cessation of nebulization. Over this 6 minute period, the plethysmometer monitors and generates numerical values for all parameters of the breath pattern. Enhanced pause (Penh), a unitless index of airway hyperreactivity, is derived from the expiratory side of the respiratory waveform measured via the plethysmograph and is used as an indirect measure of airway resistance and hyperreactivity. Penh is an indicator of changes in resistance within the airways and has been shown to be a valid marker for airway responsiveness to allergen challenge (Hamelmann, et al. *Am J Respir Crit Care Med.* 1997; 156:768-775). Following the methacholine dose response, BALF was collected and all animals were anesthetized, bled and euthanized.

Statistical Methods

Within each experiment, a mouse was given a single compound and exposed to increasing doses of methacholine [0 (baseline), 0.375, 0.75, 1.5, 3, 6, 12, 25, 50 mg/ml]. The Penh value at each of the dose levels of methacholine represents the 6-minute average response. Change from baseline (CFB) in Penh was calculated at each methacholine dose and the area under the curve (AUC) for these CFB values was calculated using the trapezoidal rule. This same approach was applied for each mouse across multiple experiments.

For statistical analyses, a linear mixed-effects model where the response was the log 10 transformed value of AUC described above was used. Data from equal experimental conditions across experiments performed on different days were pooled for statistical analysis and data reporting. The various compounds were compared adjusting for the log 10-transformed baseline value of Penh and the chamber (1 of 10) of the plethysmometer each mouse was contained in during an experiment. A random intercept for each experiment was assumed to account for possible similarities of the results obtained from a given experiment (i.e., as a "blocking effect"). Pairwise comparisons of the compounds were performed using approximate t-tests to test the null hypothesis of no compound difference of the least-squares means of log 10(AUC). p values of less than 0.05 were considered statistically significant Computations were performed using PROC MIXED (SAS Version 9.1).

For Table 4, Penh values are reported as log 10 transformed AUC values. For FIG. 7, linear AUC values from compound treated mice were reported as a percent of linear AUC values from vehicle-treated ovalbumin-sensitized/ovalbumin-challenged (asthmatic) mice.

Figure 7:
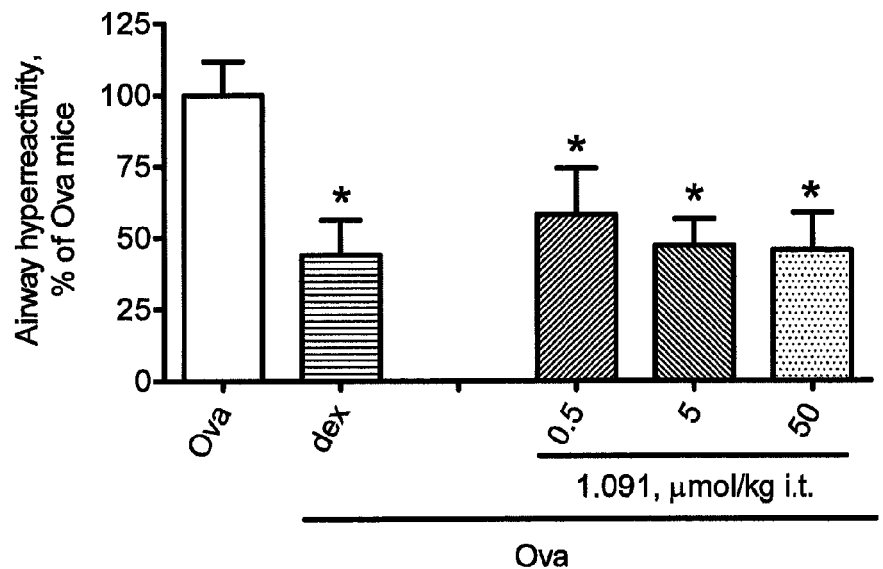
FIG. 7 shows the dose response effect of Compound 1.091 on airway hyperreactivity when dosed using the anti-inflammatory dosing paradigm on Days 27 to 30. *, $p<0.05$ using statistical analysis described in Example 11.

The oral administration of 15 μMol/kg of Compound 1.131 or 2.038 once a day during days 27 to 31 resulted in prevention of airway hyperreactivity to metacholine dosed on Day 32 (Table 4). As shown in FIG. 7 and Table 4, intratracheal administration of Compound 1.091 once a day during days 27 to 30 (FIG. 7) or Compounds 1.161, 2.066 or 2.059 once a day during days 27 to 31 (Table 4) according to the anti-inflammatory dosing paradigm shown in FIG. 1 resulted in prevention of airway hyperreactivity. Compound 1.091, 1.161, 2.066 or 2.059 had similar efficacy to dexamethasone, a corticosteroid anti-inflammatory control. These data support the use of these compounds to prevent the downstream physiologic consequences of inflammation.

TABLE 4

Anti-inflammatory dosing: Statistical Analysis of the AUC for Average Penh Values Determined During Experiment Normalized to Baseline for Each Animal

|  | Dosing concentration/ route of administration | Number of animals per group | log10A UC (Penh) | Standard Error | Student t-test p-value |
|---|---|---|---|---|---|
| asthmatic | Vehicle/oral | 70 | 2.3354 | 0.04751 |  |
| 1.131 | 15 μmol/kg/oral | 10 | 2.0674 | 0.1061 | 0.0133 |
| 2.038 | 15 μmol/kg/oral | 20 | 1.8981 | 0.07966 | <0.0001 |
| 1.161 | 0.5 μmol/kg/ intratracheal | 10 | 2.0405 | 0.1083 | 0.0077 |
| 2.066 | 0.5 μmol/kg/ intratracheal | 10 | 2.0248 | 0.1091 | 0.0055 |
| 2.059 | 0.5 μmol/kg/ intratracheal | 10 | 1.9979 | 0.1084 | 0.0024 |
| Y-27632 | 30 μmol/kg/oral | 10 | 1.9942 | 0.1062 | 0.0017 |
| Dexamethasone | 1 mg/kg/oral | 30 | 2.0216 | 0.06546 | <0.0001 |
| non-asthmatic | Vehicle/oral | 20 | 1.7810 | 0.07973 | <0.0001 |

Compounds were administered on days 27 to 31 according to the anti-inflammatory dosing paradigm. The t-test was conducted for the comparison of compound-treated to vehicle-treated "asthmatic groups" based on the vehicle which was run in every study.

Example 12

IL-1β Monocyte Secretion Assay

Relevance

This assay is an in vitro assay of cytokine secretion that can be used to evaluate the ability of Rho Kinase inhibitor compounds of Formula I or II to inhibit cytokine secretion, as the secretion of cytokines contributes to inflammation. Efficacy of compounds in this assay supports the use of these compounds to treat disease associated with inflammation.

Protocol

Peripheral blood from healthy human volunteers was collected and the monocytes isolated via Ficoll-paque density centrifugation. The resultant pellet was re-suspended in media containing 1 ng/mL lipopolysaccharide (LPS) and plated at a density of 500,000 cells/mL. After 3 hours of incubation (37° C., 5% $CO_2$, humidified air), monocytes were selected by adherence to the tissue culture plastic by washing wells with media. Following the media wash, cells were incubated for 2 minutes with the Rho Kinase inhibitors (10 μM) prior to the addition of 1 mM ATP. Cells were allowed to incubate with compounds for 30 minutes at 37° C. after which the supernatant was removed for immediate determination of IL-1β concentration. The concentration of IL-1β in cell supernatants was measured using the Human IL-1β kit and Bio-Plex system (Bio-Rad) according to manufacture's instructions.

157

Results

Figure 8:
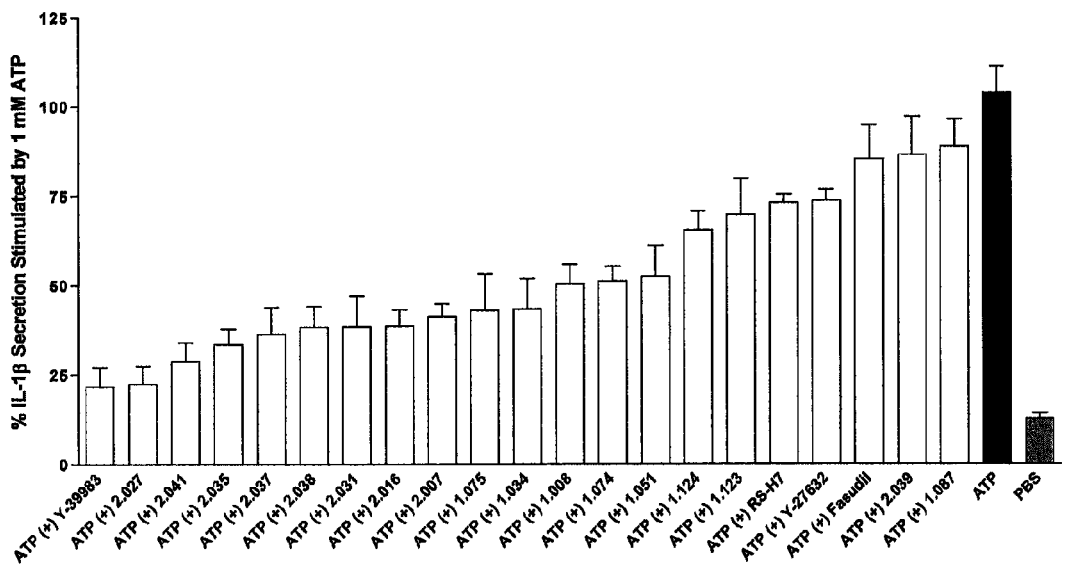
FIG. 8 shows the % inhibition of IL-1β Secretion in Human Monocytes by Rho Kinase Inhibitors. Data represent the mean±SD of at least n=2 experiments.

FIG. 8 shows percent inhibition of IL-1β secretion in human monocytes by Rho Kinase inhibitors Compounds of Formula I or II. The tested Rho Kinase inhibitors Compounds of Formula I or II at a 10 μM concentration demonstrated a varying efficacy range. Many compounds effectively reduced IL-1β secretion to low levels. A few compounds showed little effect on decreasing the ATP stimulated release of IL-1β.

Example 13

Human and Murine Eosinophil Chemotaxis

Relevance

These assays are in vitro assays of eosinophil chemotaxis that can be used to evaluate the ability of Rho Kinase inhibitor compounds of Formula I or II to inhibit the migration of eosinophils, an immunomodulatory cell involved in inflammation. Compounds with activity in this assay can be utilized to treat disease associated with an inflammatory response.

Protocol

Human Eosinophil Isolation: Peripheral blood from healthy human volunteers was collected and the PMNs separated via Ficoll-paque density centrifugation followed by hypotonic lysis of the red blood cells. Subsequently, the human eosinophils were isolated from the cell suspension via StemCell Technologies Human Eosinophil Enrichment kit (Cat. No 19256) according to the manufacturer's recommendations. Briefly, unwanted cells were specifically labeled with dextran-coated magnetic nanoparticles using bispecific Tetrameric Antibody Complexes (TAC) directed against cell surface antigens on human blood cells: CD2, CD3, CD14, CD16, CD19, CD20, CD36, CD56, CD123, glycophorin A and dextran. The unwanted cells are then separated from the unlabelled eosinophils using the EasySep® magnetic isolation procedure.

Mouse Eosinophil Isolation: Bronchoalveolar lavage was collected from ovalbumin sensitized and challenged mice in a volume of 2.5 mL lavage buffer. The lavage buffer was 0.9% saline with 10% fetal bovine serum. The pooled lavages were maintained on ice until use. The murine eosinophils were isolated using MACS cell separation (Miltenyi Biotech) by depletion of B cells and T cells by positive selection following incubation with antibody conjugated magnetic beads specific for CD45-R (B220) and CD90 (Thy 1.2), which bind B cells and T cells, respectively.

In Vitro Chemotaxis: Eosinophil chemotaxis was assessed using a modified Boyden Chamber (Neuroprobe, 96-well) with a 5 μm pore membrane. The ability of the tested compounds to block chemotaxis induced by a 10 nM eotaxin challenge (mouse) or 1 nM eotaxin challenge (human) during one hour incubation at 37° C. with 5% $CO_2$ was assessed.

Results

Figure 9:
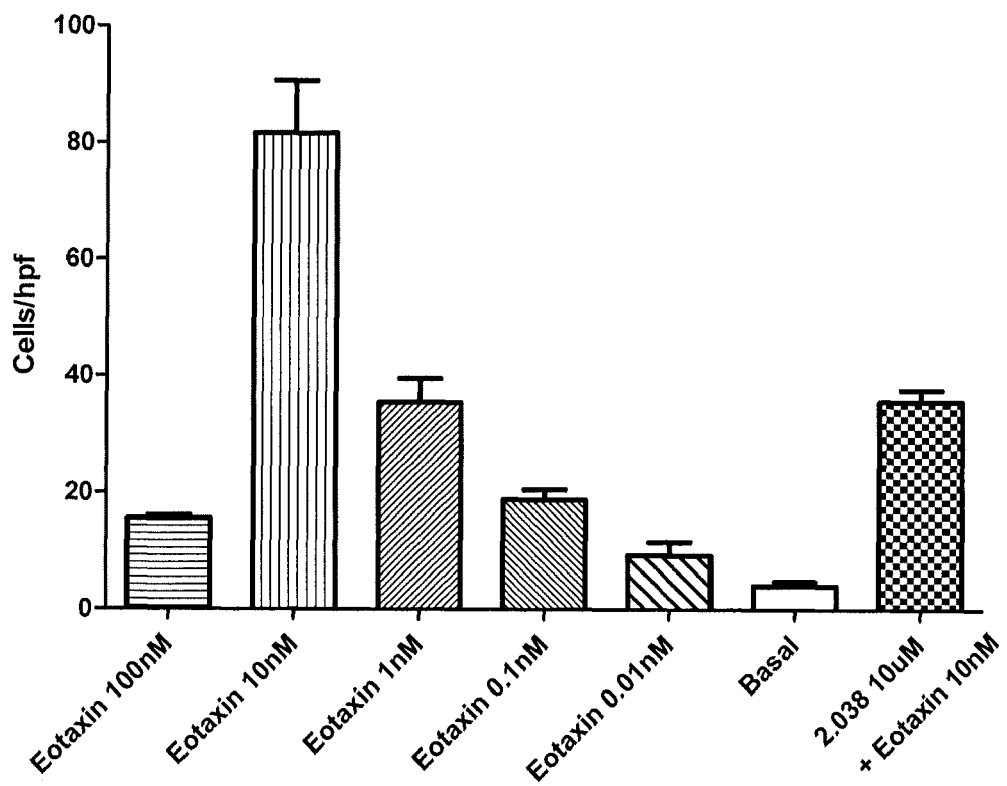
FIG. 9 shows the murine eosinophil chemotaxis. The data reported are mean number of migrated eosinophils per high power view field ±SEM. Average of at least 2 view fields per well, each treatment ran in triplicate.
Figure 10:
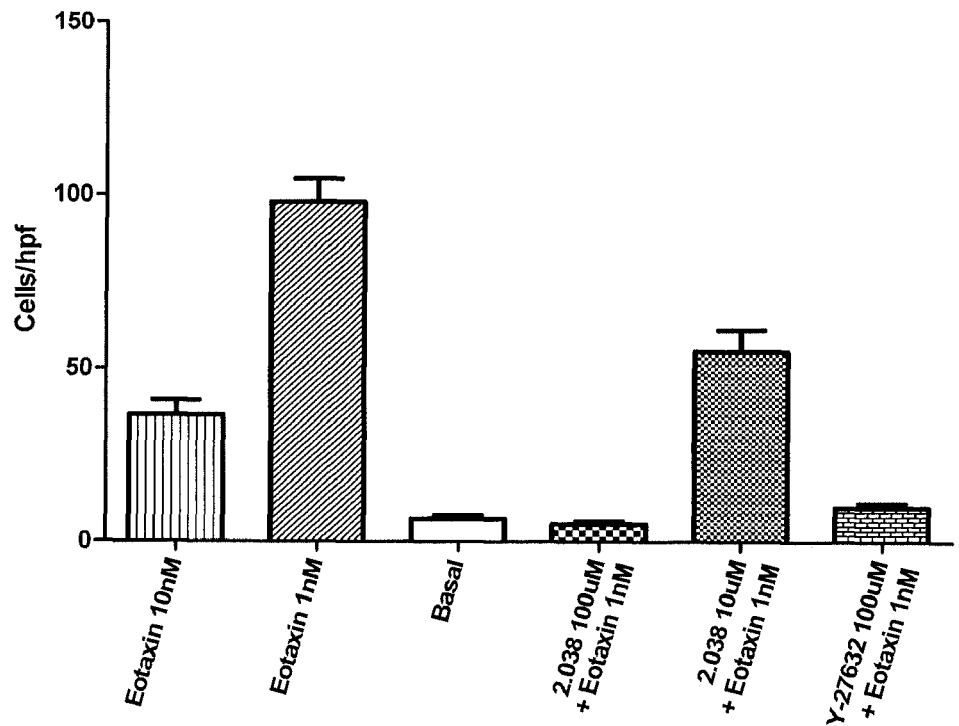
FIG. 10 shows the human eosinophil chemotaxis. The data reported are mean number of migrated eosinophils per high power view field ±SEM. Average of at least 3 view fields per well, each treatment ran in duplicate.

Chemotaxis was quantified via microscopy by counting the number of migrated cells in at least 3 view fields per treatment. The results are shown in FIGS. 9 and 10. FIG. 9 demonstrates that chemotaxis was induced by eotaxin in murine eosinophils; the chemotactic response was subsequently inhibited by Rho Kinase inhibitor Compound 2.038. FIG. 10 demonstrates that chemotaxis was induced by eotaxin in human eosinophils. The chemotactic response was subsequently inhibited by Rho Kinase inhibitor Compound 2.038.

Example 14

Human Monocyte Cytokine Secretion Assay

Relevance:

This assay demonstrates a compound's ability to inhibit the secretion of multiple pro-inflammatory cytokines from human monocytes. Reduction in the levels of pro-inflammatory cytokines is associated with improvement in disorders with an inflammatory component.

Protocol

Peripheral blood from healthy human volunteers was collected and the monocytes isolated via Ficoll-paque density centrifugation. Monocytes were purified via an Easy Sep© Monocyte Enrichment Kit (Product number 19059) according to the manufacturer's instructions. The purified monocytes were then plated in 96-well plates at a density of 300,000 cells/mL in RPMI 1640+10% heat inactivated FBS media. The cells were allowed to pre-incubate with test compound at the indicated concentration for 30 minutes (37° C., 5% $CO_2$, humidified air); after which the supernatant was removed and media containing compound and 1 ng/mL LPS was added. Cells were allowed to incubate with compounds and LPS for 4 hours at 37° C. after which the supernatant was removed and stored at −80° C. Cytokine concentrations in the supernatant were determined using commercially available Bio-Rad Bio-plex™ kits according the manufacturer's instructions.

Results:

Compounds of Formula I and II inhibit the release of multiple cytokines from human monocytes when incubated at 10 μM concentration in vitro, as shown in Table 5. Shown further in Table 6, potency determinations on compounds 2.059 and 2.066, both potent inhibitors of ROCK1 and ROCK2 and both of the chemical class in which $R_2$ is $R_2$-2, dose-dependently reduced the secretion of IL-1β, TNF-α and IL-9 from LPS-stimulated human monocytes, with potencies ranging from approximately 170 nM to 1 μM.

TABLE 5

Percent inhibition values for inhibition of cytokine secretion at 10 μM of test compound

| Compound | IL-1β % | IL-6 % | TNF-α % |
| --- | --- | --- | --- |
| 1.072 | 98.2 | 96.1 | 83.8 |
| 1.074 | 43.9 | 96.0 | 87.7 |
| 1.075 | 49.7 | 73.9 | 51.6 |
| 1.076 | 51.0 | 81.2 | 78.9 |
| 1.077 | 30.3 | 43.3 | 52.3 |
| 1.078 | 60.4 | 111.0 | 88.1 |
| 1.079 | 59.3 | 31.1 | 56.5 |
| 1.091 | 165.5 | 108.2 | 104.6 |
| 1.093 | 109.0 | 49.7 | 76.1 |
| 1.106 | 121.5 | 95.0 | 80.6 |
| 1.107 | 111.3 | 122.1 | 83.1 |
| 1.108 | 131.3 | 89.8 | 116.7 |
| 1.109 | 190.5 | 312.9 | 118.3 |
| 1.110 | 133.6 | 111.7 | 118.6 |
| 1.123 | 82.6 | 64.7 | 62.7 |
| 1.124 | 99.5 | 101.4 | 61.5 |
| 1.127 | 198.0 | 67.3 | 97.3 |
| 1.131 | 48.3 | 68.6 | 85.2 |
| 1.132 | 58.6 | 72.5 | 80.3 |
| 1.133 | 54.5 | 70.7 | 66.2 |
| 1.134 | 43.2 | 74.6 | 69.1 |
| 1.135 | 57.0 | 123.2 | 108.0 |
| 1.136 | 66.3 | 95.0 | 71.5 |
| 1.137 | 40.3 | 46.2 | 58.0 |
| 1.138 | 257.4 | 76.6 | 130.9 |
| 1.141 | 50.4 | 71.7 | 75.7 |

TABLE 5-continued

Percent inhibition values for inhibition of cytokine secretion at 10 μM of test compound

| Compound | IL-1β % | IL-6 % | TNF-α % |
|---|---|---|---|
| 1.142 | 82.8 | 40.7 | 68.6 |
| 1.143 | 76.8 | 130.5 | 66.4 |
| 1.145 | 129.2 | 95.1 | 88.9 |
| 1.146 | 85.2 | 128.0 | 97.7 |
| 1.148 | 63.9 | 78.6 | 56.1 |
| 1.149 | 69.8 | 121.5 | 119.9 |
| 1.150 | 78.2 | 89.2 | 94.4 |
| 1.151 | 84.5 | 114.1 | 88.9 |
| 1.152 | 74.7 | 94.7 | 120.1 |
| 1.153 | 64.1 | 106.2 | 74.3 |
| 1.154 | 52.3 | 104.4 | 86.4 |
| 1.155 | 76.7 | 121.8 | 79.7 |
| 1.156 | 60.7 | 92.5 | 70.5 |
| 1.157 | 121.4 | 92.6 | 65.1 |
| 1.158 | 80.8 | 133.1 | 86.6 |
| 1.159 | 97.1 | 84.8 | 76.1 |
| 1.161 | 87.7 | 86.3 | 153.5 |
| 1.162 | 95.5 | 99.8 | 158.7 |
| 1.163 | 166.7 | 140.9 | 91.6 |
| 1.164 | 80.1 | 109.5 | 89.0 |
| 1.165 | 129.9 | 114.3 | 103.5 |
| 1.166 | 107.0 | 87.2 | 82.2 |
| 1.170 | 80.6 | 72.7 | 67.8 |
| 1.171 | 78.9 | 91.8 | 72.2 |
| 1.173 | 86.1 | 79.5 | 80.1 |
| 1.175 | 29.3 | 38.2 | 47.4 |
| 1.176 | 95.2 | 112.4 | 72.4 |
| 1.183 | 68.7 | 123.3 | 76.5 |
| 1.185 | 39.8 | 63.0 | 66.6 |
| 1.186 | 64.1 | 105.3 | 68.2 |
| 1.195 | 115.4 | 94.4 | 67.7 |
| 1.197 | 179.1 | 128.8 | 83.3 |
| 1.200 | 0.0 | 0.0 | 0.2 |
| 1.206 | 88.7 | 164.0 | 97.3 |
| 1.208 | 62.0 | 109.0 | 92.0 |
| 1.212 | 116.3 | 111.0 | 108.1 |
| 1.213 | 111.1 | 81.7 | 77.4 |
| 1.215 | 136.7 | 63.2 | 60.4 |
| 1.217 | 118.6 | 73.8 | 71.3 |
| 1.219 | 138.9 | 127.7 | 82.1 |
| 1.223 | 117.0 | 88.5 | 60.7 |
| 1.226 | 99.3 | 52.2 | 66.6 |
| 1.227 | 69.4 | 66.7 | 79.3 |
| 1.229 | 44.9 | 63.2 | 50.7 |
| 1.233 | 78.5 | 78.9 | 79.0 |
| 1.236 | 75.2 | 93.0 | 98.0 |
| 1.237 | 97.1 | 100.9 | 70.6 |
| 1.238 | 101.1 | 62.9 | 73.2 |
| 1.239 | 39.4 | 84.7 | 58.5 |
| 1.246 | 103.0 | 108.3 | 79.0 |
| 1.249 | 133.8 | 56.2 | 60.0 |
| 1.252 | 139.2 | 68.3 | 101.6 |
| 1.253 | 160.6 | 228.6 | 126.8 |
| 1.258 | 104.1 | 83.5 | 94.0 |
| 1.262 | 145.7 | 156.6 | 135.3 |
| 2.026 | 166.0 | 180.7 | 109.1 |
| 2.031 | 49.0 | 89.3 | 66.4 |
| 2.038 | 90.8 | 79.7 | 70.2 |
| 2.039 | 49.8 | 70.3 | 47.8 |
| 2.054 | 24.0 | 56.8 | 37.9 |
| 2.058 | 1.2 | 1.3 | 10.6 |
| 2.059 | 0.3 | 0.0 | 6.9 |
| 2.060 | 5.9 | 19.6 | 33.0 |
| 2.064 | 14.3 | 45.7 | 66.2 |
| 2.066 | 0.0 | 0.0 | 25.2 |

TABLE 6

IC$_{50}$ values for inhibition of cytokine secretion

| | IL-1β (nM) | TNF-α (nM) | IL-9 (nM) |
|---|---|---|---|
| Compound 2.059 | 169.4 ± 13.0 | 207.1 ± 17.0 | 268.6 ± 28.1 |
| Compound 2.066 | 346.2 ± 182.3 | 610.6 ± 154.1 | 934.9 ± 407.5 |

Example 15

LPS-induced Neutrophilia and Cytokine Production Assay

Relevance

Marked neutrophilia can occur upon tissue inflammation. The LPS-induced neutrophilia model is often used to determine the potential efficacy of therapeutic approaches to limit inflammatory responses. This assay is an in vivo assay of neutrophil accumulation and cytokine production that can be used to evaluate the activity of Rho Kinase inhibitor compounds of Formula I or II as anti-inflammatory agents in a whole animal model. Neutrophil accumulation and cytokine production are indicative of an inflammatory response and the activity of compounds to decrease neutrophil accumulation and cytokine production in this assay supports the use of these compounds to treat disorders with an inflammatory component.

Protocol

Male BALB/c mice, approximately 19 to 21 grams, were ordered from Charles River Laboratories (Raleigh, N.C.). All animals were challenged with aerosolized LPS (10 μg/ml) for 25 minutes on study day 0. LPS aerosol was generated using an Aerogen Aeroneb nebulizer and controller providing a flow of 400 μl/min and a particle size of 2-4 μm MMAD. Rolipram was administered i.p at 20 mg/kg. Compound 1.091 or Compound 2.059 was administered intratracheally (i.t.) at 0.5-50 μmol/kg body weight one hour prior to LPS challenge. Four hours following LPS challenge, BALF was collected using a total of 3 ml of 0.9% sodium chloride containing 10% fetal calf serum. Total cell counts were determined using the Coulter Counter. For differential evaluations, BALF was centrifuged and cytospin slides prepared and stained with Hema3 stain. Manual leukocyte counts were then completed on 200 cells. The final concentration of individual leukocyte cell types per ml of BALF was determined by multiplication of the relative percentage of individual leukocytes with the total amount of cells/ml of BALF fluid. The concentration of IL-1β in the BALF samples was determined using commercially available Bio-plex kits (Bio-Rad). The analysis of cytokine levels was measured using the Bio-Plex 200 (Bio-Rad) system according to the manufacturer's instructions.

Results

Figure 11:
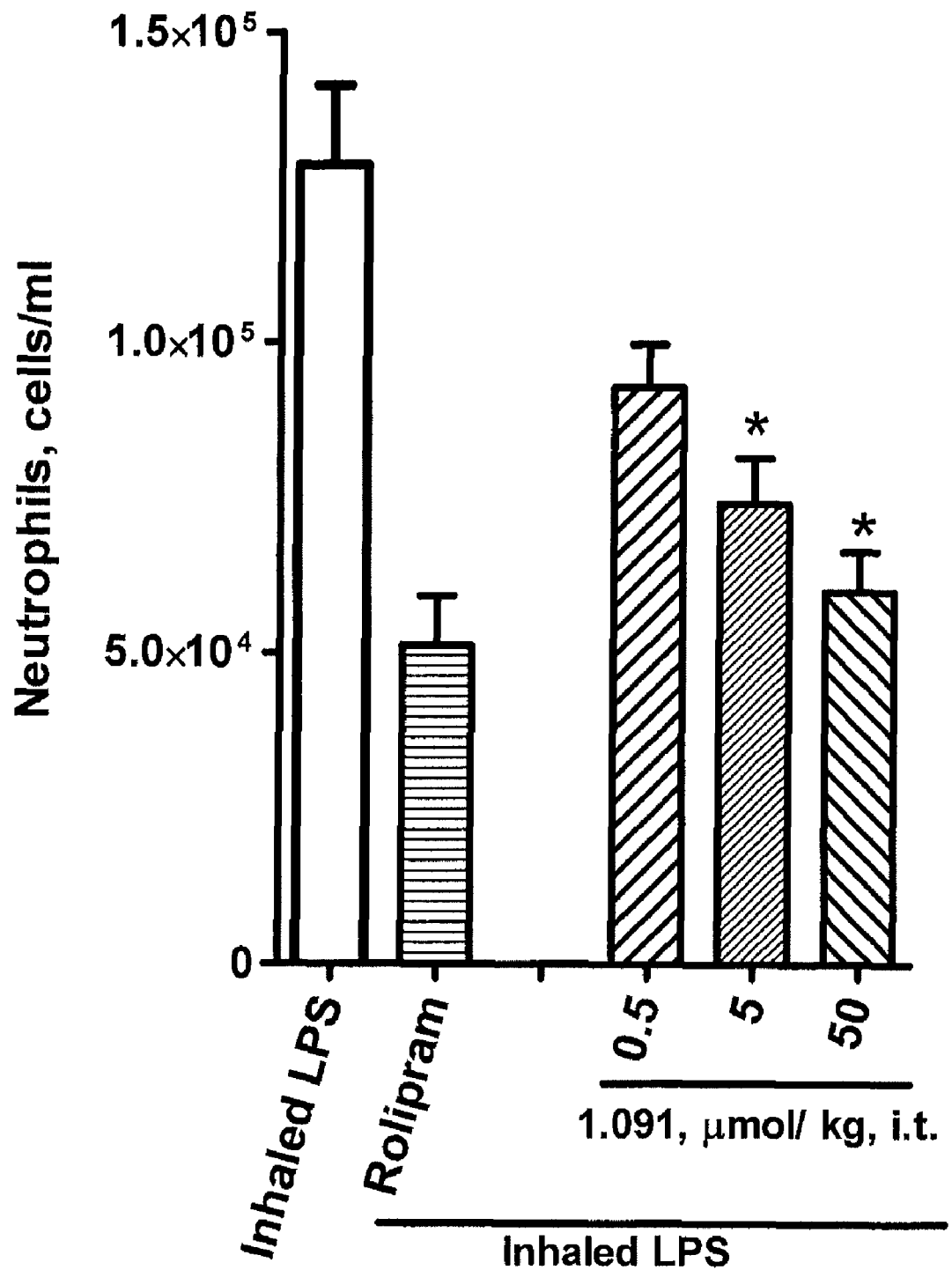
FIG. 11 shows the dose-dependent inhibition of LPS-induced neutrophilia by Compound 1.091 when dosed intratracheally to mice. Data are reported as cells/ml and are mean±SEM. *, $p<0.05$ when compared to mice treated with LPS alone using Student's t-test.
Figure 12:
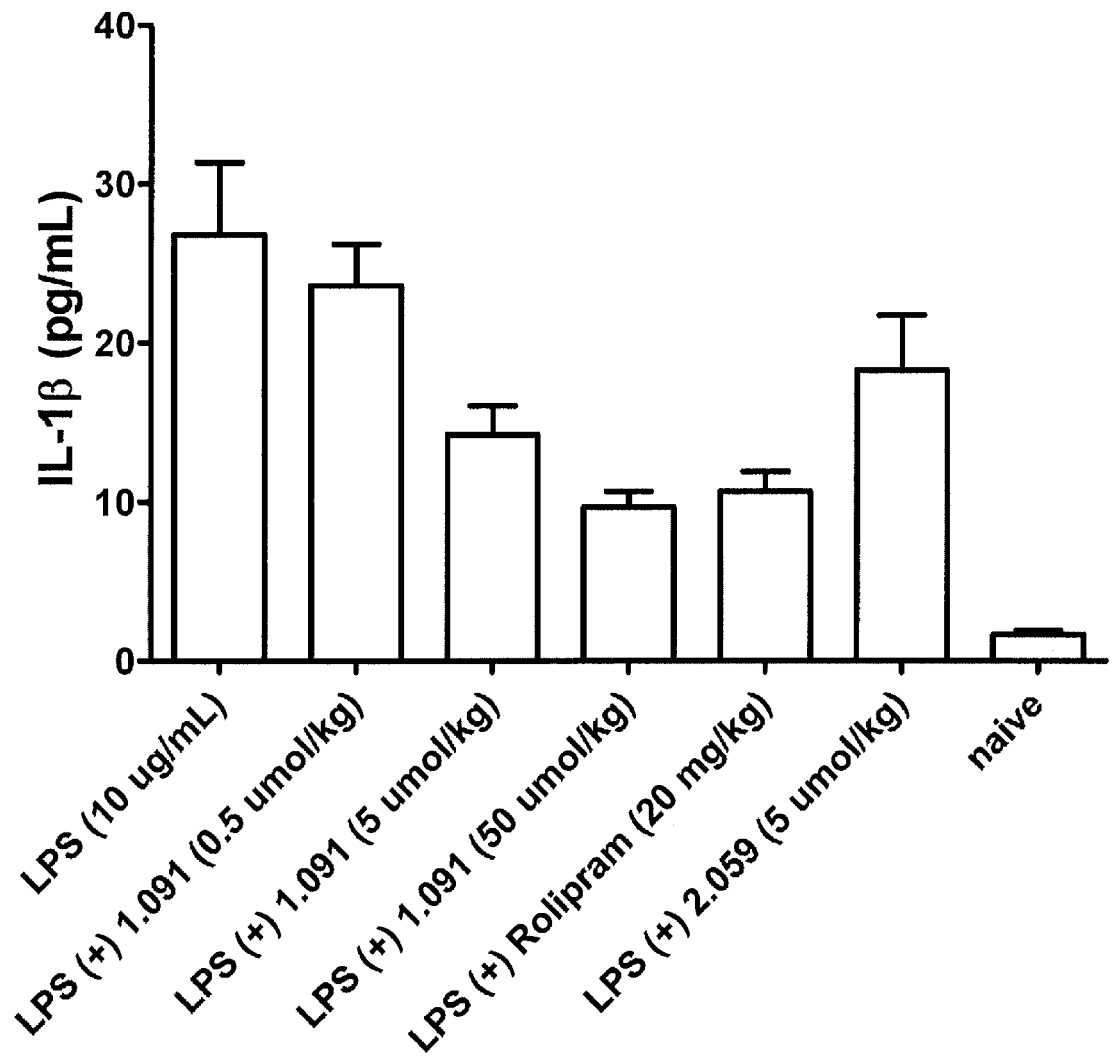
FIG. 12 shows the reduction of IL-1β levels in BALF from LPS-challenged mice upon intratracheal administration of Compound 1.091 or Compound 2.059. Data are reported as pg/mL of IL-1β and are mean±SEM.

FIG. 11 shows a significant reduction in pulmonary neutrophilia influx after intratracheal dosing of Compound 1.091. The efficacy of Compound 1.091 when dosed intratracheally is similar to the efficacy of the control compound rolipram dosed i.p. FIG. 12 shows the reduction in IL-1β after intratracheal administration of Compound 1.091 or Compound 2.059. These data demonstrate the efficacy of Rho kinase inhibitors of Formula I or II to inhibit inflammatory responses in vivo.

Example 16

Kinase Panel Screen

Relevance:

This assay demonstrates a compound's ability to inhibit members of a panel of kinases known to be involved in signaling pathways connected to inflammatory processes.

Protocol

Compounds of Formulae I and II were examined for activity against a selected panel of kinases using the KinaseProfiler™ enzyme profiling services (Upstate, Millipore Bioscience Division). Percent kinase activity at 10 µM and 1 µM test compound and 10 µM ATP was determined against 40 wild-type recombinant human kinases according to Upstate's standard protocol: ASK1, BTK, CSK, c-RAF, GCK, GSK3β, IKKα, IKKβ, IRAK1, IRAK4, JNK1α1, JNK2α2, JNK3, ERK1, ERK2, MAPKAP-K2, MAPKAP-K3, MEK1, MKK4, MKK6, MKK7β, Mnk2, MSK1, PAK3, PDK1, PRAK, ROCK1, Rsk2, SAPK2a, SAPK2b, SAPK3, SAPK4, SRPK1, SRPK2, Syk, TAK1, TBK1, PI3-Kβ, PI3-Kγ, PI3-Kδ.

Results:

Percent inhibition results are reported in Table 7 for four compounds against six kinases in the panel. Only compounds in which $R_2$ is $R_2$-2 were found to inhibit significantly GCK, ERK1/2, Mnk2 and IRAK1/2. Only ERK1/2 were inhibited by ~50% at 1 µM by both compounds 2.059 and 2.066.

TABLE 7

Percent inhibition data for six of the tested kinases

| | Compound 2.059 | | Compound 2.066 | | Compound 1.161 | | Compound 1.162 | |
|---|---|---|---|---|---|---|---|---|
| | 1 µM | 10 µM | 1 µM | 10 µM | 1 µM | 10 µM | 1 µM | 10 µM |
| ERK1 | 37 | 4 | 52 | 15 | 97 | 75 | 84 | 50 |
| ERK2 | 56 | 12 | 50 | 12 | 104 | 92 | 89 | 60 |
| Mnk2 | 49 | 12 | 99 | 54 | 108 | 106 | 111 | 65 |
| IRAK4 | 63 | 22 | 77 | 25 | 96 | 109 | 105 | 88 |
| IRAK1 | 87 | 30 | 74 | 32 | 106 | 99 | 100 | 97 |
| GCK | 75 | 34 | 39 | 7 | 96 | 91 | 93 | 75 |

Example 17

Rodent Pharmacokinetic Analyses of ROCK Inhibitors

Plasma (EDTA K2 anticoagulant) was collected from male, cannulated, CD Sprague Dawley rats to determine the pharmacokinetics of formulations containing compound inhibitors of Rho kinase. Each animal was dosed orally with a 4 ml/kg solution or suspension of each test compound in 10 mM acetate buffered saline, pH 4.5 at a final concentration range of 20-30 µmol/kg. Blood was collected at 0.25, 0.5, 1, 2, 4, 6, 8, and 24 hours. Plasma samples were assayed for the concentration of the test compound using an on-line, solid phase extraction LC/MS/MS analysis system.

Samples were analyzed on a QSTAR Elite, hybrid quadrupole time-of-flight mass spectrometer (Applied Biosystems, Framingham, Mass.) coupled with a Symbiosis Pharma integrated, on-line SPE-HPLC system (Spark Holland Inc., Plainsboro, N.J.). Analyst QS 2.0 software was used for instrument control, data acquisition and processing. An aliquot of each sample was injected onto a Luna C18 column (50×2 mm, 4 um, 80A, Phenomenex, Torrance, Calif.), and elution was carried out using a gradient from 2-98% acetonitrile. Mobile Phase A consisted of 0.1% ammonium hydroxide in water and Mobile Phase B consisted of 0.1% formic acid in acetonitrile. Pharmacokinetic analyses were performed using WinNonlin software version 5.2 (Pharsight Corporation, Mountain View, Calif.).

The pharmacokinetic results based on the observed plasma concentrations of the test compounds in rats are shown in Table 8.

TABLE 8

Pharmacokinetic results from rat oral PK studies (mean plasma values for n = 3 rats)

| Compound | Tmax (hr) | Cmax (nM) | AUC (0-last) (nM * hr) | t½ (hr) | Vz_F (L/kg) |
|---|---|---|---|---|---|
| 1.131 | 0.83 | 5610 | 10825 | 1.55 | 6.8 |
| 1.092 | 0.25 | 2101 | 1849 | 1.74 | 19.0 |
| 1.123 | 0.33 | 2044 | 2064 | 0.9 | 14.8 |
| 2.038 | 0.5 | 1037 | 1283 | 0.71 | 22.5 |
| 2.039 | 0.33 | 783 | 905 | 1.13 | 59.4 |
| 1.074 | 0.42 | 735 | 1167 | 0.86 | 45.7 |
| 1.107 | 1.67 | 544 | 1586 | 1.28 | 36.3 |
| 1.124 | 0.5 | 415 | 535 | 1.39 | 93.4 |
| 2.045 | 0.67 | 223 | 456 | 1.59 | 226 |
| 1.108 | 0.83 | 209 | 415 | 1.36 | 116 |
| 1.091 | BLQ | BLQ | BLQ | BLQ | BLQ |
| 2.026 | BLQ | BLQ | BLQ | BLQ | BLQ |
| 1.136 | BLQ | BLQ | BLQ | BLQ | BLQ |

BLQ indicates that the compound was below the limit of quantitation in the assay As determined from the plasma concentration versus time curves, the time to peak and peak exposure are represented by the values Tmax and Cmax, respectively. The AUC values (nM*hr) shown were calculated as the areas under the plasma concentration versus time curves from time zero through the time of the last observable value and represent the total exposure of the compound over the course of the study. Half-life values or the amount of time required for the plasma levels of the compound to decline to half the initial value are represented as t½. The volume of distribution (Vz_F expressed in L/kg) relates the amount of theoretical volume needed to account for the observed concentration of a given dose of a compound. For rats, the total body water content is approximately 0.15 L/kg. Calculated volumes of distribution below 0.15 L/kg are considered low, whereas values between 5 and 100 L/kg are considered high. The volume of distribution varies depending on the degree of plasma protein binding as well as partitioning of the compound into fat and tissues. Table 8 provides evidence that our ROCK inhibiting compounds have a varying degree of pharmacokinetic properties that would allow them to be optimized for multiple routes of administration. These compounds are quickly absorbed, as indicated by a Tmax of generally less than 1 hour, with varying degrees of peak and total exposure as indicated by Cmax and AUC, with higher values indicating greater exposure. Regardless of exposure, these compounds demonstrate a similar clearance, t½.

Additionally, compound concentrations were determined in the plasma and lungs of male, ovalbumin-sensitized, Balb/c mice from a murine model of asthma. Test compounds were formulated in water or 1% polysorbate 80 and dosed at 15 µmol/kg for intraperitoneal (IP) or oral (PO) administration or formulated for intratracheal (IT) administration and dosed at 5 µmol/kg, which directly targets the lungs. Following completion of the in vivo study, mice were euthanized and blood and plasma collected approximately 2.5-3 hours post administration of test compound for bronchodialator (BD) studies and 24 hours post administration for anti-inflamatory (AI) studies. Lungs were homogenized in Matrix A lysing tubes using a FastPrep 24 tissue and cell homogenizer (MP Biomedicals, Solon, Ohio). Both plasma samples and lung extracts were assayed for compound concentrations using an on-line, solid phase extraction LC/MS/MS system. The actual lung tissue concentrations of each compound in mouse were extrapolated from the lung and plasma concentrations, data are shown in Table 9. The results of a set of experiments using unsensitized mice and collecting only plasma 15 minutes post administration of test compounds are shown in Table 10.

TABLE 9

Compound concentrations in asthmatic mice lungs post IP, PO and IT administration (mean plasma corrected lung values for n = 9 or 10 mice)

| Compound | Efficacy Model | Route | Time Point, h | Lung, nM[1] |
|---|---|---|---|---|
| 1.131 | BD | PO | 3 | 7353 |
| 2.038 | BD | PO | 3 | 440 |
| 1.092 | BD | PO | 3 | 152 |
| 1.091 | BD | IP | 3 | 117 |
| 1.091 | BD | IT | 2.5 | 123 |
| 1.131 | AI | PO | 24 | 33 |
| 2.038 | AI | PO | 24 | 11 |

[1]for calculation of lung concentrations, it was assumed that 22.6% of the lung mass was plasma (R. H. Storey, Cancer Research, 943-947, 1951)

TABLE 10

Compound concentrations in mice at 15 min post administration (mean plasma values for n = 3 mice)

| Compound | Plasma Mean Concentration, nM | Plasma Concentration StdDev, nM |
|---|---|---|
| 1.072 | 1770.9 | 320.9 |
| 1.074 | 506.1 | 407.9 |
| 1.075 | 348.0 | 83.9 |
| 1.076 | 1715.0 | 474.9 |
| 1.077 | 25.9 | 0.2 |
| 1.078 | 1018.8 | 75.8 |
| 1.079 | 2442.5 | 302.9 |
| 1.090 | 5.9 | 5.2 |
| 1.091 | 333.8 | 82.7 |
| 1.092 | 314.3 | 60.4 |
| 1.093 | 362.6 | 148.7 |
| 1.106 | 441.4 | 146.7 |
| 1.107 | 211.1 | 129.5 |
| 1.108 | 394.5 | 9.0 |
| 1.109 | 187.2 | 36.0 |
| 1.110 | 792.0 | 311.9 |
| 1.123 | 71.4 | 11.8 |
| 1.124 | 118.0 | 2.4 |
| 1.126 | 0.0 | 0.0 |
| 1.127 | 980.2 | 757.5 |
| 1.131 | 444.5 | 130.0 |
| 1.132 | 982.4 | 207.7 |
| 1.133 | 1097.9 | 234.3 |
| 1.134 | 1550.8 | 623.9 |
| 1.135 | 656.8 | 115.4 |
| 1.136 | 25.9 | 6.3 |
| 1.137 | 556.9 | 279.8 |
| 1.138 | 1863.8 | 378.7 |
| 1.141 | 1643.1 | 368.6 |
| 1.142 | 329.7 | 171.6 |
| 1.143 | 274.5 | 68.8 |
| 1.145 | 109.0 | 117.9 |
| 1.146 | 1255.7 | 703.5 |
| 1.148 | 767.1 | 63.9 |
| 1.149 | 1559.4 | 789.6 |
| 1.150 | 1392.3 | 1278.3 |
| 1.151 | 478.6 | 173.6 |
| 1.152 | 435.4 | 44.5 |
| 1.153 | 521.5 | 61.3 |
| 1.154 | 1039.5 | 447.9 |
| 1.155 | 32.4 | 36.3 |
| 1.156 | 88.0 | 37.5 |
| 1.157 | 357.2 | 131.9 |
| 1.158 | 101.6 | 54.4 |
| 1.159 | 250.5 | 343.2 |
| 1.161 | 392.5 | 14.9 |
| 1.162 | 76.1 | 12.9 |
| 1.163 | 10.1 | 1.1 |
| 1.164 | 1504.3 | 580.6 |
| 1.165 | 93.5 | 49.6 |
| 1.166 | 342.4 | 118.1 |
| 1.168 | 587.5 | 258.9 |
| 1.170 | 638.6 | 154.7 |
| 1.171 | 368.8 | 208.9 |
| 1.172 | 111.1 | 32.0 |
| 1.173 | 144.4 | 72.6 |
| 1.175 | 1126.5 | 112.5 |
| 1.176 | 89.1 | 69.1 |
| 1.177 | 283.1 | 125.6 |
| 1.182 | 452.5 | 297.7 |
| 1.183 | 708.5 | 359.6 |
| 1.185 | 1023.6 | 492.8 |
| 1.186 | 2169.4 | 1599.1 |
| 1.191 | 260.0 | 58.8 |
| 1.193 | 55.4 | 26.0 |
| 1.194 | 355.0 | 133.5 |
| 1.195 | 107.9 | 23.1 |
| 1.197 | 453.1 | 354.0 |
| 1.198 | 643.2 | 112.1 |
| 1.200 | 0.0 | 0.0 |
| 1.202 | 129.7 | 71.9 |
| 1.203 | 1134.7 | 44.2 |
| 1.204 | 549.1 | 183.6 |
| 1.206 | 671.5 | 80.9 |
| 1.208 | 281.1 | 45.4 |
| 1.210 | 285.8 | 122.9 |
| 1.212 | 863.4 | 104.1 |
| 1.213 | 396.4 | 135.1 |
| 1.215 | 2651.2 | 529.0 |
| 1.217 | 292.5 | 176.0 |
| 1.219 | 1678.9 | 516.3 |
| 1.223 | 12.8 | 0.6 |
| 1.226 | 526.1 | 157.9 |
| 1.227 | 1859.4 | 603.7 |
| 1.229 | 1453.9 | 465.0 |
| 1.233 | 41.1 | 11.6 |
| 1.234 | 239.6 | 79.4 |
| 1.236 | 47.7 | 18.1 |
| 1.237 | 178.4 | 64.6 |
| 1.238 | 48.3 | 29.6 |
| 1.239 | 258.9 | 111.8 |
| 1.241 | 991.4 | 134.5 |
| 1.242 | 579.8 | 314.0 |
| 1.245 | 1524.0 | 127.5 |
| 1.246 | 587.4 | 299.7 |
| 1.249 | 2147.1 | 688.2 |
| 1.252 | 1259.2 | 1210.0 |
| 1.253 | 240.0 | 20.3 |
| 1.258 | 567.5 | 223.5 |
| 1.259 | 264.4 | 39.1 |
| 1.260 | 291.2 | 120.7 |
| 1.262 | 285.2 | 76.2 |
| 2.025 | 73.7 | 21.2 |
| 2.026 | 629.5 | 94.6 |
| 2.027 | 502.6 | 248.5 |
| 2.031 | 1430.4 | 139.2 |
| 2.034 | 664.7 | 649.4 |
| 2.036 | 1343.9 | 1603.3 |

TABLE 10-continued

Compound concentrations in mice at 15 min post administration (mean plasma values for n = 3 mice)

| Compound | Plasma Mean Concentration, nM | Plasma Concentration StdDev, nM |
|---|---|---|
| 2.038 | 728.9 | 222.8 |
| 2.039 | 92.0 | 47.6 |
| 2.041 | 986.5 | 287.0 |
| 2.043 | 60.8 | 24.7 |
| 2.046 | 488.1 | 96.1 |
| 2.047 | 3.0 | 1.7 |
| 2.054 | 765.5 | 214.3 |
| 2.055 | 656.1 | 172.6 |
| 2.056 | 1257.0 | 230.6 |
| 2.057 | 431.2 | 41.5 |
| 2.058 | 193.6 | 167.4 |
| 2.059 | 89.6 | 21.5 |
| 2.060 | 307.6 | 157.6 |
| 2.061 | 73.2 | 21.1 |
| 2.062 | 659.9 | 582.8 |
| 2.063 | 347.9 | 248.5 |
| 2.064 | 201.6 | 78.7 |
| 2.065 | 236.4 | 29.8 |
| 2.066 | 491.6 | |

The results of these quantitative analyses have enabled the selection of compounds for additional studies based on desirable pharmacokinetic profiles and preferential distribution in the target organ (lungs). We have identified compounds which possess high bioavailability and efficacy against airway hyperreactivity when dosed orally, as well as compounds that are efficacious when administered intraperitoneally or intratracheally, but do not reach systemic levels when dosed orally and thus are not efficacious by the oral route. Characterization of the pharmacokinetic properties and distribution of these Rho Kinase inhibitors is an essential part of the selection of compounds for drug development.

Example 18

Summary of Data of Preferred Compounds

Principal biological data describing the preferred compounds of the invention have been collected into Table 11. Displayed in this table are ROCK1 and ROCK2 average Ki values in nM (as detailed in Example 1), average percent of stimulated IL-1β, IL-6, and TNF-α secretion from human monocytes at 10 μM of test compound (as detailed in Example 14), average $IC_{50}$ for inhibition of fMLP-induced neutrophil chemotaxis in μM (as detailed in Example 2), mean compound plasma concentrations in mice at 15 minutes post oral administration (as detailed in Example 17).

TABLE 11

Summary of Data of Preferred Compounds

| Compound | ROCK1 Ki, nM | ROCK2 Ki, nM | IL-1β % | IL-6, % | TNF-α % | Chemotaxis IC50, μM | Mouse Oral PK, nM |
|---|---|---|---|---|---|---|---|
| 1.074 | 40.1 | 4.1 | 43.9 | 96.0 | 87.7 | | 506 |
| 1.075 | 48.7 | 4.4 | 49.7 | 73.9 | 51.6 | | 348 |
| 1.076 | 14.3 | 2.6 | 51.0 | 81.2 | 78.9 | | 1715 |
| 1.077 | 76.1 | 11.1 | 30.3 | 43.3 | 52.3 | | 26 |
| 1.079 | 71.5 | 4.7 | 59.3 | 31.1 | 56.5 | | 2443 |
| 1.091 | 71.4 | 3.3 | 165.5 | 108.2 | 104.6 | 2.3 | 334 |
| 1.093 | 64.5 | 7.7 | 109.0 | 49.7 | 76.1 | | 363 |
| 1.108 | 25.6 | 6.5 | 131.3 | 89.8 | 116.7 | | 395 |
| 1.109 | 58.8 | 9.6 | 190.5 | 312.9 | 118.3 | | 187 |
| 1.123 | 82.3 | 9.6 | 82.6 | 64.7 | 62.7 | 3.1 | 71 |
| 1.124 | 64.5 | 3.3 | 99.5 | 101.4 | 61.5 | 3.4 | 118 |
| 1.126 | 76.2 | 17.2 | | | | | 0 |
| 1.131 | 19.7 | 3.8 | 48.3 | 68.6 | 85.2 | 1.6 | 445 |
| 1.132 | 22.5 | 3.5 | 58.6 | 72.5 | 80.3 | | 982 |
| 1.133 | 25.0 | 4.3 | 54.5 | 70.7 | 66.2 | | 1098 |
| 1.134 | 22.4 | 4.4 | 43.2 | 74.6 | 69.1 | | 1551 |
| 1.135 | 40.3 | 5.4 | 57.0 | 123.2 | 108.0 | | 657 |
| 1.136 | 25.8 | 5.1 | 66.3 | 95.0 | 71.5 | 2.6 | 26 |
| 1.137 | 36.3 | 7.2 | 40.3 | 46.2 | 58.0 | | 557 |
| 1.138 | 41.1 | 6.3 | 257.4 | 76.6 | 130.9 | 1.9 | 1864 |
| 1.141 | 28.5 | 3.8 | 50.4 | 71.7 | 75.7 | | 1643 |
| 1.148 | 24.3 | 3.6 | 63.9 | 78.6 | 56.1 | | 767 |
| 1.149 | 46.8 | 4.2 | 69.8 | 121.5 | 119.9 | | 1559 |
| 1.150 | 33.2 | 3.2 | 78.2 | 89.2 | 94.4 | | 1392 |
| 1.152 | 19.8 | 3.3 | 74.7 | 94.7 | 120.1 | | 435 |
| 1.153 | 62.8 | 4.2 | 64.1 | 106.2 | 74.3 | | 522 |
| 1.155 | 45.4 | 7.0 | 76.7 | 121.8 | 79.7 | | 32 |
| 1.156 | 135.8 | 13.0 | 60.7 | 92.5 | 70.5 | | 88 |
| 1.157 | 263.8 | 8.8 | 121.4 | 92.6 | 65.1 | | 357 |
| 1.158 | 64.1 | 5.1 | 80.8 | 133.1 | 86.6 | | 102 |
| 1.161 | 9.9 | 2.5 | 87.7 | 86.3 | 153.5 | | 392 |
| 1.162 | 15.2 | 2.8 | 95.5 | 99.8 | 158.7 | | 76 |
| 1.163 | 33.6 | 2.9 | 166.7 | 140.9 | 91.6 | | 10 |
| 1.164 | 42.4 | 6.1 | 80.1 | 109.5 | 89.0 | | 1504 |
| 1.165 | 50.7 | 3.4 | 129.9 | 114.3 | 103.5 | | 94 |
| 1.166 | 95.2 | 8.0 | 107.0 | 87.2 | 82.2 | | 342 |
| 1.171 | 109.2 | 16.0 | 78.9 | 91.8 | 72.2 | | 369 |
| 1.173 | 15.1 | 3.6 | 86.1 | 79.5 | 80.1 | | 144 |
| 1.175 | 65.9 | 7.6 | 29.3 | 38.2 | 47.4 | | 1126 |
| 1.176 | 314.3 | 11.2 | 95.2 | 112.4 | 72.4 | | 89 |
| 1.186 | 129.3 | 11.9 | 64.1 | 105.3 | 68.2 | | 2169 |

TABLE 11-continued

Summary of Data of Preferred Compounds

| Compound | ROCK1 Ki, nM | ROCK2 Ki, nM | IL-1β % | IL-6, % | TNF-α % | Chemotaxis IC50, μM | Mouse Oral PK, nM |
|---|---|---|---|---|---|---|---|
| 1.193 | 64.9 | 14.8 | | | | | 55 |
| 1.195 | 196.2 | 10.3 | 115.4 | 94.4 | 67.7 | | 108 |
| 1.197 | 120.2 | 5.0 | 179.1 | 128.8 | 83.3 | | 453 |
| 1.200 | 76.5 | 5.9 | 0.0 | 0.0 | 0.2 | | 0 |
| 1.206 | 64.4 | 9.1 | 88.7 | 164.0 | 97.3 | | 672 |
| 1.212 | 44.2 | 3.9 | 116.3 | 111.0 | 108.1 | | 863 |
| 1.213 | 106.3 | 3.0 | 111.1 | 81.7 | 77.4 | | 396 |
| 1.215 | 102.8 | 3.5 | 136.7 | 63.2 | 60.4 | | 2651 |
| 1.217 | 70.1 | 12.1 | 118.6 | 73.8 | 71.3 | | 293 |
| 1.219 | 343.6 | 15.4 | 138.9 | 127.7 | 82.1 | | 1679 |
| 1.223 | 239.5 | 15.7 | 117.0 | 88.5 | 60.7 | | 13 |
| 1.233 | 47.2 | 1.3 | 78.5 | 78.9 | 79.0 | | 41 |
| 1.236 | 49.3 | 2.1 | 75.2 | 93.0 | 98.0 | | 48 |
| 1.237 | 286.7 | 4.0 | 97.1 | 100.9 | 70.6 | | 178 |
| 1.238 | 61.2 | 1.5 | 101.1 | 62.9 | 73.2 | | 48 |
| 1.239 | 282.6 | 6.3 | 39.4 | 84.7 | 58.5 | | 259 |
| 1.249 | 91.7 | 8.6 | 133.8 | 56.2 | 60.0 | | 2147 |
| 1.252 | 30.5 | 4.5 | 139.2 | 68.3 | 101.6 | | 1259 |
| 1.253 | 59.9 | 1.7 | 160.6 | 228.6 | 126.8 | | 240 |
| 1.258 | 9.5 | 1.3 | 104.1 | 83.5 | 94.0 | | 567 |
| 1.259 | 19.5 | 2.1 | | | | | 264 |
| 1.260 | 70.9 | 7.1 | | | | | 291 |
| 1.261 | 307.4 | 14.8 | | | | | |
| 1.262 | 54.9 | 4.0 | 145.7 | 156.6 | 135.3 | | 285 |
| 1.270 | 130.5 | 9.9 | | | | | |
| 1.273 | 31.3 | 8.2 | | | | | |
| 1.275 | 401.7 | 14.1 | | | | | |
| 1.277 | 42.3 | 4.6 | | | | | |
| 1.281 | 71.8 | 7.4 | | | | | |
| 2.025 | 6.9 | 2.9 | | | | 1.7 | 74 |
| 2.026 | 38.0 | 13.0 | 166.0 | 180.7 | 109.1 | 3.8 | 629 |
| 2.031 | 14.6 | 5.3 | 49.0 | 89.3 | 66.4 | | 1430 |
| 2.038 | 28.9 | 6.3 | 90.8 | 79.7 | 70.2 | 0.7 | 729 |
| 2.039 | 18.8 | 6.7 | 49.8 | 70.3 | 47.8 | 1.6 | 92 |
| 2.041 | 30.8 | 9.6 | | | | | 987 |
| 2.046 | 16.7 | 5.6 | | | | | 488 |
| 2.047 | 26.4 | 7.0 | | | | | 3 |
| 2.054 | 17.1 | 3.7 | 24.0 | 56.8 | 37.9 | | 765 |
| 2.055 | 16.0 | 6.4 | | | | | 656 |
| 2.057 | 6.2 | 3.7 | | | | | 431 |
| 2.058 | 15.3 | 3.3 | 1.2 | 1.3 | 10.6 | | 194 |
| 2.059 | 3.9 | 2.7 | 0.3 | 0.0 | 6.9 | | 90 |
| 2.060 | 4.9 | 3.2 | 5.9 | 19.6 | 33.0 | | 308 |
| 2.061 | 10.5 | 1.8 | | | | | 73 |
| 2.064 | 4.1 | 2.2 | 14.3 | 45.7 | 66.2 | | 202 |
| 2.065 | 4.1 | 1.8 | | | | | 236 |
| 2.066 | 10.2 | 2.3 | 0.0 | 0.0 | 25.2 | | 492 |
| 2.067 | 19.6 | 4.2 | | | | | |
| 2.068 | 8.0 | 5.8 | | | | | |
| 2.069 | 16.7 | 2.4 | | | | | |
| 2.072 | 7.5 | 4.4 | | | | | |
| 2.073 | 12.7 | 4.2 | | | | | |
| 2.076 | 8.0 | 2.4 | | | | | |
| 2.077 | 33.7 | 5.0 | | | | | |
| 2.078 | 18.3 | 2.6 | | | | | |
| 2.079 | 18.5 | 2.3 | | | | | |
| 2.082 | 131.7 | 9.0 | | | | | |
| 2.096 | 70.2 | 9.6 | | | | | |
| 2.097 | 35.4 | 2.8 | | | | | |
| 2.099 | 15.0 | 3.8 | | | | | |

Although the invention has been described with reference to the presently preferred embodiments, it should be understood that various modifications could be made without departing from the scope of the invention.

What is claimed:

1. A method of treating nociceptive pain, the method comprises the steps of first identifying a subject suffering from nociceptive pain, then administering to the subject an effective amount of a compound of Formula II to treat nociceptive pain;

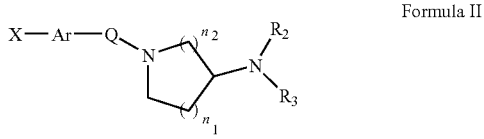

Formula II wherein:
- Q is $(CR_4R_5)_{n3}$;
- $n_1$ is 1;
- $n_2$ is 1;
- $n_3$ is 0, 1, 2, or 3;
- $R_2$ is $R_2$-2, optionally substituted:

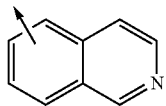

$R_2$-2

Ar is indazole;

X is from 1 to 3 substituents on Ar, each independently in the form Y—Z, in which Z is attached to Ar;

Y is one or more substituents on Z, and each is independently $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$;

Z is alkyl, alkenyl, alkynyl, aryl, or cycloalkyl;

$R_3$-$R_5$ are independently H, alkyl, or cycloalkyl, optionally substituted;

$R_8$-$R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle.

2. The method according to claim 1, wherein said compound is Compound 2.058, which is (R)-2-(6-((3-(isoquinolin-5-ylamino)pyrrolidin-1-yl)methyl)-1H-indol-1-yl)acetamide; Compound 2.059, which is (R)-2-(5-((3-(isoquinolin-5-ylamino)pyrrolidin-1-yl)methyl)-1H-indol-1-yl)acetamide; Compound 2.060, which is (R)-2-(6-((3-(isoquinolin-5-ylamino)pyrrolidin-1-yl)methyl)-1H-indol-1-yl)ethanol; Compound 2.066, which is (R)-2-(5-((3-(isoquinolin-5-ylamino)pyrrolidin-1-yl)methyl)-1H-indol-1-yl)ethanol; or Compound 2.072, which is (R)-2-(3-((3-(isoquinolin-5-ylamino)pyrrolidin-1-yl)methyl)-1H-indol-1-yl)ethanol.

3. The method according to claim 1, wherein $n_3$ is 1 or 2.

4. The method according to claim 2, wherein said compound is Compound 2.066.

5. The method according to claim 1, wherein Y is $OR_8$.

6. The method according to claim 1, wherein Y is $CONR_8R_9$.

7. The method according to claim 2, wherein said compound is Compound 2.059.

* * * * *